(12) United States Patent
Ukita

(10) Patent No.: US 11,433,395 B2
(45) Date of Patent: Sep. 6, 2022

(54) SEPARATING APPARATUS, SEPARATING METHOD, SEPARATING DEVICE, INSPECTION APPARATUS, AND INSPECTION METHOD

(71) Applicant: UNIVERSITY OF YAMANASHI, Kofu (JP)

(72) Inventor: Yoshiaki Ukita, Yamanashi (JP)

(73) Assignee: UNIVERSITY OF YAMANASHI, Kofu (JP)

( * ) Notice: Subject to any disclaimer, the term of this patent is extended or adjusted under 35 U.S.C. 154(b) by 264 days.

(21) Appl. No.: 16/964,628

(22) PCT Filed: Jan. 24, 2019

(86) PCT No.: PCT/JP2019/002379
§ 371 (c)(1),
(2) Date: Jul. 24, 2020

(87) PCT Pub. No.: WO2019/146734
PCT Pub. Date: Aug. 1, 2019

(65) Prior Publication Data
US 2021/0053060 A1    Feb. 25, 2021

(30) Foreign Application Priority Data
Jan. 25, 2018    (JP) .............................. JP2018-010215

(51) Int. Cl.
*B01L 3/00*    (2006.01)
(52) U.S. Cl.
CPC ... *B01L 3/502753* (2013.01); *B01L 3/502715* (2013.01); *B01L 3/502738* (2013.01);
(Continued)

(58) Field of Classification Search
CPC ..... B01L 2300/0816; B01L 2300/0887; B01L 2400/0409; B01L 2300/0645;
(Continued)

(56) References Cited

U.S. PATENT DOCUMENTS

2006/0084174 A1    4/2006  Ogawa et al.
2017/0080422 A1    3/2017  Maaskant et al.

FOREIGN PATENT DOCUMENTS

JP    2003344421 A    12/2003
JP    2004109082 A    4/2004
(Continued)

OTHER PUBLICATIONS

Haeberle, S., et al., "Centrifugal extraction of plasma from whole blood on a rotating disk", Lab Chip, 6, 776-781, 2006.
(Continued)

*Primary Examiner* — Jennifer Wecker
*Assistant Examiner* — Oyeleye Alexander Alabi
(74) *Attorney, Agent, or Firm* — Buchanan Ingersoll & Rooney PC

(57) ABSTRACT

Provided is a separating apparatus including separating unit configured to apply external force to a fluid sample containing two or more components immiscible with each other and having different specific gravities to separate the fluid sample into separation target and non-separation target, and a transfer mechanism configured to apply a pressure to the separation target separated by the separating unit to transfer the separation target.

19 Claims, 45 Drawing Sheets

(52) U.S. Cl.
CPC . *B01L 2200/027* (2013.01); *B01L 2200/0684* (2013.01); *B01L 2200/10* (2013.01); *B01L 2300/0816* (2013.01); *B01L 2300/0887* (2013.01); *B01L 2400/0409* (2013.01)

(58) Field of Classification Search
CPC ..... B01L 2300/0864; B01L 2400/0487; B01L 3/502723; B01L 2200/0621; B01L 2200/0673; B01L 2300/0803; B01L 3/502769; B01L 3/50273; G01N 33/48; G01N 35/00
See application file for complete search history.

(56) References Cited

FOREIGN PATENT DOCUMENTS

| | | |
|---|---|---|
| JP | 2013088211 A | 5/2013 |
| JP | 2017075807 A | 4/2017 |
| JP | 2017517390 A | 6/2017 |
| WO | 2013045695 A2 | 4/2013 |
| WO | 2016043196 A1 | 3/2016 |

OTHER PUBLICATIONS

Lee, B. S., et al., "A fully automated immunoassay from whole blood on a disc", Lab Chip, 9, 1548-1555, 2009.
International Search Report (PCT/ISA/210) dated Apr. 23, 2019, by the Japan Patent Office as the International Searching Authority for International Application No. PCT/JP2019/002379.
International Preliminary Report on Patentability (Forms PCT/IPEA/416 and PCT/IPEA/409) dated Nov. 26, 2019, by the Japanese Patent Office for International Application No. PCT/JP2019/002379.
Written Opinion (PCT/ISA/237) dated Apr. 23, 2019, by the Japan Patent Office as the International Searching Authority for International Application No. PCT/JP2019/002379.
Written Opinion of the International Preliminary Examining Authority (Form PCT/IPEA/408) dated Oct. 8, 2019, by the Japanese Patent Office as the International Searching Authority for International Application No. PCT/JP2019/002379.

FIG. 10A
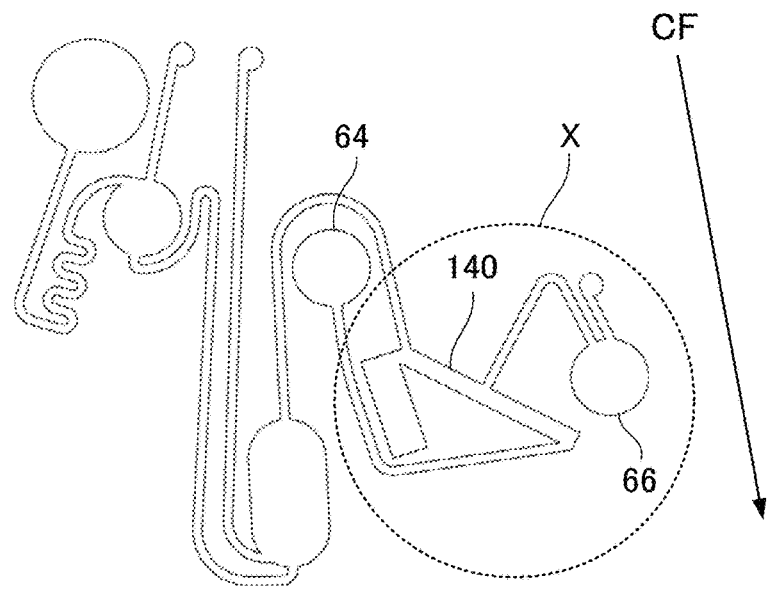
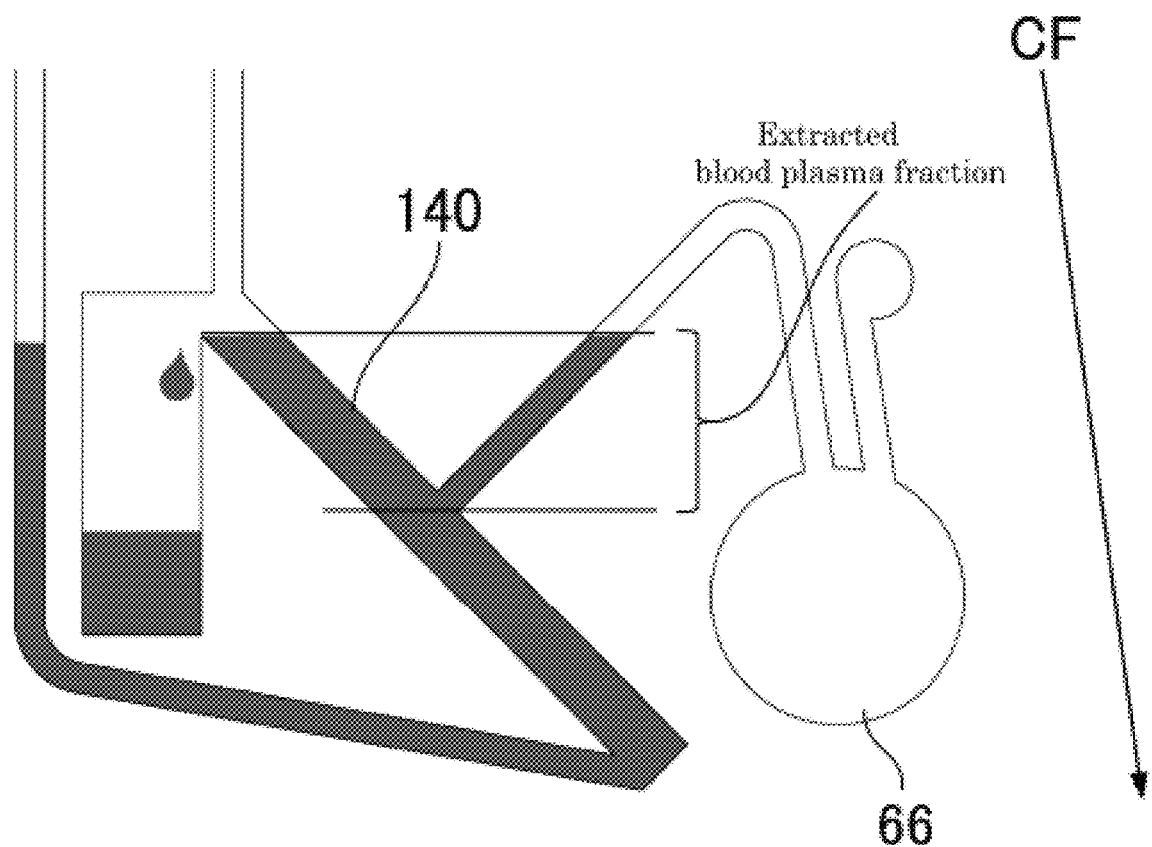
FIG. 10B

FIG. 19
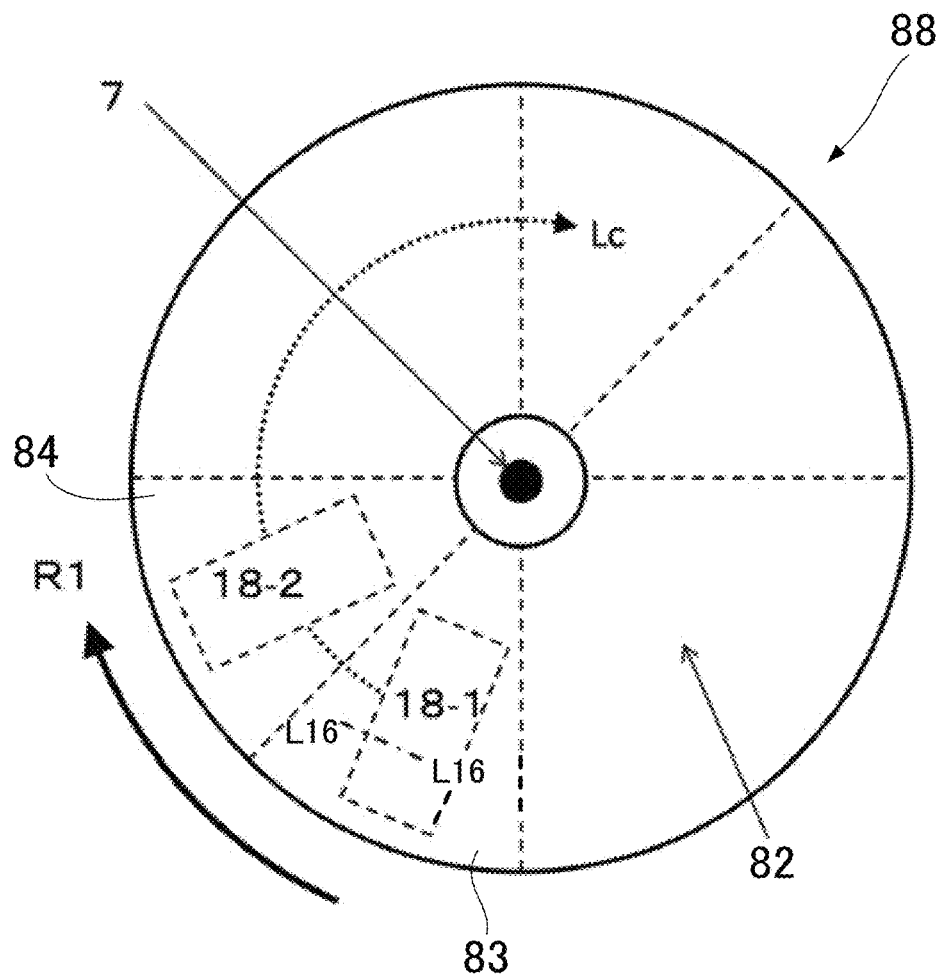
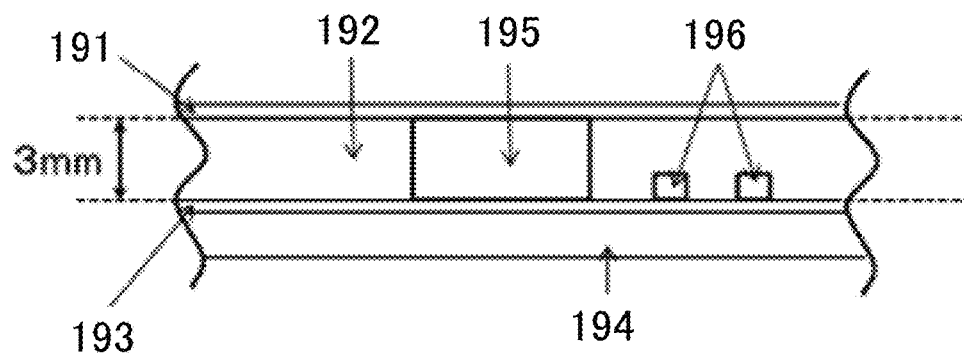
FIG. 20

SEPARATING APPARATUS, SEPARATING METHOD, SEPARATING DEVICE, INSPECTION APPARATUS, AND INSPECTION METHOD

TECHNICAL FIELD

The present invention relates to a separating apparatus and a separating method, a separating device, and a testing apparatus and a testing method.

BACKGROUND ART

Blood includes blood plasma, which is a liquid component, and, for example, blood corpuscles, which are solid components, and is a clinical specimen most often used. Useful information from the blood is often obtained through analyses of biomarkers contained in the blood plasma. In analyses of biomarkers, the solid components in the blood may constitute a cause of chemical and physical inhibitions. Hence, for analyses of biomarkers in the blood plasma, the blood is previously separated into, for example, the blood corpuscles, which are the solid components, and the blood plasma, which is the liquid component, and the separated blood plasma is used as a specimen.

In recent years, techniques for microanalyses of biomarkers have been developed, aiming for micropreparation of specimens and reagents, and acceleration and automation of analyses. One technical issue is to efficiently separate blood. In order to solve the technical issue, various blood separating techniques using centrifugal microfluidic devices have been developed.

A reported blood separating technique using such a centrifugal microfluidic device is, for example, a blood separating apparatus 200 illustrated in FIG. 1 including a weighing chamber 201 into which blood is introduced, a separating chamber 203 configured to separate blood, and a decant chamber 204 configured to store blood plasma separated (for example, see NPL 1). When a centrifugal force is applied to the blood separating apparatus 200, blood is gradually transferred from the weighing chamber 201 to the separating chamber 203 through a thin, long flow path 202, and is stored in the separating chamber 203 while separation of blood plasma is performed. The separated blood plasma is transferred from the separating chamber 203 to the decant chamber 204.

Another report is, for example, an analyzing apparatus 210 illustrated in FIG. 2A and FIG. 2B including a blood introducing chamber 211 into which blood is introduced, a separating chamber 212 configured to separate blood, and a valve 213 provided at a side of the separating chamber 212 and formed of a wax for closing the flow path (for example, see PTL 2). When a centrifugal force is applied to the analyzing apparatus 210, blood moves from the blood introducing chamber 211 to the separating chamber 212 and is separated in the separating chamber 212, and with the valve 213 opened by infrared laser irradiation, separated blood plasma is transferred to an analyzing section and analyzed.

Yet another report is a blood analyzing apparatus 210 illustrated in FIG. 31A, FIG. 31B, and FIG. 31C including a blood introducing port 302 configured to introduce blood 601, a blood corpuscle fraction storing section 501 configured to separate the blood 601, analyzing units 306 and 307 configured to analyze a separated blood plasma component 602, and outlet-side through-holes 304 and 305 to which external suction pumps are joined to suction the separated blood plasma component 602 into the analyzing units 306 and 307 (for example, see PTL 1). When a centrifugal force is applied to the blood analyzing apparatus 210, the blood 601 moves from the blood introducing port 302 to the blood corpuscle fraction storing section 501 to have a blood corpuscle fraction 603 precipitated in the blood corpuscle fraction storing section 501 while having the blood plasma component 602 separated as a centrifugal supernatant, and by a suction negative pressure of the external suction pumps joined to the outlet-side through holes 304 and 305, the separated blood plasma component 602 is suctioned into the analyzing unit 306 and 307 and analyzed.

CITATION LIST

Patent Literature
PTL 1: Japanese Patent Application Laid-Open (JP-A) No. 2004-109082
Non-Patent Literature
NPL 1: Stefan Haeberle et al. Lab Chip, 2006, 6, 776-781
NPL 2: Beom Seok Lee et al. Lab Chip, 2009, 9, 1548-1555

SUMMARY OF INVENTION

Technical Problem

In order to adjust the flow rate of the blood, the blood separating apparatus 200 of FIG. 1 flows the blood slowly through the thin, long flow path 202 and gains a flow path resistance, to control the flow rate of the blood. When the blood is slowly flowed through the thin, long flow path 202, the coagulation factor in the blood may be activated through contact with the flow path to coagulate the blood and clog the thin, long flow path 202. Moreover, because the blood separating apparatus 200 of FIG. 1 is configured to separate blood plasma while spinning down blood corpuscles, there is a risk that blood corpuscles may mix in the blood plasma due to the influence of a surface tension.

The analyzing apparatus 210 of FIG. 2A and FIG. 2B needs suspension of disk rotation and position alignment when opening the valve 213 by infrared laser irradiation, and hence needs complicated control. The wax constituting the valve 213 and iron oxide particles contained in the valve may become contamination.

The blood analyzing apparatus 210 of FIG. 31A, FIG. 31B, and FIG. 31C is configured to have the separated blood plasma component 602 suctioned into the analyzing units 306 and 307 by a suction negative pressure of the external suction pumps. Therefore, air bubbles occur and expand in the blood plasma component 602. Therefore, the volume of the blood plasma component 602 becomes inaccurate and an accurate analysis cannot be performed. Moreover, the device becomes complicated because external suction pumps are needed.

The present invention aims for solving the various problems in the related art described above and achieving an object described below. That is, the present invention has an object to provide a separating apparatus capable of separating a separation target with an extremely high purity from a fluid sample containing two or more components immiscible with each other and having different specific gravities by means of a simple mechanism, a separating method capable of efficiently separating a separation target with an extremely high purity from a fluid sample containing two or more components immiscible with each other and having different specific gravities in a simple manner, a separating device, and a testing apparatus and a testing method using the same.

Solution to Problem

A separating apparatus of the present invention as a solution to the problem described above includes a separating unit configured to apply an external force to a fluid sample containing two or more components immiscible with each other and having different specific gravities to separate the fluid sample into a separation target and a non-separation target, and a transfer mechanism configured to apply a pressure to the separation target separated by the separating unit to transfer the separation target.

A separating method of the present invention includes a separating step of applying an external force to a fluid sample containing two or more components immiscible with each other and having different specific gravities to separate the fluid sample into a separation target and a non-separation target, and a transferring step of applying a pressure to the separation target separated in the separating step to transfer the separation target.

A separating device of the present invention is a separating device used in any of the separating apparatus of the present invention described above and the testing apparatus of the present invention described above, and includes an introducing unit into which a fluid sample is introduced, a separating chamber communicably joined to the introducing unit and capable of separating the fluid sample into two or more fractions in response to application of an external force, a pressurizing medium chamber communicating with the separating chamber and capable of transferring a pressurizing medium into the separating chamber in response to application of an external force, and a transfer path communicating with the separating chamber and capable of transferring the fractions in the separating chamber to outside the separating chamber in response to application of an external force.

A testing apparatus of the present invention includes a separating unit formed of the separating apparatus of the present invention described above, and a testing unit configured to test a separation target separated and transferred by the separating unit.

A testing method of the present invention includes a separating step of applying an external force to a fluid sample containing two or more components immiscible with each other and having different specific gravities to separate the fluid sample into a separation target and a non-separation target, a transferring step of applying a pressure to the separation target separated in the separating step to transfer the separation target, and a testing step of testing the separation target transferred in the transferring step.

Advantageous Effects of Invention

The present invention can provide a separating apparatus capable of separating a separation target with an extremely high purity from a fluid sample containing two or more components immiscible with each other and having different specific gravities by means of a simple mechanism, a separating method capable of efficiently separating a separation target with an extremely high purity from a fluid sample containing two or more components immiscible with each other and having different specific gravities in a simple manner, a separating device, and a testing apparatus and a testing method using the same.

BRIEF DESCRIPTION OF DRAWINGS

FIG. 10A is a view illustrating an example of a separating apparatus including a metering unit;

FIG. 10B is a partially enlarged view of FIG. 10A;

FIG. 19 is a view illustrating an example of a disk on which a testing apparatus of a first embodiment is mounted;

FIG. 20 is a cross-sectional view of FIG. 19 taken along a line L16-L16;

Figure 1:
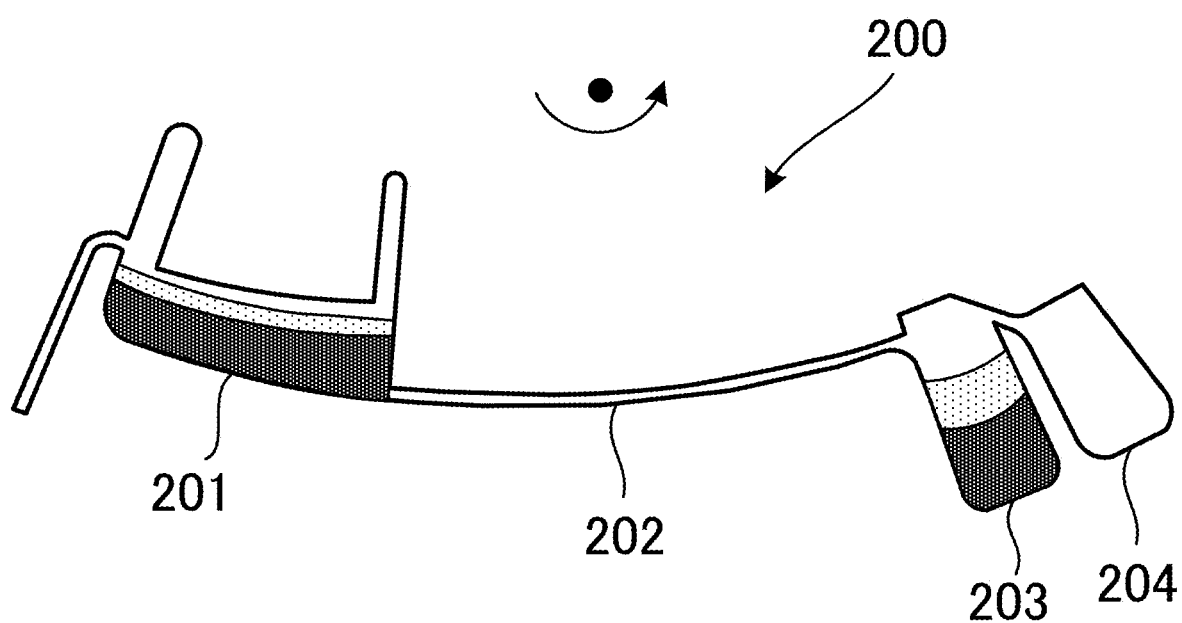
FIG. 1 is a schematic view illustrating an example of an existing blood separating apparatus.
Figure 2A:
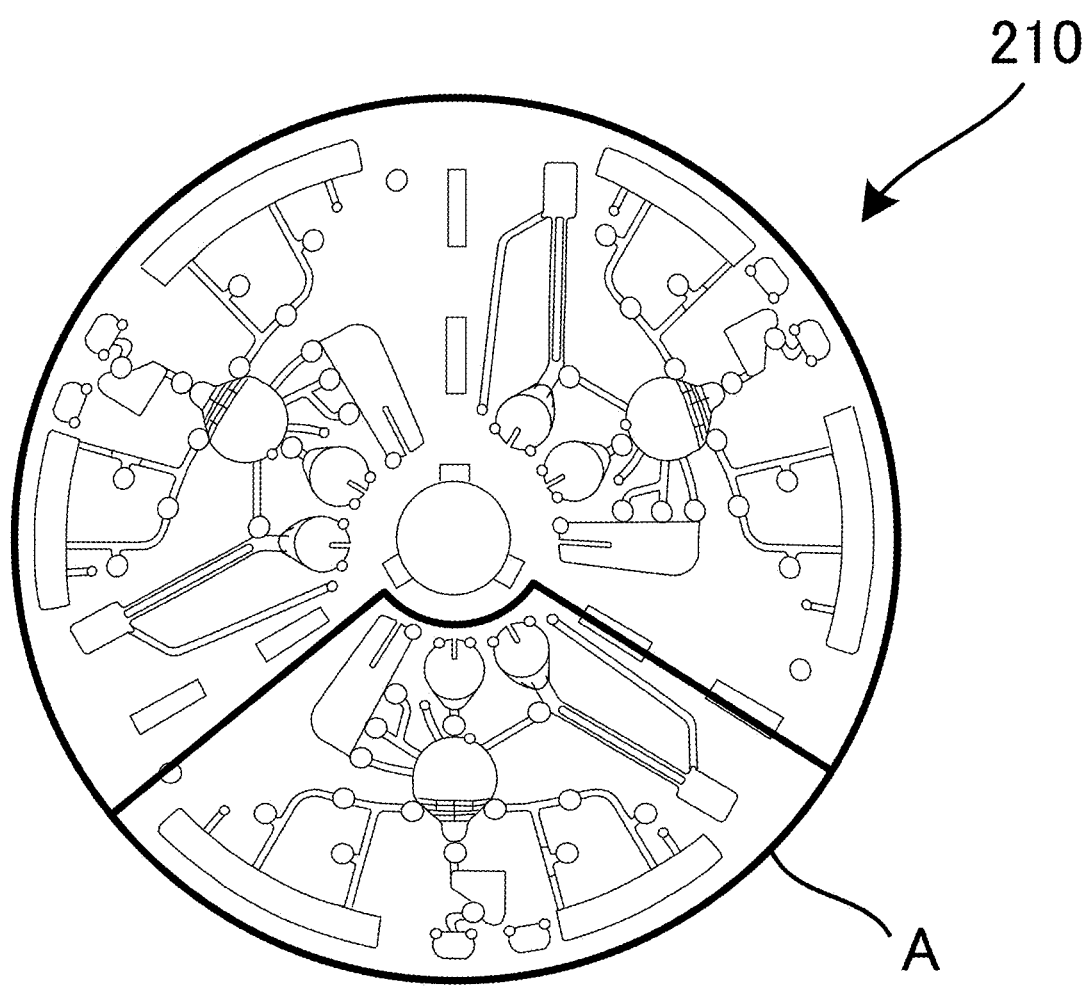
FIG. 2A is a schematic view illustrating an example of an existing analyzing apparatus.
Figure 2B:
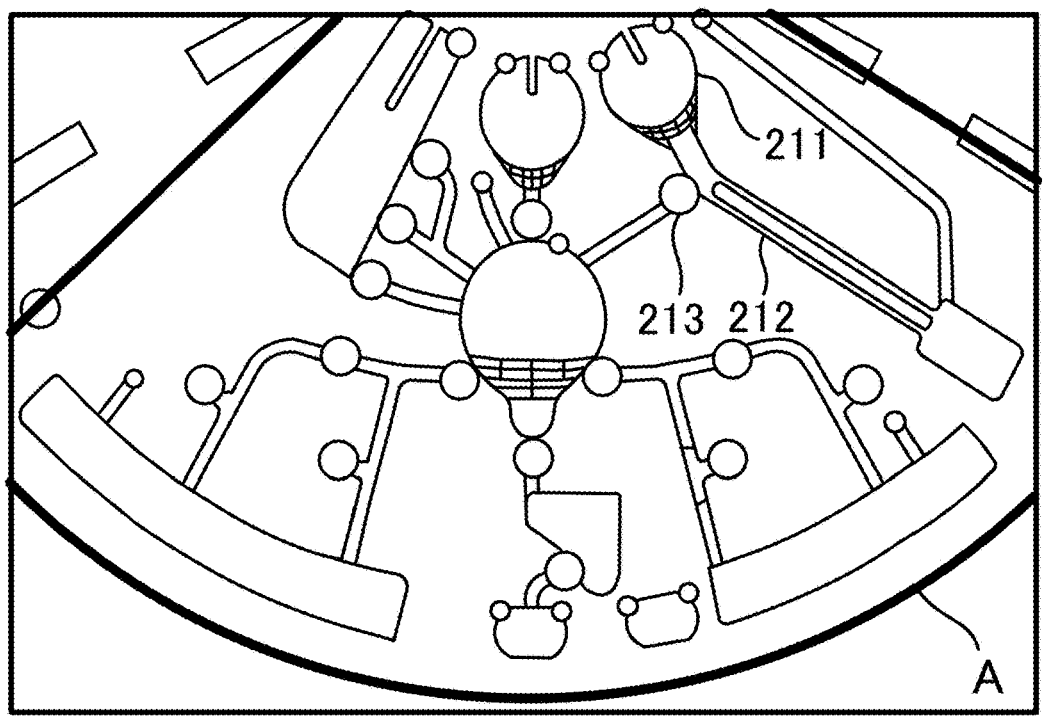
FIG. 2B is an enlarged view of a section A of FIG. 2A.

DESCRIPTION OF EMBODIMENTS (Separating Apparatus and Separating Method)

A separating apparatus of the present invention includes a separating unit and a transfer mechanism, preferably includes a storing unit, and further includes other units as needed.

A separating method of the present invention includes a separating step and a transferring step, preferably includes a storing step, and further includes other steps as needed.

The separating method of the present invention can be performed by the separating apparatus of the present invention. The separating step can be performed by the separating unit. The transferring step can be performed by the transfer mechanism. The storing step can be performed by the storing unit. The other steps can be performed by the other units.

If only mounted with a simple time adjusting mechanism, the separating apparatus of the present invention can be controlled even in steady rotation without, for example, a valve or an electromagnetic valve halfway on the flow path, and can separate a separation target with an extremely high purity from a fluid sample containing two or more components immiscible with each other and having different specific gravities.

With only a simple time adjusting mechanism, the separating method of the present invention can have control even in steady rotation without, for example, a valve or an electromagnetic valve halfway on the flow path, and can separate a separation target with an extremely high purity from a fluid sample containing two or more components having different specific gravities.

The time adjusting mechanism is not particularly limited and may be appropriately selected depending on the intended purpose, so long as the time adjusting mechanism can adjust the time of a fluid sample or a pressurizing medium. Examples of the time adjusting mechanism include adjustment of the shape, structure, length, and size of the flow path, a relay chamber, and a siphon structure.

<Separating Step and Separating Unit>

The separating step is a step of applying an external force to a fluid sample containing two or more components immiscible with each other and having different specific gravities to separate the fluid sample into a separation target and a non-separation target, and is performed by the separating unit.

The fluid sample is not particularly limited and may be appropriately selected depending on the intended purpose so long as the fluid sample contains two or more components immiscible with each other and having different specific gravities. Examples of the fluid sample include a sample formed of a solid and a liquid immiscible with each other and having different specific gravities, a sample formed of a liquid and a liquid immiscible with each other and having different specific gravities, a sample formed of a gas and a gas immiscible with each other and having different specific gravities, a sample formed of a solid and a gas immiscible with each other and having different specific gravities, a sample formed of a liquid and a gas immiscible with each other and having different specific gravities, and a sample formed of a liquid and a gas immiscible with each other and having different specific gravities. Among these samples, a sample formed of a solid and a liquid immiscible with each other and having different specific gravities and a fluid sample formed of a liquid and a liquid immiscible with each other and having different specific gravities are preferable.

Example of the sample formed of a solid and a liquid immiscible with each other and having different specific gravities include biological samples such as blood, saliva, gastric juice, bile, and urine.

Examples of the fluid sample formed of a liquid and a liquid immiscible with each other and having different specific gravities include liquid seasonings such as dressings, and samples formed of oils mixed in water.

Examples of the sample formed of a liquid and a gas immiscible with each other and having different specific gravities include separation of, for example, noble gases.

It is preferable that the fluid sample formed of a liquid and a liquid immiscible with each other and having different specific gravities contain two or more components.

Figure 3:
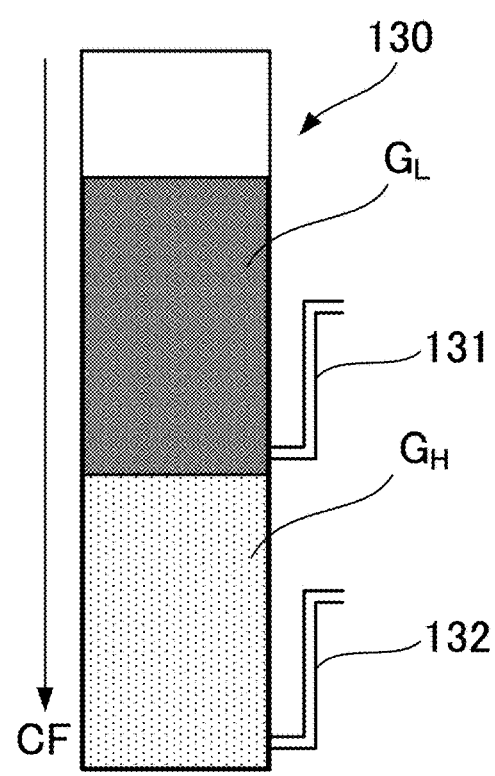
FIG. 3 is a view illustrating an example of a separated state of a fluid sample containing two components immiscible with each other and having different specific gravities.

When the fluid sample is a sample formed of two components, namely a component having a high specific gravity and a component having a low specific gravity, as illustrated in FIG. 3, the fluid sample can be separated into a component $G_L$ having a low specific gravity and a component $G_H$ having a high specific gravity in a separating chamber 130 in response to application of an external force CF to the fluid sample in the separating chamber 130 in the direction of the arrow. The component $G_L$ having a low specific gravity can be taken out from a flow path 131. The component $G_H$ having a high specific gravity can be taken out from a flow path 132.

Figure 4:
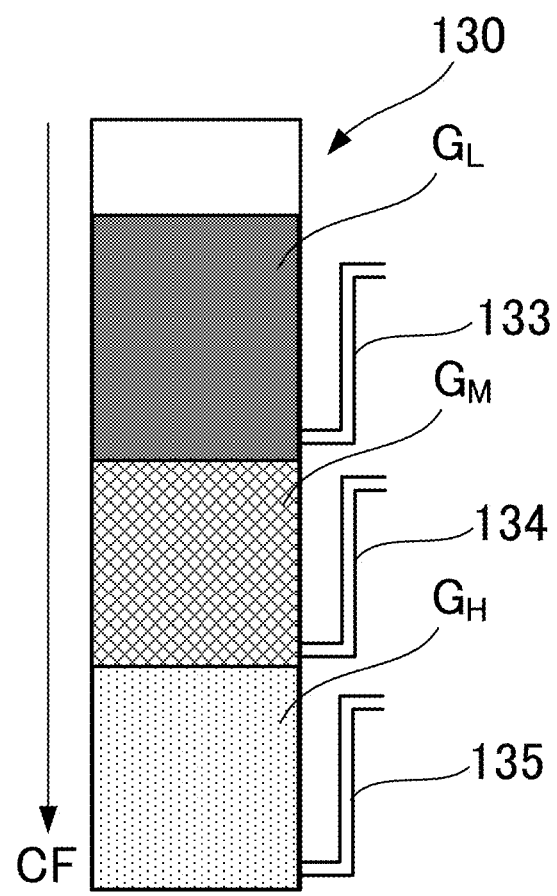
FIG. 4 is a view illustrating an example of a separated state of a fluid sample containing three components immiscible with one another and having different specific gravities.

When the fluid sample is a sample formed of three components, namely a component having a high specific gravity, a component having a middle specific gravity, and a component having a low specific gravity, as illustrated in FIG. 4, the fluid sample can be separated into a component $G_L$ having a low specific gravity, a component $G_M$ having a middle specific gravity, and a component $G_H$ having a high specific gravity in a separating chamber 130 in response to application of an external force CF to the fluid sample in the separating chamber 130 in the direction of the arrow. The component $G_L$ having a low specific gravity can be taken out from a flow path 133. The component $G_M$ having a middle specific gravity can be taken out from a flow path 134. The component $G_H$ having a high specific gravity can be taken out from a flow path 135.

The fluid sample containing two or more components immiscible with each other and having different specific gravities is not particularly limited and may be appropriately selected depending on the intended purpose. Examples of the fluid sample include: biological samples such as blood, saliva, gastric juice, bile, and urine; solutions containing microorganisms, animal cells, and plant cells; environmental samples such as seawater, inland water, soil, riverbed soil, lake sediment, marine sediment, and wastewater; liquid seasonings such as dressings; and various reagents, buffers, cleaning water, and cleaning gases. Among these fluid samples, blood is typically used as samples of biomarker analyses.

Blood contains blood plasma as a liquid component, and, for example, blood corpuscles and platelets as solid components. Examples of blood corpuscles include red corpuscles and white corpuscles.

The ratio of the solid components in the blood can be obtained from hematocrit value of the blood. The hematocrit value of the blood is typically from 40% through 60%.

The external force is not particularly limited and may be appropriately selected depending on the intended purpose. Examples of the external force include centrifugal force, gravity, magnetic force, static electricity, and pressing force.

Among these external forces, a centrifugal force generated by rotating a rotating body, on which the separating apparatus is mounted, about a rotation axis position (reference point) is preferable.

When the external force is applied, a force for flowing a pressurizing medium through a pressurizing medium chamber and a flow path, and a force for separating a fluid sample containing two or more components immiscible with each other and having different specific gravities into a separation target and a non-separation target are generated.

When an external force is applied to the separating apparatus, a force for flowing the fluid sample in the separating apparatus through a chamber or a flow path is generated. In the following description, the upstream side in the direction in which an external force is applied is simply referred to as "upstream side" or "upper portion" of each unit and the downstream side is simply referred to as "downstream side" or "lower portion" or "bottom portion" of each unit.

When the external force is a centrifugal force, for example, a disk-shaped rotating body on which the separating apparatus is mounted may be rotated, in order for a centrifugal force to be applied to the separating apparatus and a force for flowing a fluid sample to be generated.

When the external force is the gravity, for example, the separating apparatus may be a columnar body having a structure enabling the fluid sample to be transferred from one end to the other end to be dispensed, and during dispensing, one end may be brought to a higher position than the other end in order for a force for flowing a fluid sample to be generated.

When the external force is a magnetic force, for example, the N pole may be positioned at the upstream side of the separating apparatus and the S pole may be positioned at the downstream side, in order for a force for flowing a fluid sample having magnetism to be generated.

When the external force is static electricity, for example, an electrode plate charged with positive charges may be positioned at the upstream side of the separating apparatus and an electrode plate charged with negative charges may be positioned at the downstream side, in order for a force for flowing the fluid sample having negative charges to be generated.

When the external force is a pressing force, for example, a chamber charged with a fluid sample and provided in the separating apparatus may be pressed with, for example, an actuator, in order for a force for flowing the fluid sample to be generated.

The separating unit is not particularly limited and may be appropriately selected depending on the intended purpose. It is preferable that the separating unit include a separating chamber.

For example, the size, shape, structure, and number of the separating chamber are not particularly limited and may be appropriately selected depending on the intended purpose, so long as the separating chamber can separate a fluid sample into a separation target and a non-separation target in response to application of a centrifugal force serving as an external force to the fluid sample in the separating chamber.

The separating chamber serving as the separating unit and a flow path to be joined to the separating chamber are not particularly limited and may be appropriately selected depending on the intended purpose. For example, the separating chamber and the flow path can be produced by a lithography technique using a material such as polydimethylsiloxane (PDMS).

No matter what material is used to produce the separating unit, the separating unit more or less undergoes shape change due to changes in the external force and pressure. Therefore, it is preferable to use a material having a high stiffness. Examples of the material having a high stiffness include polymethyl methacrylate (PMMA), polycarbonate (PC), polystyrene (PS), and cycloolefin (COP). Using any of these materials, the separating unit can be produced by a common molding method such as injection molding.

For suppressing elastic deformation, it is preferable to shape the separating chamber and the flow path joined to the separating chamber in a manner to have a cross-sectional shape having an aspect ratio close to 1, such as a square and a circle. This makes it possible to suppress fluctuation of a liquid surface position due to deformation of the separating chamber and the flow path joined to the separating chamber.

Figure 5:
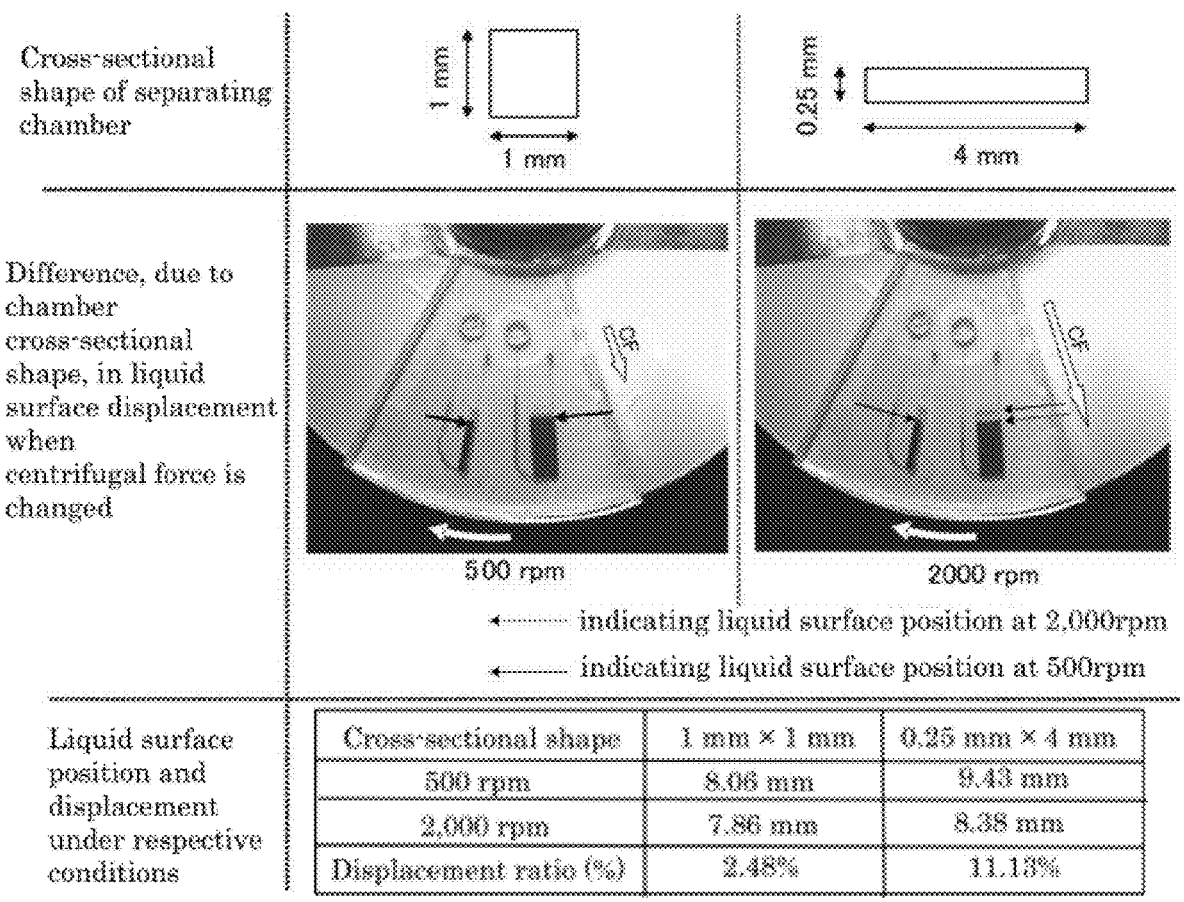
FIG. 5 is a diagram illustrating a relationship among the cross-sectional shape of a separating chamber, liquid surface displacement, and a liquid surface position when polydimethylsiloxane (PDMS) is used as the material of the separating chamber.

Here, as illustrated in FIG. 5, by providing the separating chamber and the flow path joined to the separating chamber with a cross-sectional shape having an aspect ratio close to 1, such as a square, it is possible to better prevent cross-sectional shape deformation due to change in the centrifugal force and to better suppress liquid surface displacement, compared with an elongate cross-sectional shape having a large aspect ratio.

In order to apply a centrifugal force to the separating chamber efficiently, t is preferable to dispose the separating chamber on a rotatable rotating body. In this case, the transfer mechanism may also be mounted on the rotating body together, or the transfer mechanism may be provided as a separate body.

The rotating body is not particularly limited and may be appropriately selected depending on the intended purpose. For example, a discus disk is preferable. As the discus disk, for example, the similar bodies to compact discs (CD) and digital video discs (DVD) can be used.

It is possible to apply a centrifugal force to the separating chamber by mounting the separating chamber on the rotating body and rotating the rotating body about the rotating axis position. The rotation number of the rotating body is not particularly limited and may be appropriately selected depending on the intended purpose so long as it is a desired rotation number. A constant rotation number is preferable because there is no need for adjustment control for increasing or reducing the rotation number.

By mounting a plurality of separating chambers on the rotating body, it is possible to perform a plurality of separation operations at a time efficiently.

By setting the separating apparatus and a testing apparatus on the rotating body in a joined manner, it is possible to perform a process from separation of a fluid sample to testing of a separated separation target all at a time automatically. In this case, the testing apparatus can test the separation target in a state that the same external force as the external force applied to the separating unit is applied to the testing apparatus.

<Transferring Step and Transfer Mechanism>

The transferring step is a step of applying a pressure to the separation target separated in the separating step to transfer the separation target, and is performed by the transfer mechanism.

The pressure is not particularly limited and may be appropriately selected depending on the intended purpose. It is preferable to apply the pressure in a manner to pressurize the separation target separated. This makes it possible to suppress generation of air bubbles and expansion of the air bubbles in the separation target, and allow the separation target to be tested accurately by a testing unit.

The transfer mechanism can transfer a pressurizing medium into the separating chamber and transfer the separation target in the separating chamber to outside the separating chamber by the pressure of the pressurizing medium.

The pressurizing medium is preferably at least one selected from liquids and gases, and immiscible with the separation target.

The liquids are not particularly limited and may be appropriately selected depending on the intended purpose. Examples of the liquids include hydrophilic solvents such as water and alcohols, and oils. Examples of the oils include liquid paraffin and mineral oils.

The gases are not particularly limited and may be appropriately selected depending on the intended purpose. Examples of the gases include air, and inert gases such as nitrogen and argon. For example, ammonia having an extremely high solubility with the sample cannot be used.

The transfer mechanism configured to transfer the pressurizing medium into the separating chamber is not particularly limited and may be appropriately selected depending on the intended purpose. It is preferable that the transfer mechanism include at least one of a pressurizing medium chamber, a bent flow path, and a siphon structure. With the transfer mechanism, it is possible to adequately adjust the time taken to transfer the pressurizing medium into the separating chamber, and, for example, to adjust the pressurizing medium to be transferred into the separating chamber after separation into the separation target and the non-separation target is completed in the separating chamber.

The bent flow path is not particularly limited and may be appropriately selected depending on the intended purpose. Examples of the bent flow path include a "winding (hairpin curve) shape", a "doglegged shape", a "squared-U shape", an "S-letter shape", a "Y-letter shape", a "T-letter shape", and a "cruciform shape", or combinations of these shapes.

With a bent flow path that has a longer flow path length than a linear flow path, it is possible to adjust the pressurizing medium to take a long time to pass through the flow path.

The pressurizing medium chamber is a chamber that is provided in front (upstream) of the separating chamber, is joined to the separating chamber through the bent flow path and a flow path, and is configured to temporarily store the pressurizing medium.

By providing the pressurizing medium chamber in front (upstream) of the separating chamber, it is possible to earn a time for transferring the pressurizing medium into the separating chamber.

For example, the size, shape, structure, and number of the pressurizing medium chamber are not particularly limited and may be appropriately selected depending on the intended purpose.

It is preferable to provide a flow path that joins the pressurizing medium chamber to the separating chamber with a siphon structure. With a siphon structure, it is possible to smoothly transfer the pressurizing medium into the separating chamber when the amount of the pressurizing medium injected into the pressurizing medium chamber becomes higher than or equal to a predetermined amount.

The siphon structure is not particularly limited and may be appropriately selected depending on the intended purpose so long as it is a structure capable of continuously transferring the pressurizing medium into the pressurizing chamber by the siphon principle. Examples of the siphon structure include a U-letter shaped structure provided on the flow path that joins the pressurizing medium chamber to the separating chamber.

Moreover, it is preferable that the transfer mechanism include an internal pressure adjusting chamber provided between the pressurizing medium chamber and the separating chamber and configured to transfer the separation target in the separating chamber to outside the separating chamber by a pressure generated when the pressurizing medium is injected.

With the internal pressure adjusting chamber serving as the transfer mechanism, a gas in the internal pressure adjusting chamber can be used as the pressurizing medium. Because a gas does not become compatible with a fluid sample containing two or more components immiscible with each other and having different specific gravities, a gas is preferable as the pressurizing medium. For example, when a liquid sample containing a solid is blood, water can also be used in addition to oils, as the pressurizing medium to be introduced into the pressurizing medium chamber.

For example, the size, shape, structure, and number of the internal pressure adjusting chamber are not particularly limited and may be appropriately selected depending on the intended purpose.

The time for which, for example, the pressurizing medium chamber, the bent flow path, the siphon structure, and the internal pressure adjusting chamber serving as the transfer mechanism pressurize the separation target can be appropriately designed by total evaluation and calculation of the time at which separation is completed, and of a centrifugal force applied to the pressurizing medium, obtained based on, for example, the length of the flow path, the diameter of the flow path, the viscosity of the pressurizing medium, the location of the separating apparatus on the rotating body (the distance from the rotation axis position of the rotating body), the rotation number of the rotating body, and the density of the pressurizing medium.

For example, the pressurizing medium chamber, the bent flow path, the siphon structure, and the internal pressure adjusting chamber serving as the transfer mechanism are not particularly limited and may be appropriately selected depending on the intended purpose, and, for example, can be produced using the same material and the same producing method as used for the separating unit.

<Storing Step and Storing Unit>

The storing step is a step of storing the separation target transferred in the transferring step, and is performed by the storing unit.

For example, the size, shape, structure, and number of the storing unit are not particularly limited and may be appropriately selected depending on the intended purpose.

In order to transfer the separation target separated in the separating unit into the storing unit without contamination of, for example, the non-separation target, it is preferable to join the separating chamber to the storing unit by means of a separation target transferring flow path that is opened at a position at which the separation target in the separating chamber is present. For example, when blood is used as a fluid sample and blood plasma is transferred as the separation target into the storing unit, an extraction port of the separation target transferring flow path can be provided at a position at which blood corpuscles, which are a non-separation target, may not mix, based on the hematocrit value of the blood.

In terms of preventing contamination of the non-separation target, it is preferable to optimize the shape of the separation target transferring flow path and optimize the contact angle of the separation target transferring flow path with the separating chamber when joining the separating chamber to the storing unit through the separation target transferring flow path opened at the position at which the separation target in the separating chamber is present.

Figure 6:
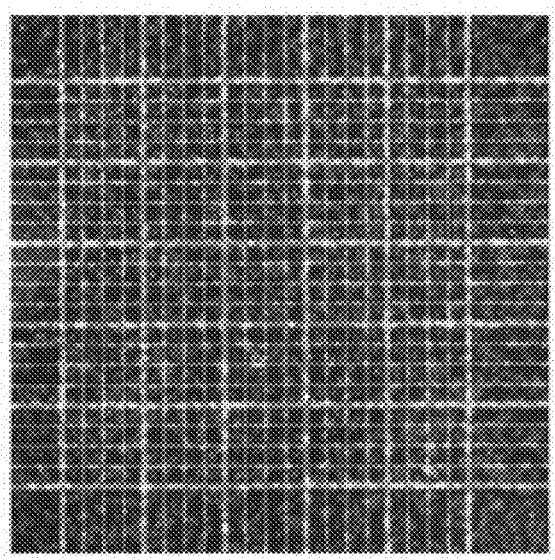
FIG. 6 is a view illustrating a counted state, on a hemocytometer, of 200-fold diluted blood as the initial concentration of whole blood before blood separation by a separating apparatus.

FIG. 6 illustrates hemocytometer counting of 200-fold diluted blood as the initial concentration of whole blood before blood separation by the separating apparatus, indicating that the number of blood corpuscles is $4.05 \times 10^6$ (RBCs/microliter).

Figure 7A:
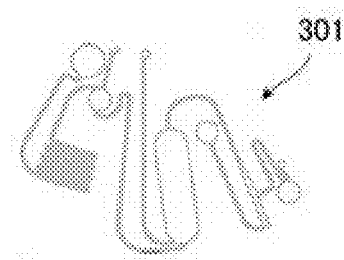
FIG. 7A is a schematic view of a separating apparatus.
Figure 7B:
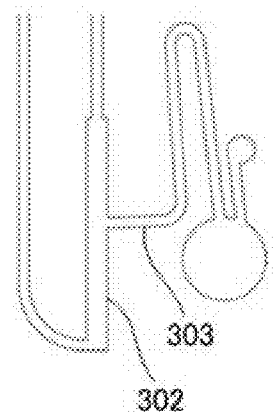
FIG. 7B is an enlarged view of a joining part between a separating chamber and a separation target transferring flow path.
Figure 7C:
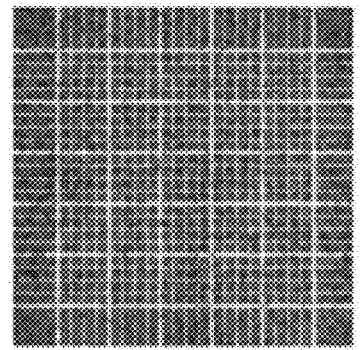
FIG. 7C is a view illustrating a counted state of extracted blood plasma on a hemocytometer.

FIG. 7A is a schematic view of a separating apparatus 301. FIG. 7B is an enlarged view of a joining part between a separating chamber 302 and a separation target transferring flow path 303. As illustrated in FIG. 7B, blood plasma is extracted from two-fold diluted blood using the separating apparatus 301 including a separation target transferring flow path 303 having a L-letter shape, and the obtained blood plasma is counted on a hemocytometer without dilution. As a result, the number of blood corpuscles mixed in the extracted blood plasma is $0.116 \times 10^6$ (RBCs/microliter) (see FIG. 7C).

Figure 8A:
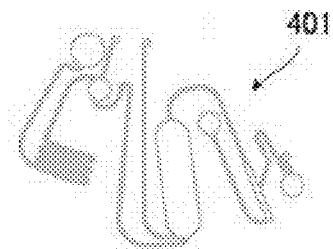
FIG. 8A is a schematic view of a separating apparatus.
Figure 8B:
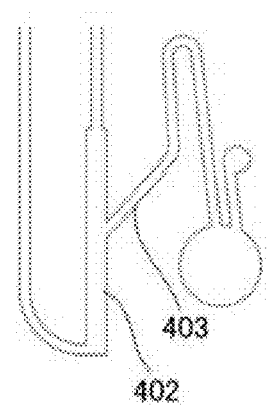
FIG. 8B is an enlarged view of a joining part between a separating chamber and a separation target transferring flow path.
Figure 8C:
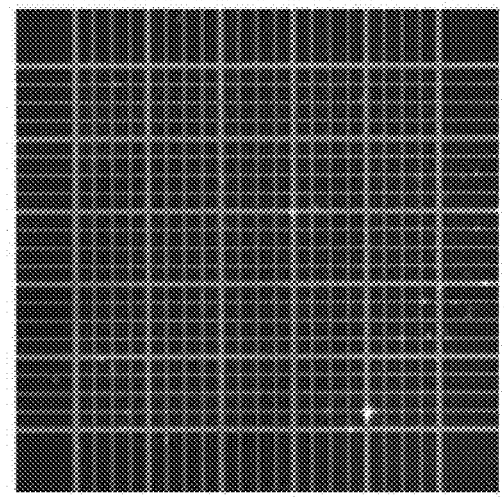
FIG. 8C is a view illustrating a counted state of extracted blood plasma on a hemocytometer.

Next, FIG. 8A is a schematic view of a separating apparatus 401. FIG. 8B is an enlarged view of a joining part between a separating chamber 402 and a separation target transferring flow path 403. As illustrated in FIG. 8B, blood plasma is extracted from two-fold diluted blood using the separating apparatus 401 including a separation target transferring flow path 403 having a V-letter shape, and the obtained blood plasma is counted on a hemocytometer without dilution. As a result, the number of blood corpuscles mixed in the extracted blood plasma is $0.0006 \times 10^6$ (RBCs/micrometer) (see FIG. 8C).

Figure 9:
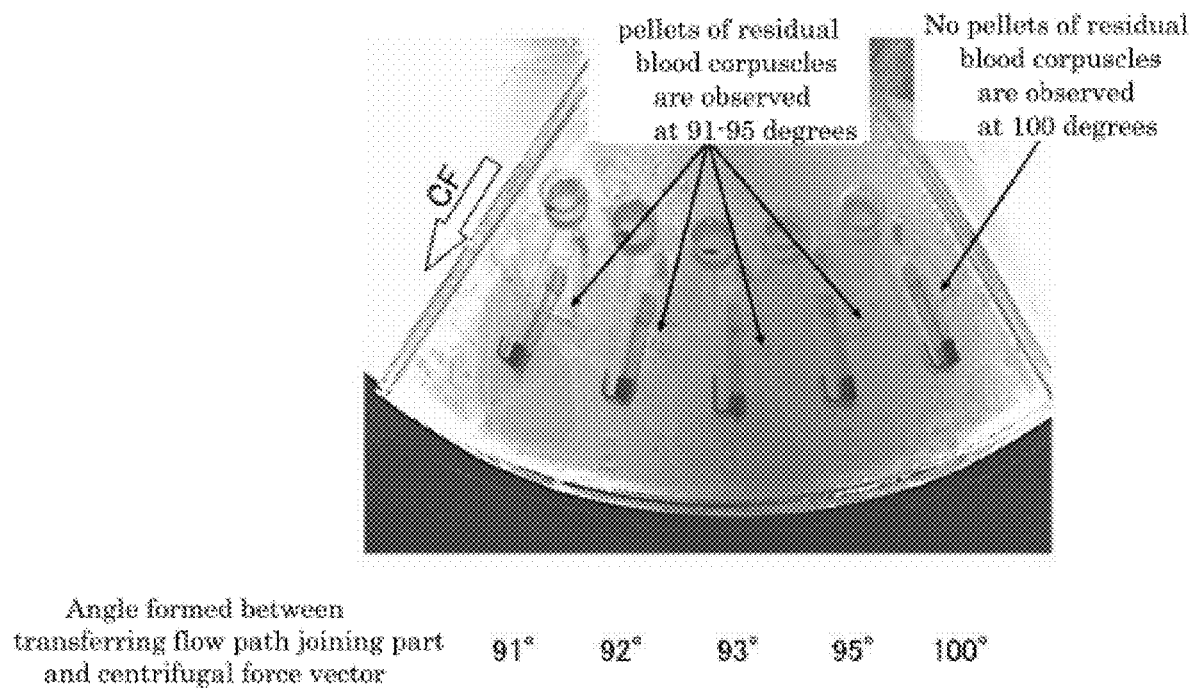
FIG. 9 is a view illustrating a relationship between a joining angle of a transferring flow path and an effect of preventing remaining of blood corpuscles.

As illustrated in FIG. 9, presence or absence of remaining blood corpuscles is evaluated with the angle between a centrifugal force vector CF and the joining part between the separating chamber and the separation target transferring flow changed among 91 degrees, 92 degrees, 93 degrees, 95 degrees, and 100 degrees. As a result, when the contact angle of the transferring flow path is from 91 degrees through 95 degrees, pellets of remaining blood corpuscles are observed. On the other hand, when the contact angle of the transferring flow path is 100 degrees, no pellets of remaining blood corpuscles are observed.

Accordingly, when the contact angle of the transferring flow path is 100 degrees or greater with respect to the centrifugal force vector CF, an effect of preventing remaining of blood corpuscles is observed.

The separation target stored in the storing unit is conveyed to a testing unit through a flow path that joins the storing unit to a testing apparatus, and tested by a testing unit.

The storing unit and the separation target transferring flow path are not particularly limited and may be appropriately selected depending on the intended purpose. For example, the storing unit and the separation target transferring flow path may be produced using the same material and the same producing method as used for the separating unit.

<Other Units>

Examples of the other units include a vent, a metering unit, and a control unit.

For example, the vent is provided in a manner to be joined to each of the chambers such as the separating chamber, the storing unit, the pressurizing medium chamber, and the pressure adjusting chamber. With a vent provided to, for example, the separating chamber, the separating chamber can be efficiently evacuated of air.

The metering unit may be, for example, as illustrated in FIG. 10A and FIG. 10B.

When the metering unit 140 is provided inclined with respect to a centrifugal force CF as illustrated in FIG. 10A and FIG. 10B, separation can be accelerated through a boycott effect. In FIG. 10A, the reference numeral 64 denotes a sample introducing chamber and the reference numeral 66 denotes a storing chamber.

Moreover, when the metering unit 140 is provided inclined with respect to a centrifugal force CF, blood plasma of a defined amount can be extracted even if the amount of blood injected into the sample introducing chamber 64 is not accurate.

As the control unit, for example, a simple controller such as a motor that makes a steady rotation can be used.

The structure of the separating apparatus is not particularly limited and may be appropriately selected depending on the intended purpose. For example, the separating unit, the transfer mechanism, and the storing unit may be integrated, or at least any of them may be a separate body, or all of them may be separate bodies.

The shape of the separating apparatus is not particularly limited and may be appropriately selected depending on the intended purpose. When an external force is a centrifugal force, a shape that can be disposed on a rotatable rotating body is preferable, and, for example, a flat plate shape and a disk shape are more preferable. The shape of the separating apparatus may be a shape (so-called "fan shape") cut out by a predetermined angle from the center of a disk-shaped circle.

Embodiments of the separating apparatus of the present invention will be described with reference to the drawings.

First Embodiment of Separating Apparatus

Figure 11:
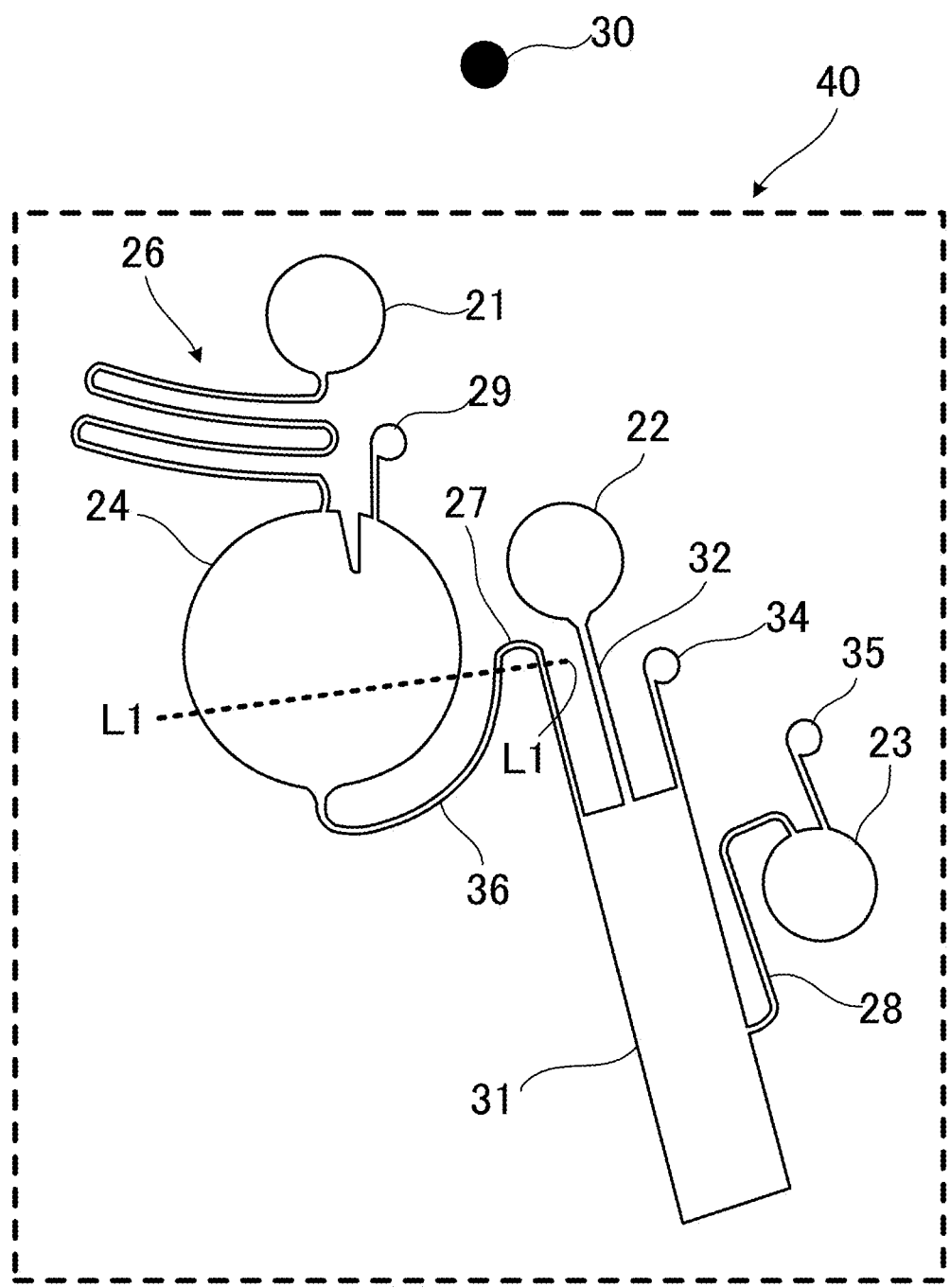
FIG. 11 is a view illustrating an example of a separating apparatus of a first embodiment.

FIG. 11 is a plan view of the separating apparatus 40 of the first embodiment. The separating apparatus 40 of the first embodiment illustrated in FIG. 11 includes a pressurizing medium introducing chamber 21, a sample introducing chamber 22, a pressurizing medium chamber 24, a separating chamber 31 as a separating unit, and a storing chamber 23 as a storing unit.

There is a bent flow path 26 between the pressuring medium introducing chamber 21 and the pressurizing medium chamber 24. There is a relay flow path 36 between the pressurizing medium chamber 24 and the separating chamber 31, and a siphon structure 27 is provided halfway on the relay flow path.

By the functioning of the bent flow path 26, the pressurizing medium chamber 24, the relay flow path 36, and the siphon structure 27 as a pressurizing medium transfer mechanism, a pressure is applied to the separation target separated in the separating chamber 31, so that the separation target may be stored in the storing chamber 23.

A sample transferring flow path 32 configured to transfer a fluid sample introduced in the sample introducing chamber 22 and containing two or more components immiscible with each other and having different specific gravities, and to the separating chamber 31 is provided between the sample introducing chamber 22 and the separating chamber 31.

A separation target transferring flow path 28 configured to transfer the separation target separated in the separating chamber 31 to the storing chamber 23 is provided between the separating chamber 31 and the storing chamber 23.

All of the flow paths 26, 36, 32, and 28 are formed of a thin tube. At least one of the length, girth, and shape of the thin tube may be varied between the flow paths.

In FIG. 11, the reference numerals 29, 34, and 35 denote vents configured to evacuate the respective chambers of air. In FIG. 11, the reference numeral 30 denotes a rotation axis position (reference point).

A pressurizing medium is introduced in a predetermined amount in the pressurizing medium introducing chamber 21. The pressurizing medium is preferably at least any one selected from liquids and gases and immiscible with the separation target.

A fluid sample containing two or more components immiscible with each other and having different specific gravities is introduced in a predetermined amount into the sample introducing chamber 22.

The fluid sample introduced into the sample introducing chamber 22 and containing two or more components immiscible with each other and having different specific gravities is transferred to the separating chamber 31 in response to application of an external force. Subsequently, the fluid sample containing two or more components immiscible with each other and having different specific gravities is separated in the separating chamber 31 into a separation target and a non-separation target in response to application of an external force.

The pressurizing medium is transferred into the separating chamber 31 by the bent flow path 26, the pressurizing medium chamber 24, the relay flow path 36, and the siphon structure 27 that serve as the transfer mechanism. By the pressure of the pressurizing medium, the separation target separated in the separating chamber 31 is transferred to the storing chamber 23. Here, the pressurizing medium and the fluid sample containing two or more components immiscible with each other and having different specific gravities contact each other in the separating chamber 31. Therefore, it is preferable that the pressurizing medium and the fluid sample be immiscible with each other. The separation target stored in the storing chamber 23 is used as a sample of a testing apparatus.

As illustrated in FIG. 12A to FIG. 12E, blood serving as a fluid sample containing two or more components immiscible with each other and having different specific gravities is separated using a blood separating apparatus serving as the separating apparatus 40 of the first embodiment.

Figure 12A:
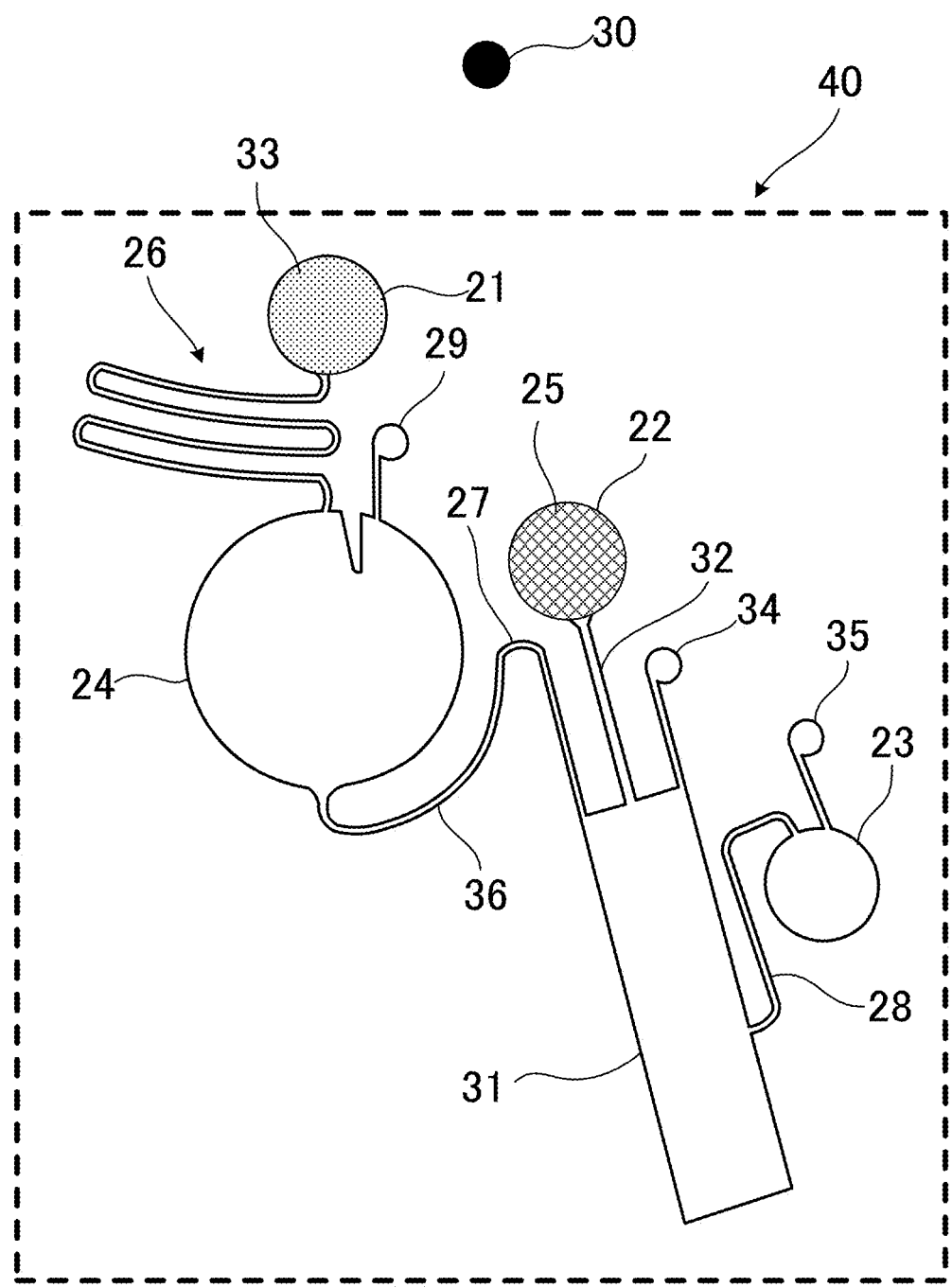
FIG. 12A is a view illustrating an example of a separating method of the present invention using a separating apparatus of a first embodiment.

As illustrated in FIG. 12A, a mineral oil serving as a pressurizing medium is introduced in an amount of 5 microliters into the pressurizing medium introducing chamber 21 using a pipette.

Meanwhile, the blood serving as the fluid sample containing two or more components immiscible with each other and having different specific gravities is introduced in an amount of 10 microliters into the sample introducing chamber 22 using a pipette.

Figure 13:
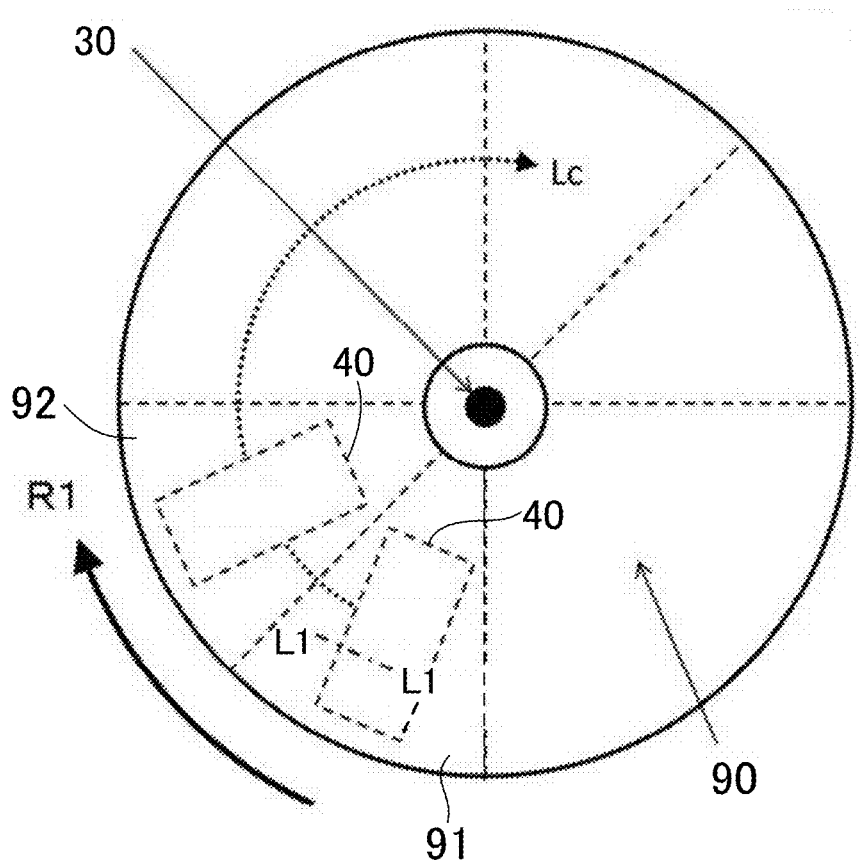
FIG. 13 is a view illustrating an example of a state of centrifugal force application by rotation of a separating apparatus set on a disk.

Next, as illustrated in FIG. 13, the separating chamber 40 is mounted on a disk 90 and rotated in a rotation direction R1 at 1,500 rpm. This enables a centrifugal force CF to be applied to the blood 25 in the sample introducing chamber 22 and the oil 33 in the pressurizing medium introducing chamber 21 of the separating apparatus 40 illustrated in FIG. 11. The disk 90 has a hole in the center for receiving a rotation shaft of the disk driving apparatus. This hole corresponds to the rotation axis position 30 of the separating apparatus 40 (see FIG. 11).

As illustrated in FIG. 13, one separating apparatus 40 can be disposed on each section (91, 92, . . . ) of the disk 90, so a plurality of separating apparatuses 40 can be mounted.

Figure 14:
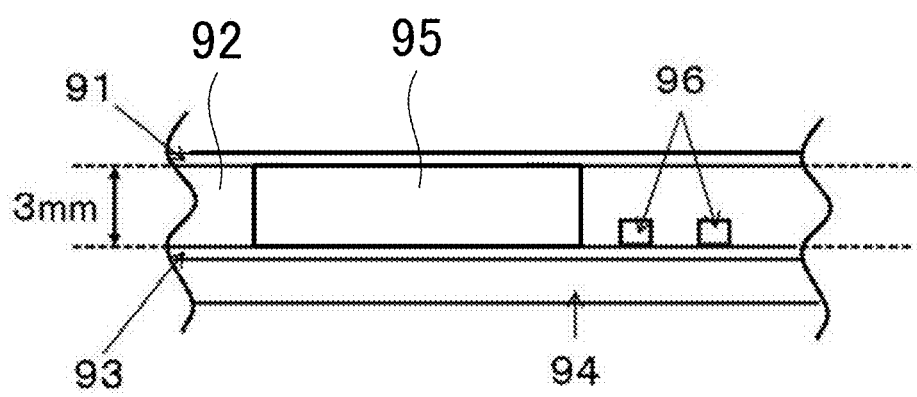
FIG. 14 is a cross-sectional view of FIG. 13 taken along a line L1-L1.

FIG. 14 illustrates a cross-sectional structure of the separating apparatus 40 mounted on the disk 90 taken along a line L1-L1. The line L1-L1 represents a cross section of the pressurizing medium chamber 24 and the siphon structure 27 formed on the relay flow path 36 of the separating apparatus 40 illustrated in FIG. 11. The reference numeral 94 denotes a base material. There is a polydimethylsiloxane (PDMS) sheet (PDMS sheet) 93 on the base material 94. A pressurizing medium chamber 95 and a thin tube 96 of the siphon structure are formed by a lithography technique in a PDMS layer 92 formed on the PDMS sheet 93. A cover layer 91 is provided on the PDMS layer 92. In this case, in order to reduce the influence of elasticity of the material, it is preferable that the cross-sectional shape of each chamber be a shape having an aspect ratio close to 1, such as a square and a circle. As a material having a higher stiffness, for example, PMMA, PC, PS, or COP may be used to produce, for example, reservoirs and flow paths by, for example, injection molding.

Figure 12B:
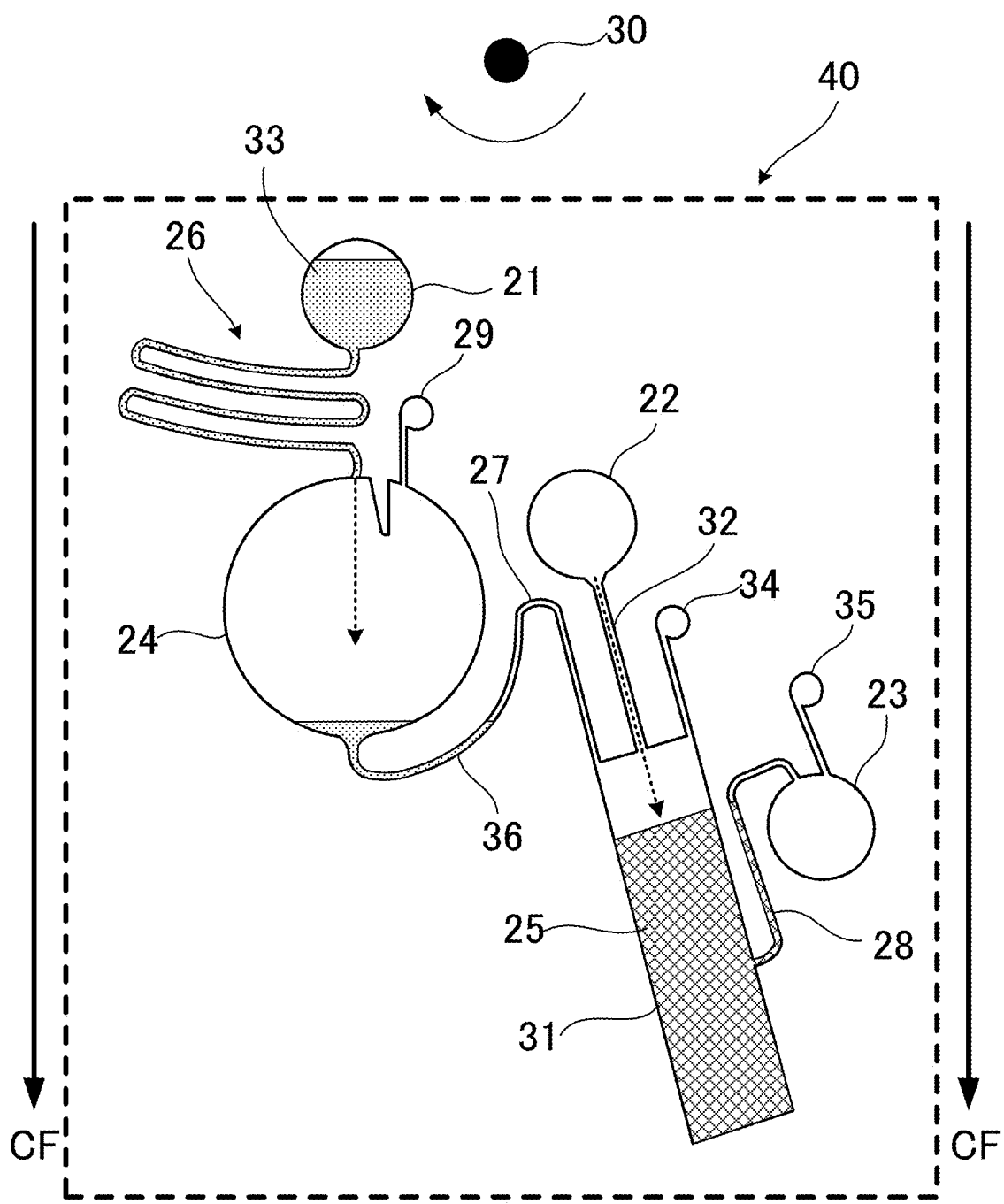
FIG. 12B is a view illustrating an example of a separating method of the present invention using a separating apparatus of a first embodiment.

Next, as illustrated in FIG. 12B, when a centrifugal force CF serving as an external force is applied, the oil 33 in the pressurizing medium introducing chamber 21 is injected into the pressurizing medium chamber 24 through the bent flow path 26. Here, because the pressurizing medium chamber 24 has a vent 29 communicating with the pressurizing medium chamber 24, the oil 33 is smoothly injected into the pressurizing medium chamber 24.

Meanwhile, when a centrifugal force CF serving as an external force is applied, the blood 25 in the sample introducing chamber 22 is injected into the separating chamber 31 through the sample transferring flow path 32. Here, because the separating chamber 31 has a vent 34 communicating with the separating chamber 31, the blood 25 is smoothly injected into the separating chamber 31.

Figure 12C:
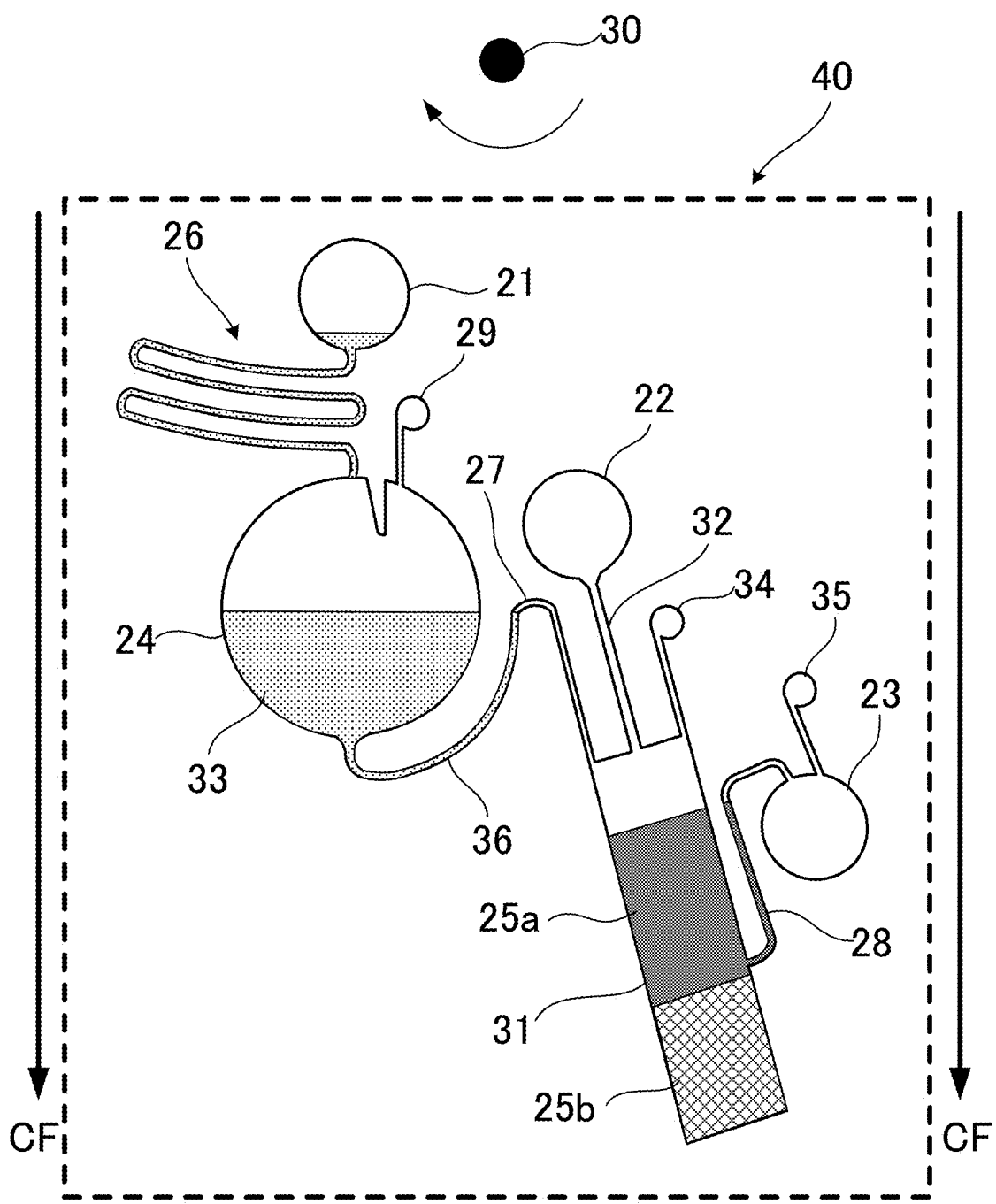
FIG. 12C is a view illustrating an example of a separating method of the present invention using a separating apparatus of a first embodiment.

Next, as illustrated in FIG. 12C, when a centrifugal force CF is applied for a predetermined period of time, the oil 33 in the pressurizing medium introducing chamber 21 is stored in the pressurizing medium chamber 24 to a predetermined amount through the bent flow path 26.

Meanwhile, when a centrifugal force CF is applied for a predetermined period of time, the blood 25 in the separating chamber 31 is separated in the separating chamber 31 into blood plasma 25a and blood corpuscles 25b.

Figure 12D:
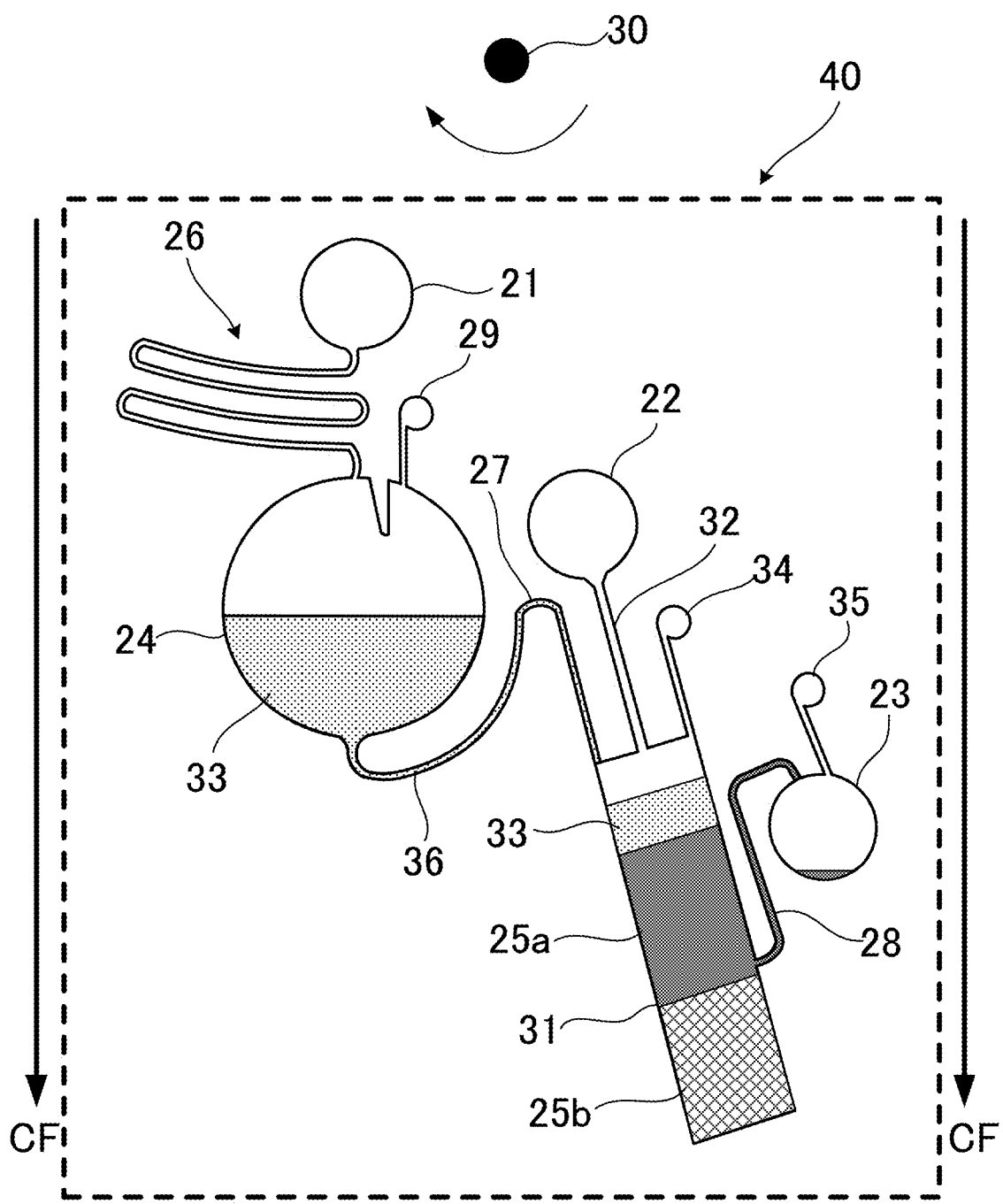
FIG. 12D is a view illustrating an example of a separating method of the present invention using a separating apparatus of a first embodiment.

Next, as illustrated in FIG. 12D, when a centrifugal force CF is further applied, the amount of the oil 33 stored in the pressurizing medium chamber 24 exceeds a predetermined amount. Then, by the siphon principle, the oil is injected into the separating chamber 31 through climbing up and down the U-letter-shaped siphon structure 27. Then, by the pressure of the oil 33, the blood plasma 25a, which is the separation target in the separating chamber 31, is transferred to the storing chamber 23 through the separation target transferring flow path 28. Here, because the storing chamber 23 has a vent 35 communicating with the storing chamber 23, the blood plasma 25a is smoothly injected into the storing chamber 23.

In the testing apparatus of the first embodiment, the oil 33 and the blood plasma 25a contact each other in the separating chamber 31 but are immiscible with each other. Therefore, the blood plasma 25, which is the separation target, is not contaminated by the oil 33.

The separation target transferring flow path 28 is joined in a manner to be opened at a position on the separating chamber 31 at which the blood plasma 25a is present at a separating chamber 31's side to the storing chamber 23.

Figure 12E:
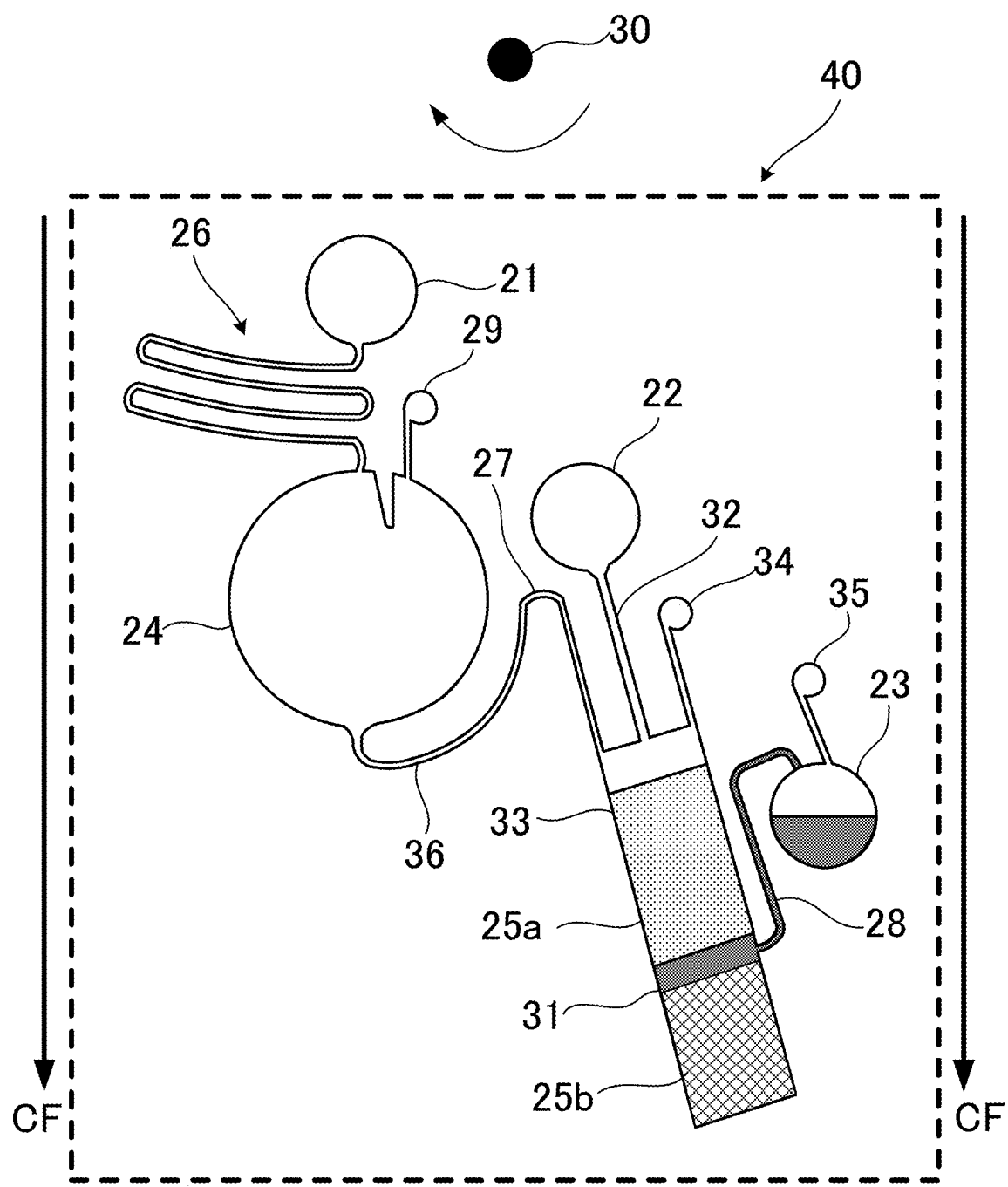
FIG. 12E is a view illustrating an example of a separating method of the present invention using a separating apparatus of a first embodiment.

Next, as illustrated in FIG. 12E, when a centrifugal force CF is further applied, the oil 33 is further injected into the separating chamber 31. By the pressure of the oil 33, most part of the blood plasma 25a in the separating chamber 31 is injected into the storing chamber 23 and stored. Through this, blood separation is completed.

In this way, with previous designing of the time taken for the oil 33 to be injected into the separating chamber 31, the blood separating apparatus serving as the separating apparatus of the first embodiment can adjust the pressure of the oil 33 to be applied to the blood plasma, which is the separation target, after blood separation is completed.

Second Embodiment of Separating Apparatus

Figure 15:
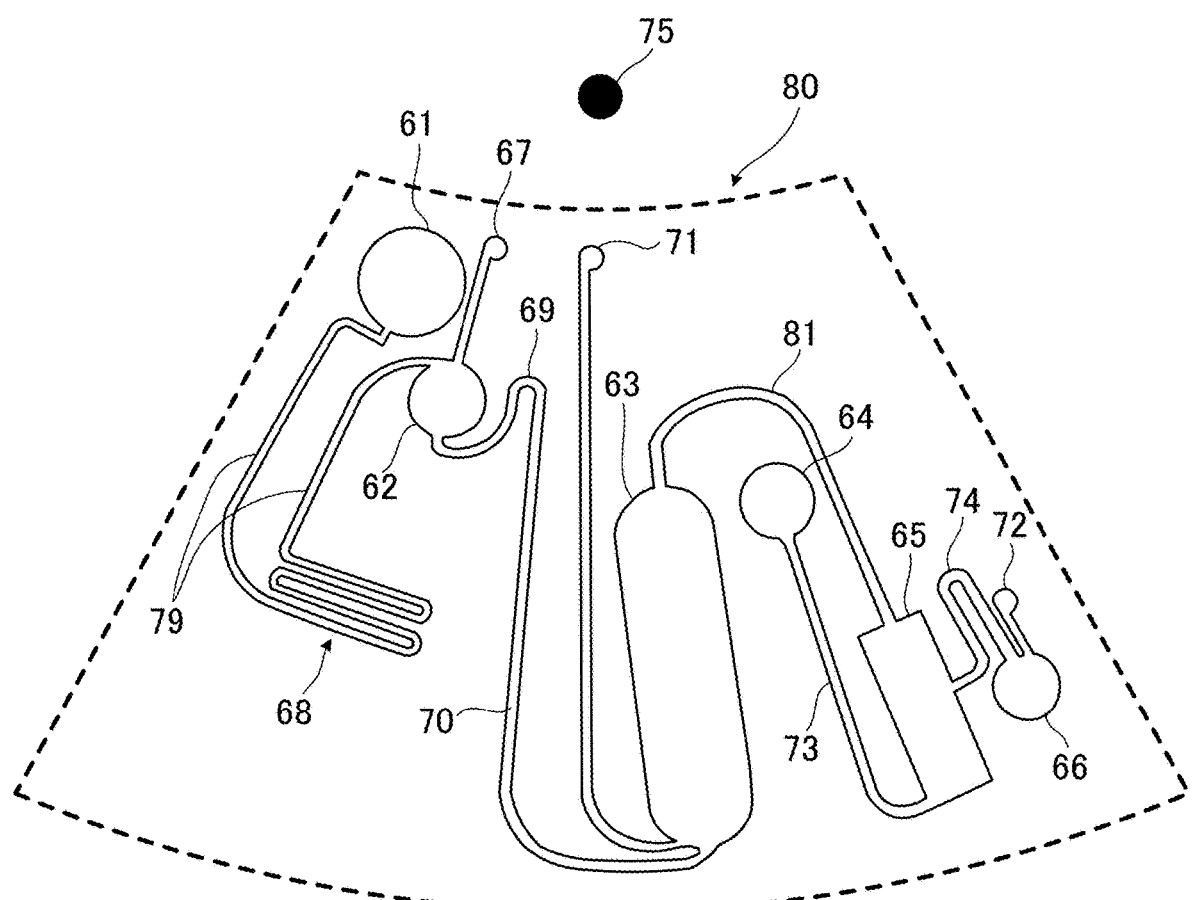
FIG. 15 is a view illustrating an example of a separating apparatus of a second embodiment.

FIG. 15 is a plan view illustrating an example of a separating apparatus 80 of the second embodiment. The separating apparatus 80 of the second embodiment illustrated in FIG. 15 has the same configuration as the separating apparatus 40 of the first embodiment illustrated in FIG. 11 except that there is an internal pressure adjusting chamber 63 between a pressurizing medium chamber 62 and a separating chamber 65 serving as the separating unit. Description of any components that are the same as those of the testing apparatus 18 of the first embodiment described above will be skipped.

The separating apparatus 80 of the second embodiment can use a pressurizing medium compatible with the separation target as the pressurizing medium to be introduced in a pressurizing medium introducing chamber 61, and has a wider selection of the pressurizing medium.

A sample transferring flow path 73 configured to transfer a fluid sample containing two or more components immiscible with each other and having different specific gravities to the separating chamber 65 is provided between a sample introducing chamber 64 and the separating chamber 65.

A separation target transferring flow path 74 configured to transfer the separation target separated in the separating chamber 65 to a storing chamber 66 is provided between the separating chamber 65 and the storing chamber 66.

The internal pressure adjusting chamber 63 is filled with air serving as a pressurizing medium, and communicates with the separating chamber 65 through an internal pressure adjusting flow path 81.

A bent flow path 68 is provided between the pressurizing medium introducing chamber 61 and the pressurizing medium chamber 62 through joining flow paths 79.

There is a relay flow path 70 between the pressurizing medium chamber 62 and the internal pressure adjusting chamber 63, and a siphon structure 69 is provided halfway on the relay flow path 70.

All of the flow paths 73, 74, 81, 79, 70, and 68 are formed of a thin tube. At least one of the length, girth, and shape of the thin tube may be varied between the flow paths.

In FIG. 15, the reference numerals 67, 71, and 72 denote vents configured to evacuate the respective chambers of air. In FIG. 15, the reference numeral 75 denotes a rotation axis position (reference point).

As illustrated in FIG. 16A to FIG. 16E, blood serving as a fluid sample containing two or more components immiscible with each other and having different specific gravities is separated using a blood separating apparatus serving as the separating apparatus 80 of the second embodiment.

Figure 16A:
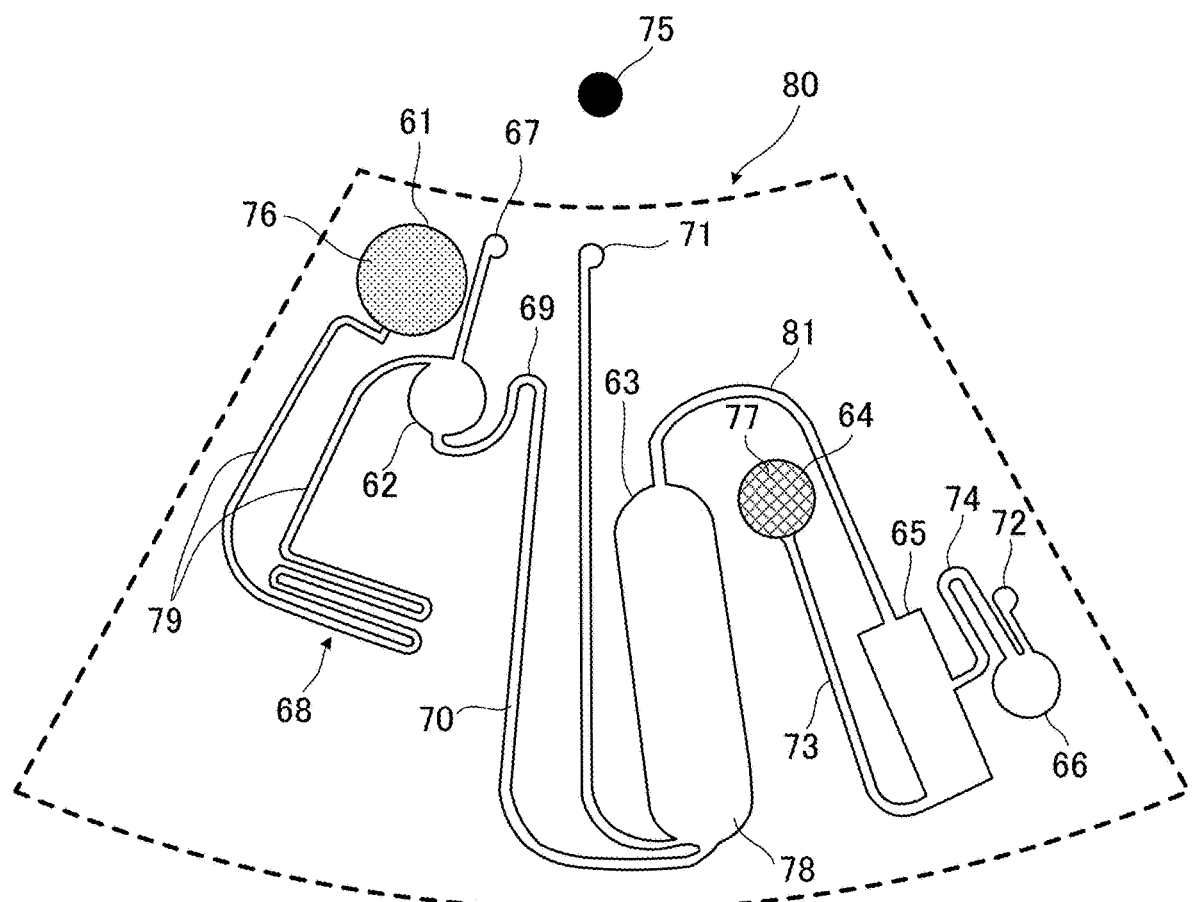
FIG. 16A is a view illustrating an example of a separating method of the present invention using a separating apparatus of a second embodiment.

First, as illustrated in FIG. 16A, water 76 serving as a pressurizing medium is introduced in an amount of 30 microliters into the pressurizing medium introducing chamber 61 using a pipette.

Meanwhile, blood 77 serving as a fluid sample containing two or more components immiscible with each other and having different specific gravities is introduced in an amount of 10 microliters into the sample introducing chamber 64 using a pipette.

Next, like the separating apparatus 40 of the first embodiment, the separating apparatus 80 of the second embodiment is mounted on a disk 90 and rotated in a rotation direction R1 at 1,500 rpm about a rotation axis position 75, to apply a centrifugal force CF to the blood 77 in the sample introducing chamber 64 and the water 76 in the pressurizing medium introducing chamber 61.

Figure 16B:
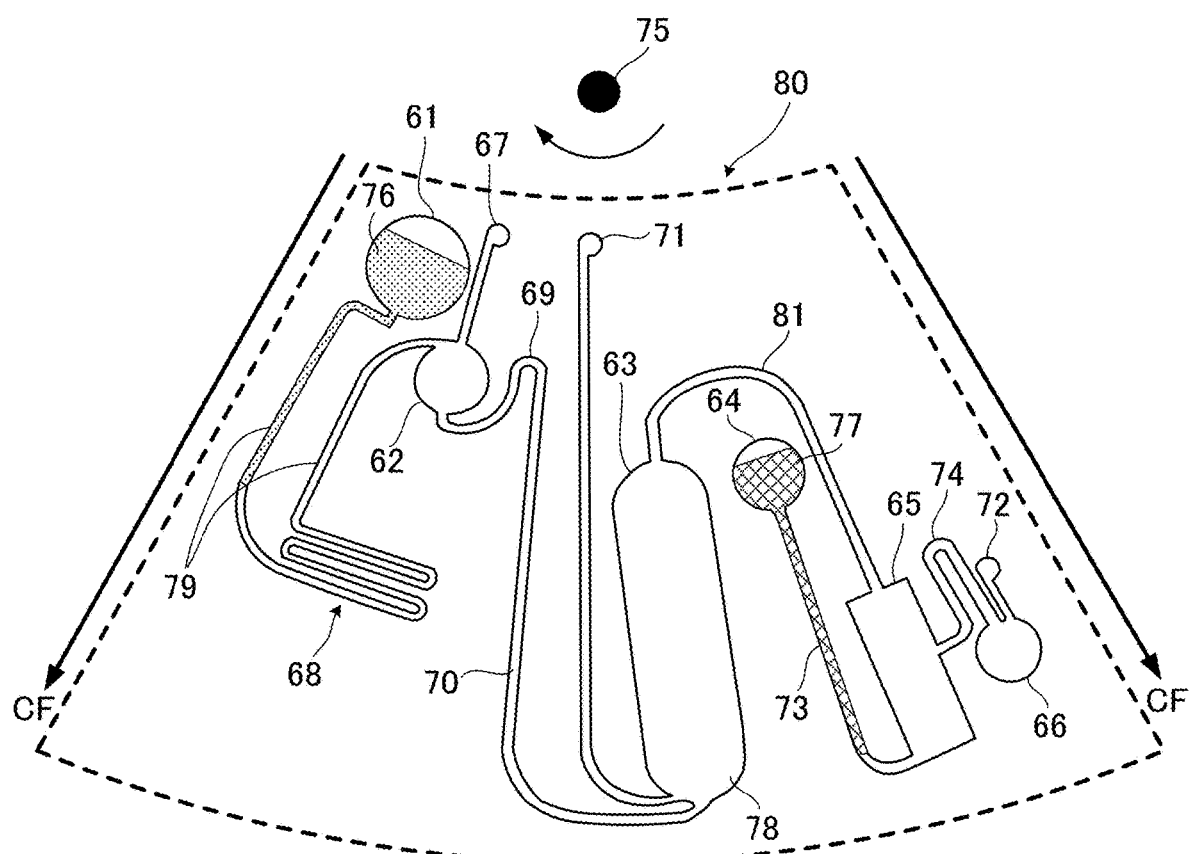
FIG. 16B is a view illustrating an example of a separating method of the present invention using a separating apparatus of a second embodiment.

Next, as illustrated in FIG. 16B, the water 76 is injected into the pressurizing medium chamber 62 from the pressurizing medium introducing chamber 61 through the bent flow path 68. Here, because the pressurizing medium chamber 62 has a vent 67 communicating with the pressurizing medium chamber 62, the water 76 is smoothly injected into the pressurizing medium chamber 62.

Meanwhile, the blood 77 is injected into the separating chamber 65 from the sample introducing chamber 64 through the sample transferring flow path 73. Here, because a vent 72 and a vent 71 are provided, the blood 77 is smoothly injected into the separating chamber 65.

Figure 16C:
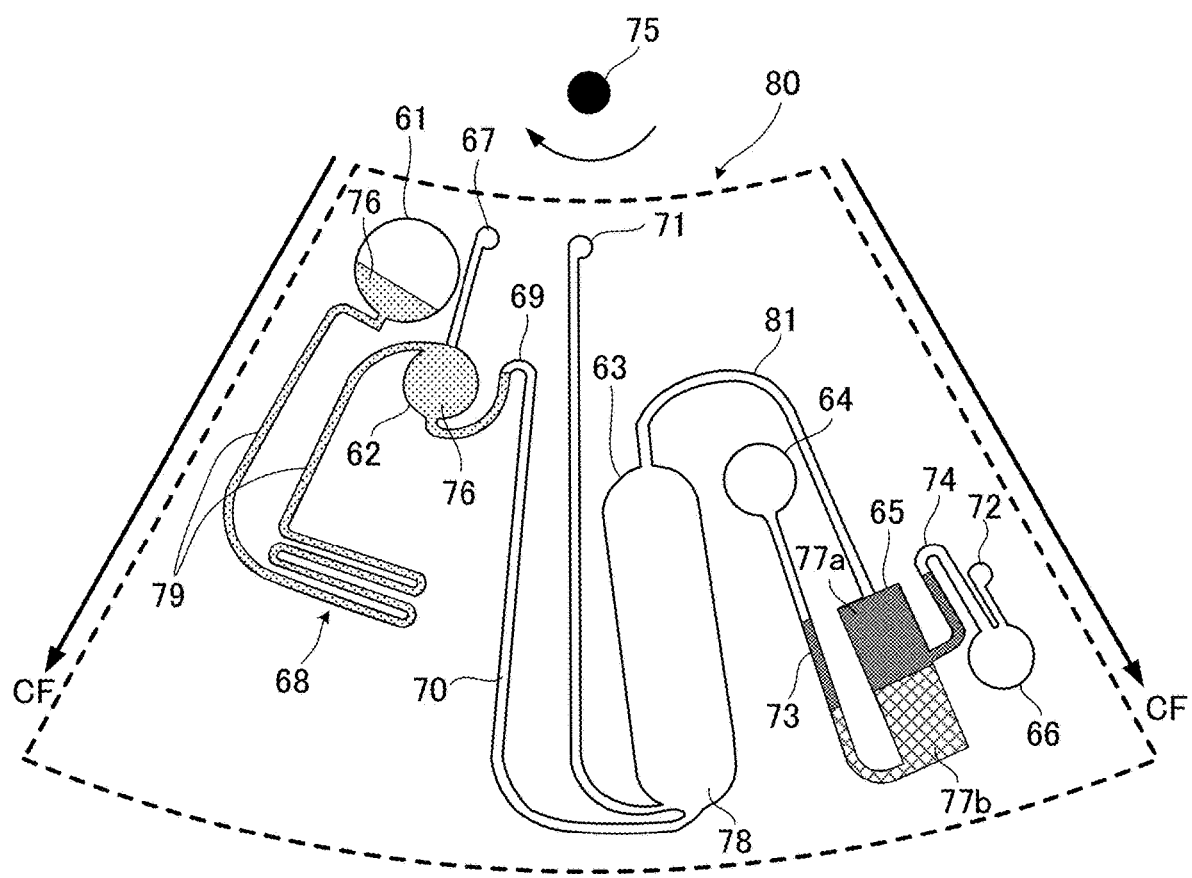
FIG. 16C is a view illustrating an example of a separating method of the present invention using a separating apparatus of a second embodiment.

Next, as illustrated in FIG. 16C, when a centrifugal force CF is applied for a predetermined period of time, the blood 77 injected into the separating chamber 65 is separated into blood plasma 77a and blood corpuscles 77b.

Meanwhile, the water 76 is injected into the pressurizing medium chamber 62 until the water can climb up and down the U-letter-shaped siphon structure 68.

Figure 16D:
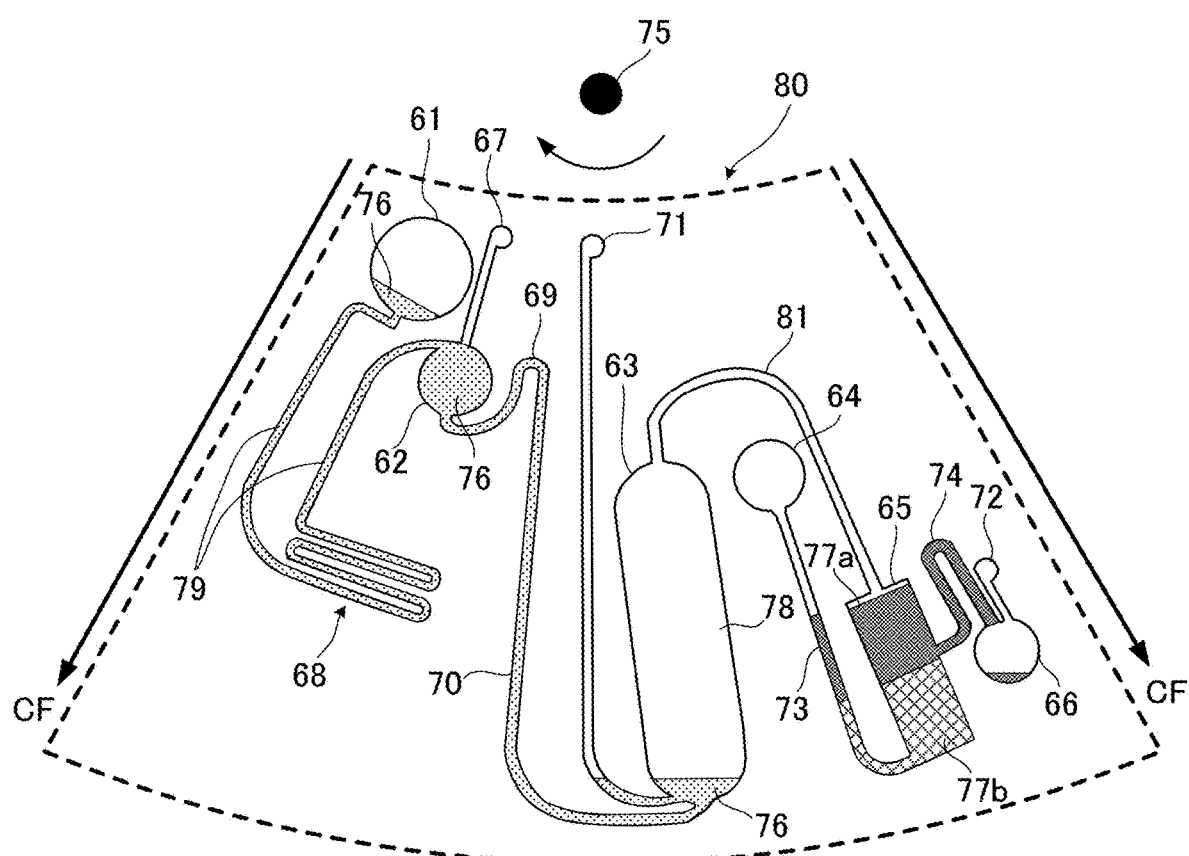
FIG. 16D is a view illustrating an example of a separating method of the present invention using a separating apparatus of a second embodiment.

Next, as illustrated in FIG. 16D, when a centrifugal force CF is further applied, by the siphon principle, the water 76 is injected into the internal pressure adjusting chamber 63 through climbing up and down the U-letter-shaped siphon structure 69, to thereby apply a pressure to air 78 in the internal pressure adjusting chamber 63. Here, because the internal pressure adjusting chamber 63 has a vent 71 communicating with the internal pressure adjusting chamber 63, the water 76 is smoothly injected into the internal pressure adjusting chamber 63. Then, when the water is injected into the internal pressure adjusting chamber 63 by a predetermined amount, the internal pressure adjusting chamber 63 becomes a tightly closed structure.

Meanwhile, by the pressure of the air 78 from the internal pressure adjusting chamber 63, the blood plasma 77a in the separating chamber 65 is transferred to the storing chamber 66 through the separation target transferring flow path 74. Here, because the storing chamber 66 has a vent 72 communicating with the storing chamber 66, the blood plasma 77a is smoothly injected into the storing chamber 66.

Figure 16E:
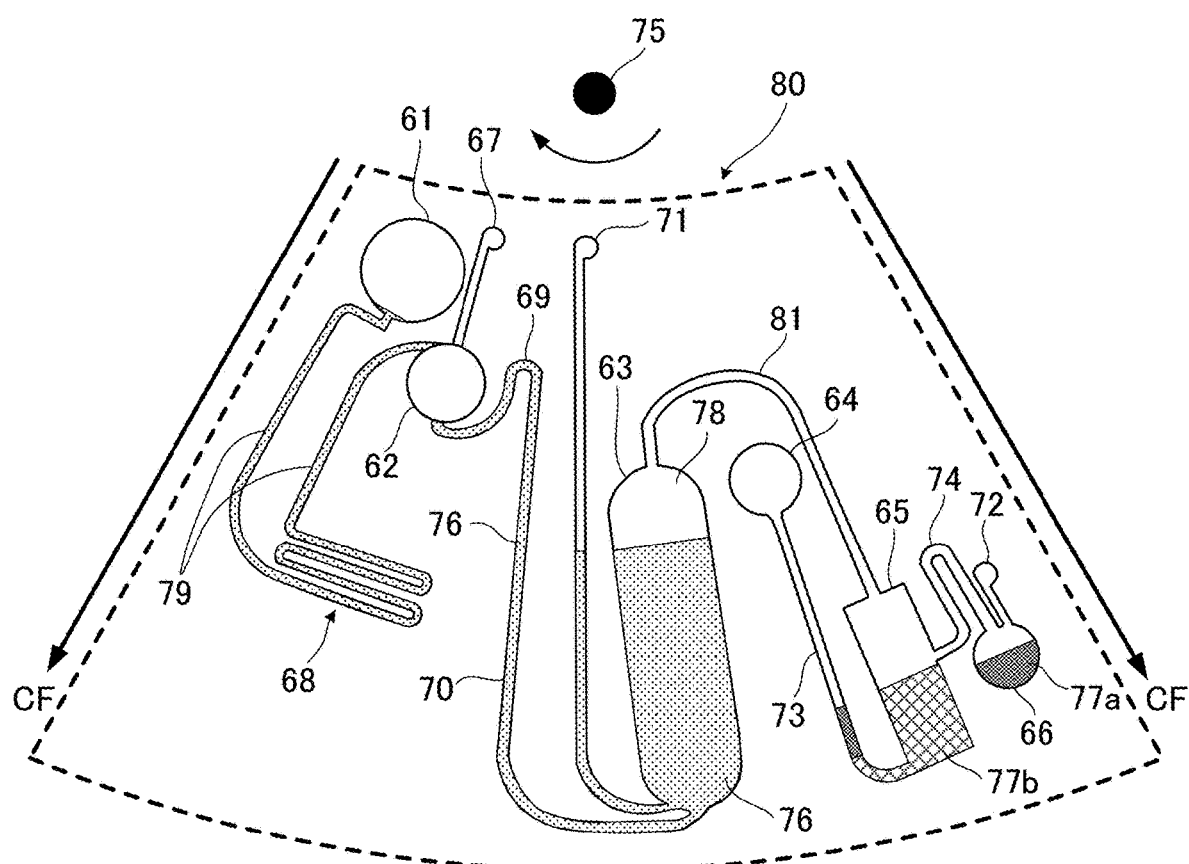
FIG. 16E is a view illustrating an example of a separating method of the present invention using a separating apparatus of a second embodiment.
Figure 17A:
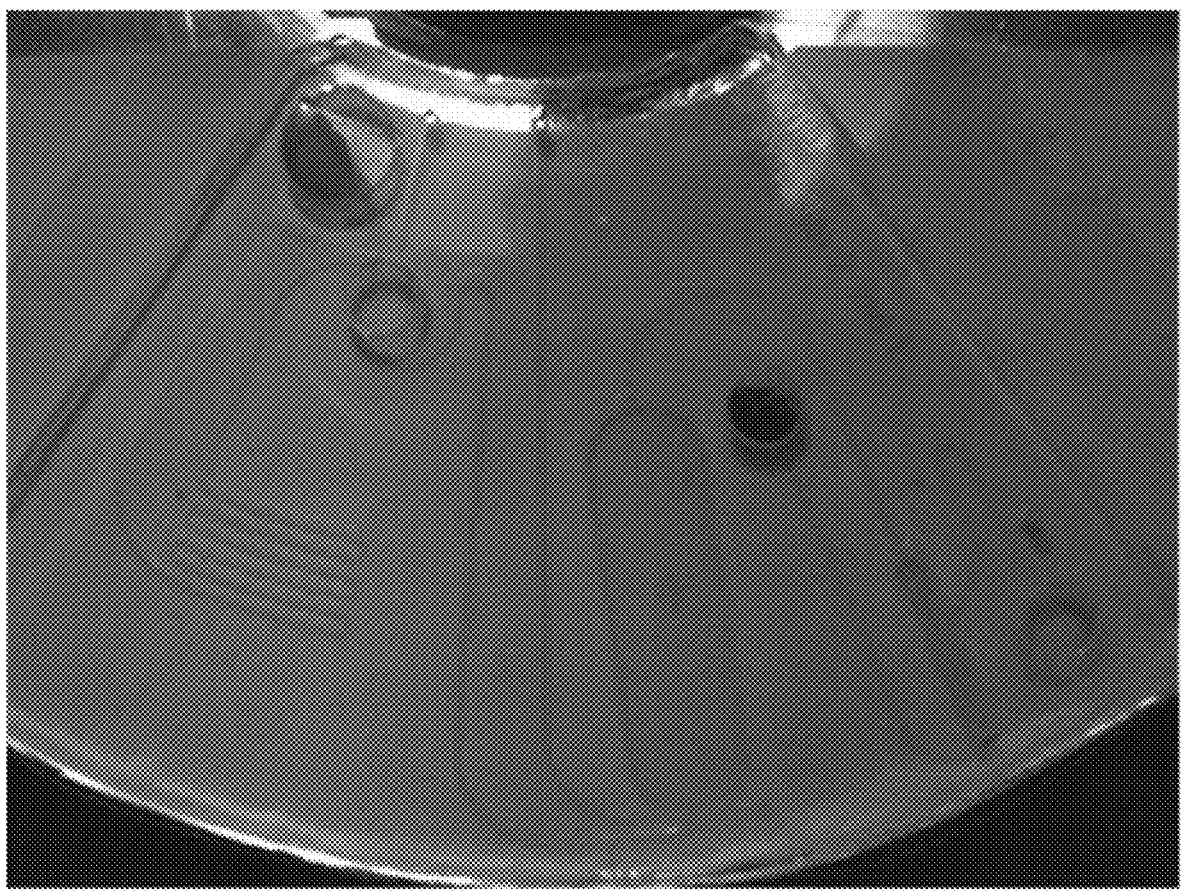
FIG. 17A is an image illustrating an example of a state of blood separation using a separating apparatus of a second embodiment.
Figure 17B:
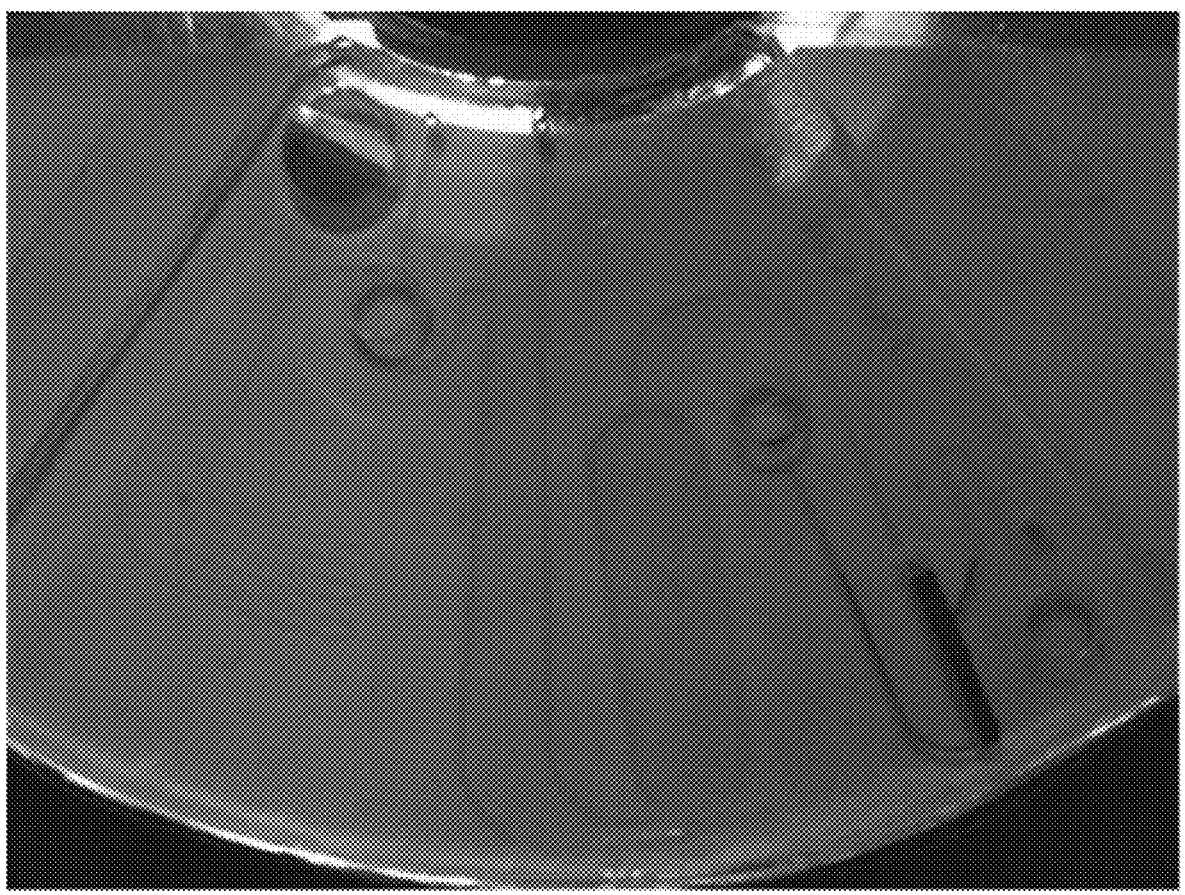
FIG. 17B is an image illustrating an example of a state of blood separation using a separating apparatus of a second embodiment.
Figure 17C:
FIG. 17C is an image illustrating an example of a state of blood separation using a separating apparatus of a second embodiment.
Figure 17D:
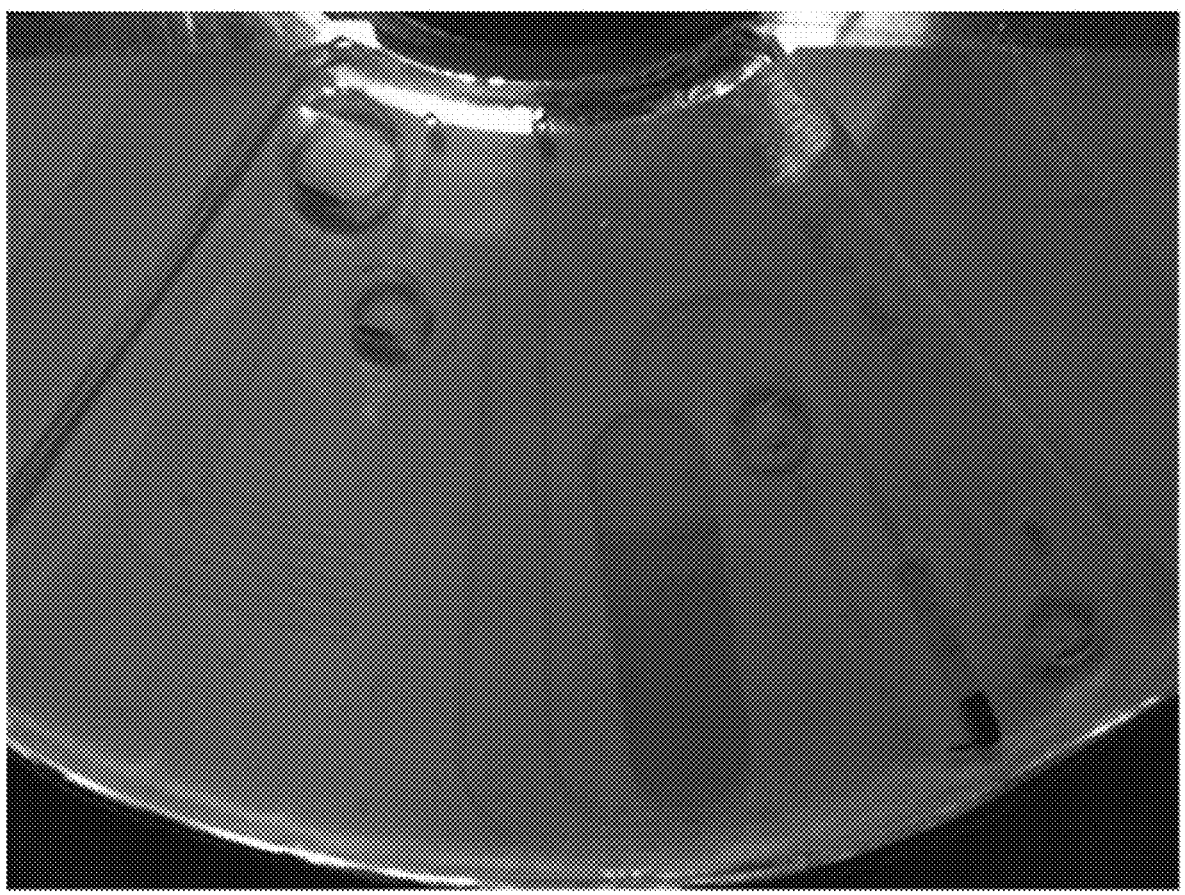
FIG. 17D is an image illustrating an example of a state of blood separation using a separating apparatus of a second embodiment.

Next, as illustrated in FIG. 16E, when a centrifugal force CF is further applied, the blood plasma 77a in the separating chamber 65 is injected into the storing chamber 66 and stored. Through this, blood separation is completed.

The blood separating apparatus serving as the separating apparatus 80 of the second embodiment injects the pressurizing medium into the internal pressure adjusting chamber 63 after a sufficient separation time for separating a fluid sample into a separation target and a non-separation target passes, to thereby increase the pressure of the gas in the internal pressure adjusting chamber 63. By the pressure of the gas, the blood plasma 77a in the separating chamber 65 can be transferred to the storing chamber 66.

Here, FIG. 17A to FIG. 17D are still images (pictures) converted from moving image data representing a state of actual blood separation using the separating apparatus 80 of the second embodiment illustrated in FIG. 15. In the separating apparatus of the second embodiment, polydimethylsiloxane (PDMS), which is a material having a high elasticity, is used for the chambers and flow paths. However, because the cross-sectional shapes of the chambers and flow paths are shapes having an aspect ratio close to 1, such as a square and a circle, change of the cross-sectional shapes due to pressure can be suppressed, and liquid surface displacement can be reduced. From these results, it can be seen that the separating apparatus of the second embodiment can efficiently separate blood with a simple mechanism. In FIG. 17A to FIG. 17D, water serving as the pressurizing medium is colored in blue for visibility.

(Testing Apparatus and Testing Method)

A testing apparatus of the present invention includes a separating unit and a testing unit, and further includes other units as needed.

A testing method of the present invention includes a separating step and a testing step, and further includes other steps as needed.

The testing method of the present invention can be performed by the testing apparatus of the present invention. The separating step can be performed by the separating unit. The testing step can be performed by the testing unit. The other steps can be performed by the other units.

<Separating Unit and Separating Step>

As the separating unit, a separating unit formed of the separating apparatus of the present invention can be used. The details of the separating apparatus are as described above.

As the separating step, a separating step formed of the separating method of the present invention can be used. The details of the separating method are as described above.

<Testing Unit and Testing Step>

The testing step is a step of testing a separation target transferred in a transferring step, and is performed by the testing unit.

It is preferable that a flow path configured to transfer a separation target separated in the separating unit to the testing unit be provided between the separating unit and the testing unit.

It is preferable that the testing unit test a separation target in a state that an external force that is the same as the external force applied to the separating unit is applied to the testing unit. Hence, in the testing apparatus, after a separation target is separated by the separating unit, the testing unit can test the obtained separation target.

The testing unit is not particularly limited and may be appropriately selected depending on the intended purpose so long as it is a unit that can test a separation target. Examples of the testing unit include a micro integrated system (Micro Total Analysis System: μTAS) on which minute flow path structures and valve structures are integrated.

Such a μTAS is not particularly limited and may be appropriately selected depending on the intended purpose. Examples of the μTAS include the testing apparatus described in JP-A No. 2013-088211 and the testing apparatus described in JP-A No. 2017-75807.

<Other Units and Other Steps>

Examples of the other units of the testing apparatus include a control unit.

Examples of the other steps of the testing method include a control step.

As the control unit, for example, a simple controller such as a motor that makes a steady rotation can be used.

(Separating Device)

A separating device of the present invention is a separating device used in any of the separating apparatus of the present invention and the testing apparatus of the present invention, and includes:

an introducing unit into which a fluid sample is introduced;

a separating chamber communicably joined to the introducing unit and capable of separating the fluid sample into two or more fractions in response to application of an external force;

a pressurizing medium chamber communicating with the separating chamber and capable of transferring a pressurizing medium to the separating chamber in response to application of an external force; and a transferring flow path communicating with the separating chamber and capable of transferring the fractions in the separating chamber to outside the separating chamber in response to application of an external force.

The separating device further includes other units as needed.

Examples of the introducing unit include a fluid sample introducing chamber. In order to simplify the introducing method, a flow path mechanism configured to quantitatively introduce blood utilizing a capillary force may be mounted.

The introducing unit includes a pressurizing medium introducing chamber into which a pressurizing medium is introduced. The introducing unit may be equipped with a hematocrit capillary so that blood can be introduced into the introducing unit.

For example, the separating chamber is the same as the separating chamber of the separating unit of the separating apparatus of the present invention.

For example, the pressurizing medium chamber is the same as the pressurizing medium chamber of the transfer mechanism of the separating apparatus of the present invention.

It is preferable to provide a storing unit communicating with a transferring flow path and capable of storing a fraction transferred through the transferring flow path in response to application of an external force.

For example, the storing unit is the same as the storing unit of the separating apparatus of the present invention.

It is preferable to provide the introducing unit, the separating chamber, the pressurizing medium chamber, and the transferring flow path on a rotatable rotating body, and it is preferable that when a centrifugal force is applied as an external force, the fluid sample introduced into the introducing unit be able to move to the separating chamber, and to the transferring flow path in this order.

The separating device may be produced as a disposable product that has the configuration described above and has an excellent safety. The separating device may constitute a separating apparatus in combination with, for example, a rotating body driving apparatus, or may constitute a testing apparatus in combination with a testing unit configured to test a separation target separated by the separating device.

Embodiments of the testing apparatus of the present invention will be described in further detail with reference to the drawings.

First Embodiment of Testing Apparatus

Figure 18:
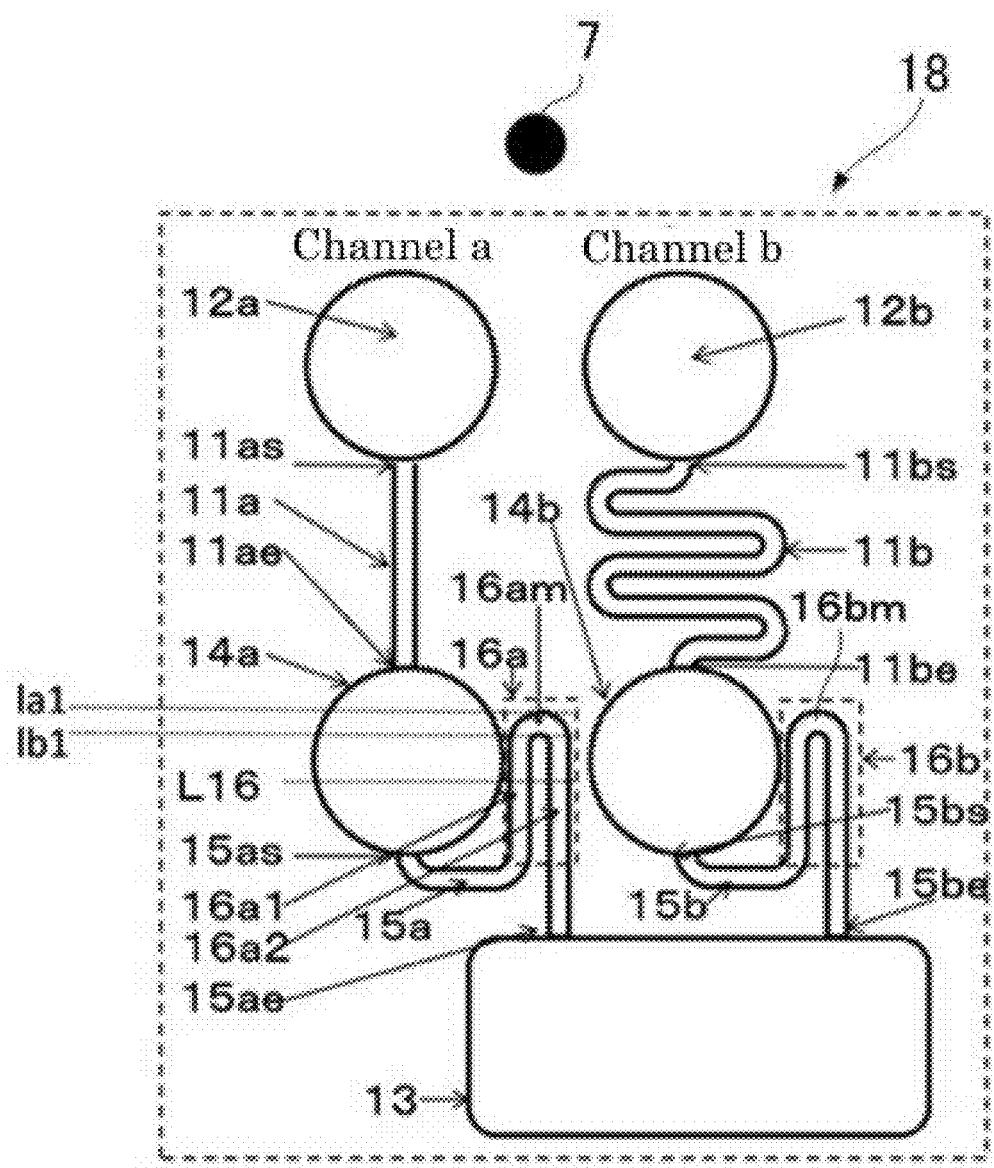
FIG. 18 is a view illustrating an example of a testing apparatus of a first embodiment.

FIG. 18 is a plan view illustrating an example of a testing apparatus 18 of the first embodiment. The testing apparatus 18 of the first embodiment illustrated in FIG. 18 includes two channels a and b, and a chamber 13 to which the two channels a and b are both joined. Although not illustrated, the testing apparatus 18 of the first embodiment communicates through a flow path with the storing chamber 23 of the separating apparatus 40 of the first embodiment illustrated in FIG. 11 or with the storing chamber 66 of the separating apparatus 80 of the second embodiment illustrated in FIG. 15, and is configured to use a separation target separated by the separating apparatus 40 as a sample. The storing chamber 23 or 66 may be the same as the chamber 13 of FIG. 18.

Hereinafter, "channel" generically refers to at least one of a path leading to the chamber, and components or elements or materials that constitute the path.

The channels a and b include first reservoirs 12a and 12b and second reservoirs 14a and 14b, respectively.

Flow paths 11a and 11b are joined to inlet ports 11ae and 11be provided at the top of the second reservoirs 14a and 14b from outlet ports 11as and 11bs provided at the bottom of the first reservoirs 12a and 12b.

Flow paths 15a and 15b are jointed to inlet ports 15ae and 15be provided at the top of the chamber from outlet ports 15as and 15bs provided at the bottom of the second reservoirs 14a and 14b. The channels and b merge with each other in the chamber 13.

The channels a and b are formed independently from each other, and the flow paths of the respective channels are joined to the chamber 13 independently.

All of the flow paths 11a, 11a, 15a, and 15b are formed of thin tubes.

In the testing apparatus 18 of the first embodiment, the first reservoirs 12a and 12b, the second reservoirs 14a and 14b, and the chamber 13 are disposed closer to the rotation axis position 7 in order of mentioning. That is, the reservoirs that store liquids initially are disposed at the upper side, and the chamber 13 to which the liquids come flowing is disposed at the lower side.

During operation of the testing apparatus 18 of the first embodiment, the rotation axis position 7 is configured in a manner that an external force is applied in a direction from the rotation axis position 7 toward the chamber 13. The testing apparatus 18 of the first embodiment illustrated in FIG. 18 is configured in a manner that an external force is applied in a direction from the rotation axis position 7 toward the bottom of FIG. 18, i.e., from the upper side to the lower side of the testing apparatus 18 of the first embodiment. The rotation axis position 7 is also a reference point that defines the upstream side of the testing apparatus 18.

The flow path 11a constituting the channel a and joining the first reservoir 12a to the second reservoir 14a and the flow path 11b constituting the channel b and joining the first reservoir 12b to the second reservoir 14b have different lengths from each other. In the testing apparatus 18 of the first embodiment illustrated in FIG. 18, the flow path 11b is longer than the flow path 11a.

The testing apparatus 18 of the first embodiment illustrated in FIG. 18 is illustrated as a configuration with different lengths. In order to generate a difference in time needed for liquids, which are flowed through the respective channels from the first reservoirs 12a and 12b to the second reservoirs 14a and 14b, to pass through the channels, the flow paths 11a and 11b may be varied in girth and shape. Moreover, in order to generate a difference in time, at least one of length, girth, and shape may be varied between the flow paths 11a and 11b. Because the flow paths 11a and 11b are formed of thin tubes, liquids take respective predetermined times to pass, and the flow paths function as resistance flow paths. Volume and position may be varied between the second reservoirs 14a and 14b.

The flow paths 15a and 15b that join the second reservoirs 14a and 14b to the chamber 13 are both provided with siphon structures 16a and 16b.

The siphon structures 16a and 16b include a first flow path section 16a1, which is a flow path formed in a first direction heading for the rotation axis position 7, and a second flow path section 16a2, which is a flow path formed in a second direction in which an external force acts oppositely to the first flow path section 16a1.

The first flow path section 16a1 is formed closer than the second flow path section 16a2 to the second reservoir (upstream side).

A vector component with respect to an external force direction, of a vector heading in the first direction is in a direction exactly opposite to the external force direction. A vector component with respect to the external force direction, of a vector heading in the second direction is in the same direction as the external force direction. As needed, the first direction and the second direction may have angular differences from the external force direction, and may meander so long as the conditions described above are satisfied.

In the testing apparatus 18 of the first embodiment, the first flow path section 16a1 and the second flow path section 16a2 of the siphon structure are joined to each other at a bent point 16am. The bent point 16am is positioned between the inlet port 11ae and the outlet port 15as of the second reservoir 14a, seen from the rotation axis position 7. That is, the interval between the rotation axis position 7 and the bent point 16am is a value somewhere between the interval between the rotation axis position 7 and the inlet port 11ae, which is the top of the second reservoir 14a and the interval between the rotation axis position 7 and the outlet port 15as, which is the bottom of the second reservoir 14a.

In actual designing, the bent point 16am is set at a position equal to or lower than the water level (the upper liquid surface) in the second reservoir 14a reached when the whole of the liquid injected into the first reservoir 12a initially is transferred to the second reservoir 14a. The positions of the bent points 16am and 16bm may be varied.

The first reservoirs 12a and 12b, the second reservoirs 14a and 14b, and the chamber 13 all have vents although not illustrated in FIG. 18. These vents are opened as needed during use of the testing apparatus 18.

As illustrated in FIG. 19, the testing apparatus 18 of the first embodiment is disposed per section (83, 84, . . . ) of a disk 82, so one or a plurality of the testing apparatus is/are provided on the disk 82 to constitute a measuring unit 88. A testing apparatus 18-1 of the first embodiment is disposed in the section 83, a testing apparatus 18-2 of the first embodiment is disposed in the section 84, and a further testing apparatus of the first embodiment may be disposed as needed.

In the broader sense of the term, the measuring unit 88 per se is a testing apparatus. Examples of the disk 82 include compact discs (CD), digital video discs (DVD), and swing rotors. The disk 82 has a hole in the center for receiving a rotation shaft of a disk driving apparatus configured to rotate the disk 82. The center of this hole corresponds to the rotation axis position 7 of the testing apparatus 80 of the first embodiment. The measuring unit 88 is incorporated as an apparatus together with, for example, a disk driving apparatus, and constitutes a testing apparatus such as a biopsy apparatus and a chemical analyzer.

FIG. 20 illustrates a cross-sectional structure of a portion along a line L16-L16 indicated over the testing apparatus 18-1 formed on the disk 82. The line L16-L16 represents a cross-sectional structure of the second reservoir 14a and the siphon structure 16b formed on the flow path 15a of the testing apparatus 18 of the first embodiment illustrated in FIG. 18. The reference numeral 194 denotes a base material of the disk 82, and there is a polydimethylsiloxane (PDMS) sheet (PDMS sheet) 193 on the base material 194. A second reservoir 195 and a thin tube 196 of a siphon structure are formed by a lithography technique in a PDMS layer 192 formed on the PDMS sheet 193. A cover layer 191 is provided on the PDMS layer 192. For reducing influence of elasticity, it is preferable that the cross-sectional shape of a chamber be a shape having an aspect ratio close to 1, such as a square and a circle. As a material having a higher stiffness than PDMS, for example, PMMA, PC, PS, or COP may be used to produce, for example, reservoirs and flow paths by, for example, injection molding.

Next, a fluid control mechanism of the testing apparatus 18 of the first embodiment will be described with reference to FIG. 21A to FIG. 21D. Here, for descriptive expediency, chambers 13 are illustrated as chambers 13a and 13b separately for respective channels. One chamber 13 suffices when mixing liquids, which are flowed through the two channels a and b, in the chamber 13 in a desired fluid control of the testing apparatus. In any case, the chamber 13 operates in the same manner.

The flow control mechanism of the testing apparatus 18 of the first embodiment is intended for a two-step sequence. With the configuration of the testing apparatus of the present embodiment, it is possible to control the order of injection of liquids fla and flb into the chamber 13 from the second reservoirs 14a and 14b.

First, as illustrated in FIG. 19, the disk 82 on which the testing apparatus 18 of the first embodiment is mounted is disposed horizontally in a manner that the cover layer 191 comes to the top.

Figure 21A:
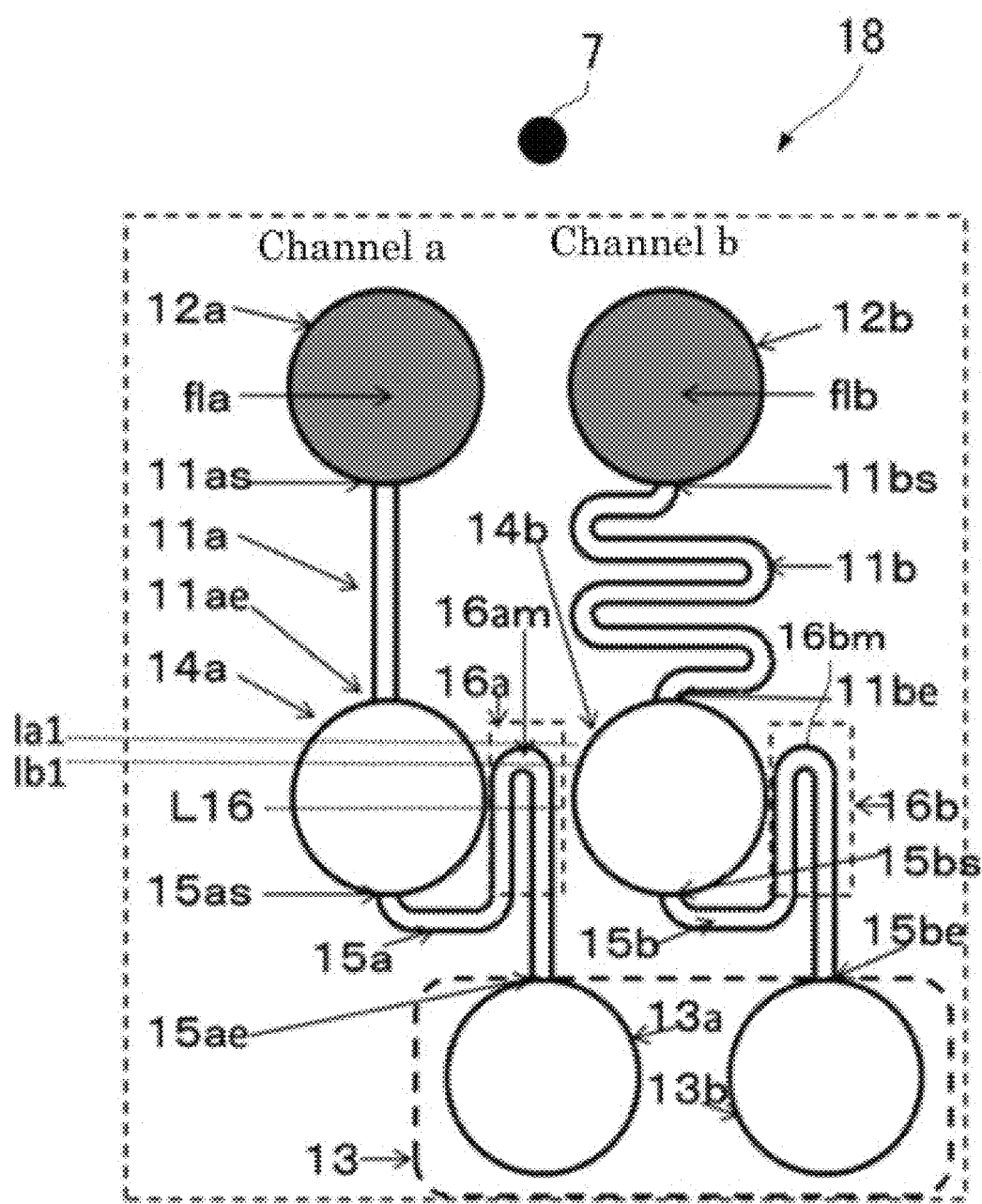
FIG. 21A is a view illustrating an example of an operation in a testing method using a testing apparatus of a first embodiment.
Figure 21B:
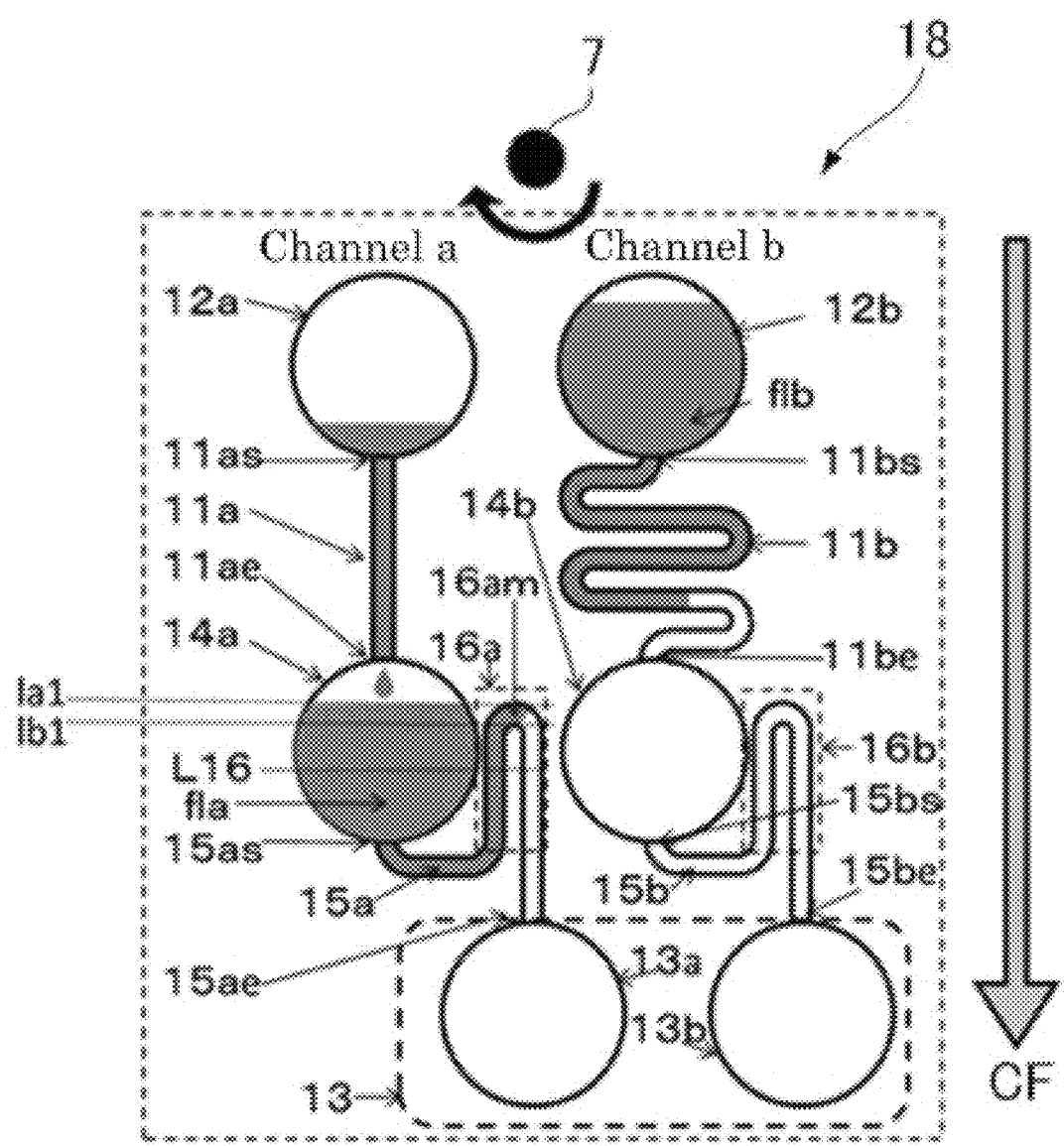
FIG. 21B is a view illustrating an example of an operation in a testing method using a testing apparatus of a first embodiment.
Figure 21C:
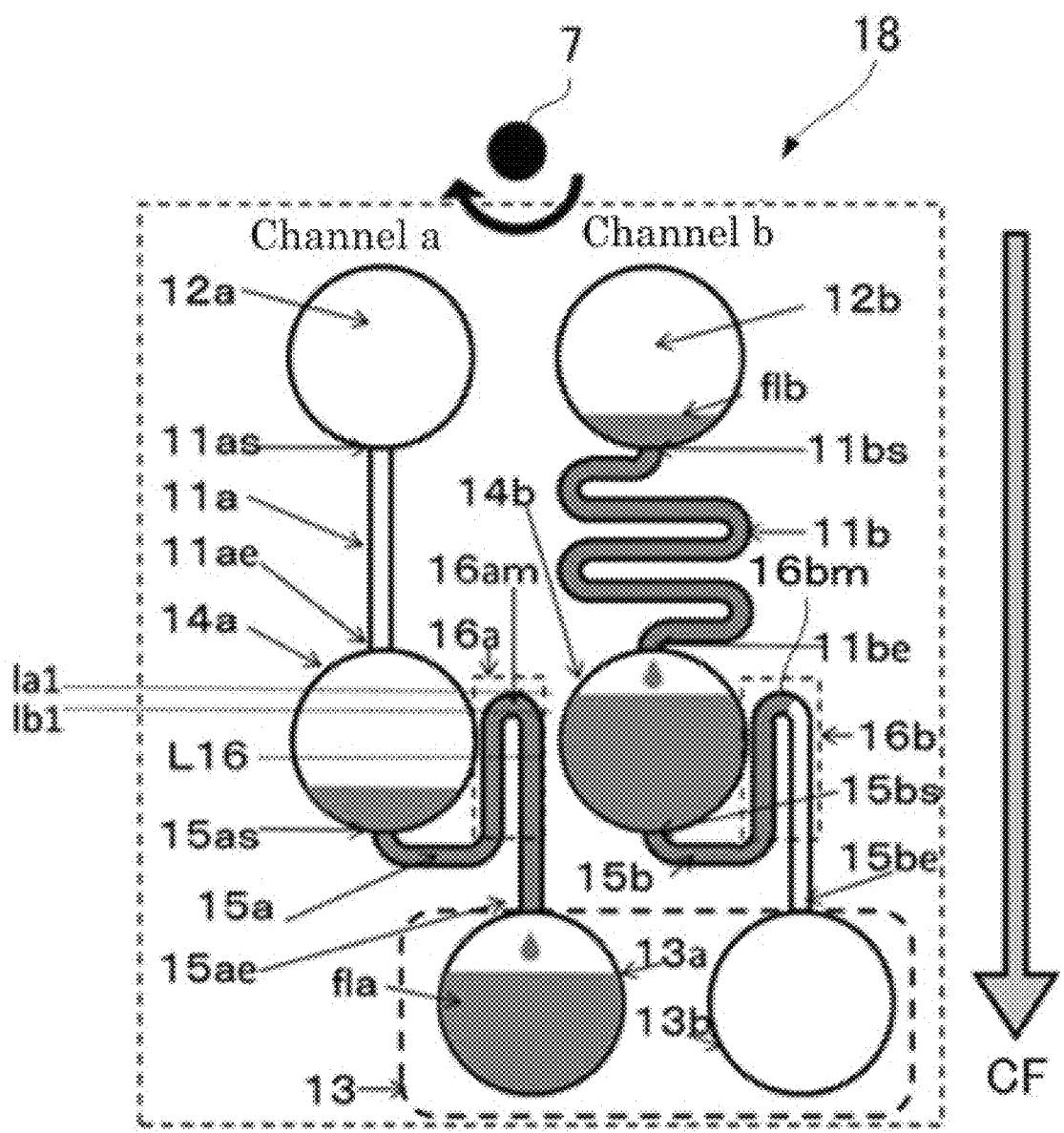
FIG. 21C is a view illustrating an operation in a testing method using a testing apparatus of a first embodiment.

Next, as illustrated in FIG. 21A, desired liquids are stored in the first reservoirs 12a and 12b. In the testing apparatus 18 of the first embodiment, the liquids are injected into the first reservoirs 12a and 12b through holes opened in the cover layer 191 at positions above the first reservoirs 12a and 12b.

Next, a measuring unit 98 on the disk 82 on which the testing apparatus 18 of the first embodiment is mounted is rotated about the rotation axis position 7 (in the R1 direction in FIG. 19). Here, the rotation number of the disk 82 may be a desired rotation number, and the set value of the rotation number may be a constant value. As a result, a centrifugal force CF is applied to the liquids injected into the first reservoir 12a of the channel a and the first reservoir 12b of the channel b (see FIG. 21B).

In the testing apparatus 18 of the first embodiment, the centrifugal force CF corresponds to the external force described above. Hence, as desired, the external force is applied in a direction from the rotation axis position 7 toward the chamber 13 of the testing apparatus 18. The liquids fla and flb are injected into the flow paths 11a and 11b, respectively. Subsequently, the liquids flow into the second reservoirs 14a and 14b.

Next, the liquids fla and flb are once stored in the second reservoirs 14a and 14b because the siphon structures 16a and 16b are provided next to the second reservoirs 14a and 14b. Because the same body-force (centrifugal force) acts on the liquids fla and flb in the channels a and b, the liquids are stored in the second reservoirs 14a and 14b faster through the channel a having a shorter flow path than through the channel b (see FIG. 21B and FIG. 21C).

Next, after the liquids in a certain amount are stored in the second reservoirs 14a and 14b, the liquids climb up and down the siphon structures 16a and 16b and flow into the chamber 13. Therefore, the liquids are injected into the chamber 13. Because the liquids are stored in the second reservoirs 14a and 14b faster through the channel a than through the channel b, liquid injection into the chamber 13a is faster through the channel a (see FIG. 21B and FIG. 21C).

Figure 21D:
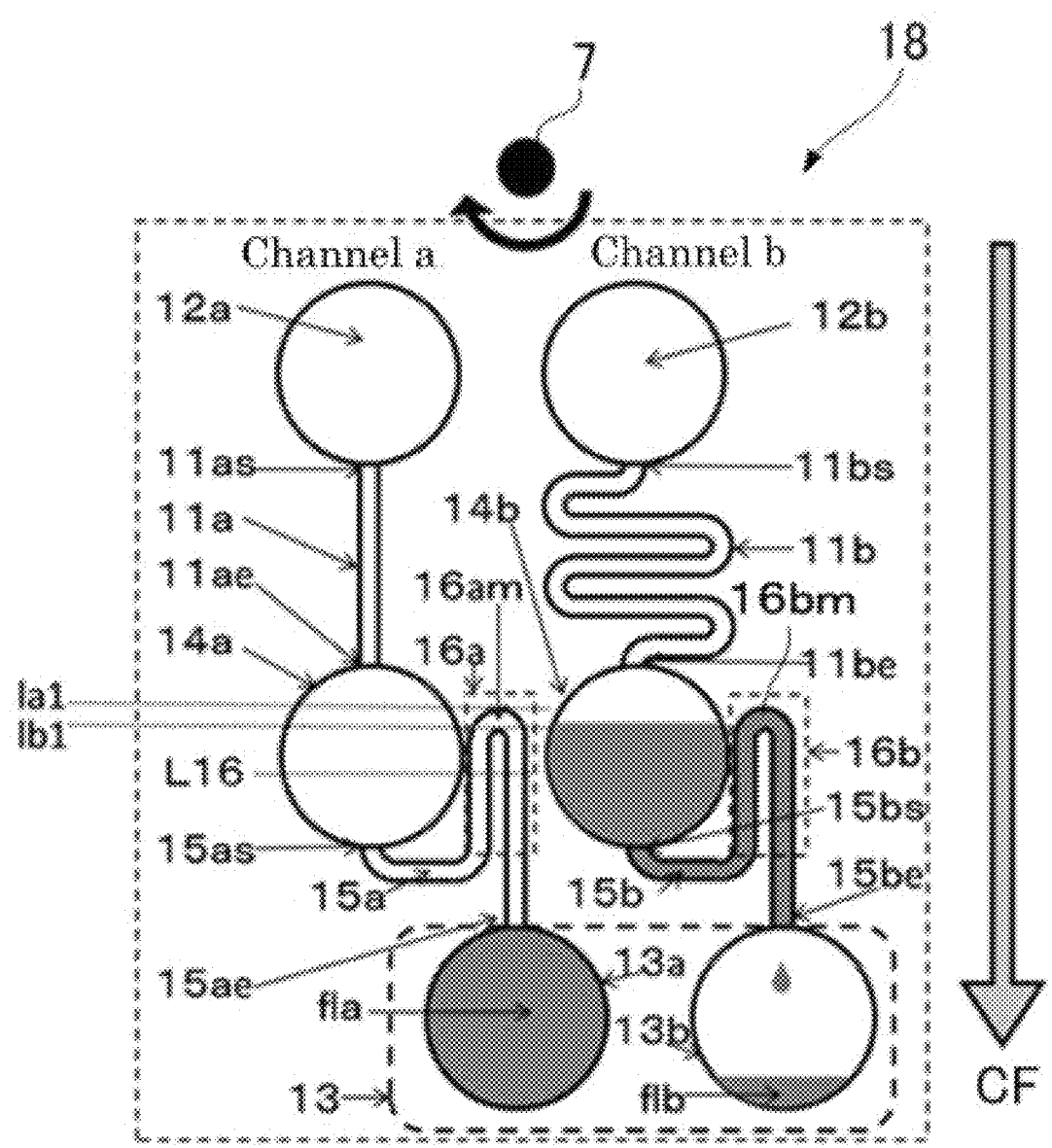
FIG. 21D is a view illustrating an example of an operation in a testing method using a testing apparatus of a first embodiment.

Next, because the channel b having the longer flow path 11b has a higher flow path resistance and the liquid flb is stored more slowly in the second reservoir 14b, the liquid flb is injected into the chamber 13b lagging behind through the channel a (see FIG. 21D).

Next, when the upper liquid surface of the liquid stored in the second reservoir 14b reaches a level above the bent point of the siphon structure 16b, the liquid starts to flow through the siphon structure 16b. Hence, as illustrated for the channel a in FIG. 21D, when the level of the upper liquid surface of the liquid stored in the second reservoir 14a reaches the position of the bent point 16am between the level lb1 and the level la1, the liquid starts to flow into the chamber 13. It is also possible to control the time taken for the liquid to pass through the channel a, by changing the position of the bent point 16am.

As described above, in the testing apparatus 18 of the first embodiment, sequential fluid control can be actively performed without switching of the rotation number of the disk or opening/closing of valves externally. Moreover, sequential liquid control can be actively performed by steady rotation without a complicated valve mechanism on the disk 82. Furthermore, with independent channels for the two liquids fla and flb, mixing does not occur before the chamber 13, making it possible to avoid mixed presence of the liquids halfway through a flow path.

Without a special external trigger but with a centrifugal force, which is generated at a single rotation number, acting as the external force, two or more liquids can be supplied into a chamber with time difference and without mixed presence of two liquids at an unintentional timing due to, for example, leak of the air into the flow path. Therefore, it is possible to prevent mixed presence of liquids in the chamber at a wrong timing, which may be a cause of variation in analytical results. Because mixed presence of liquids anywhere other than in the chamber may be a cause of variation in analytical results, it is important to prevent mixed presence of liquids anywhere other than in the chamber.

Second Embodiment of Testing Apparatus

Figure 22:
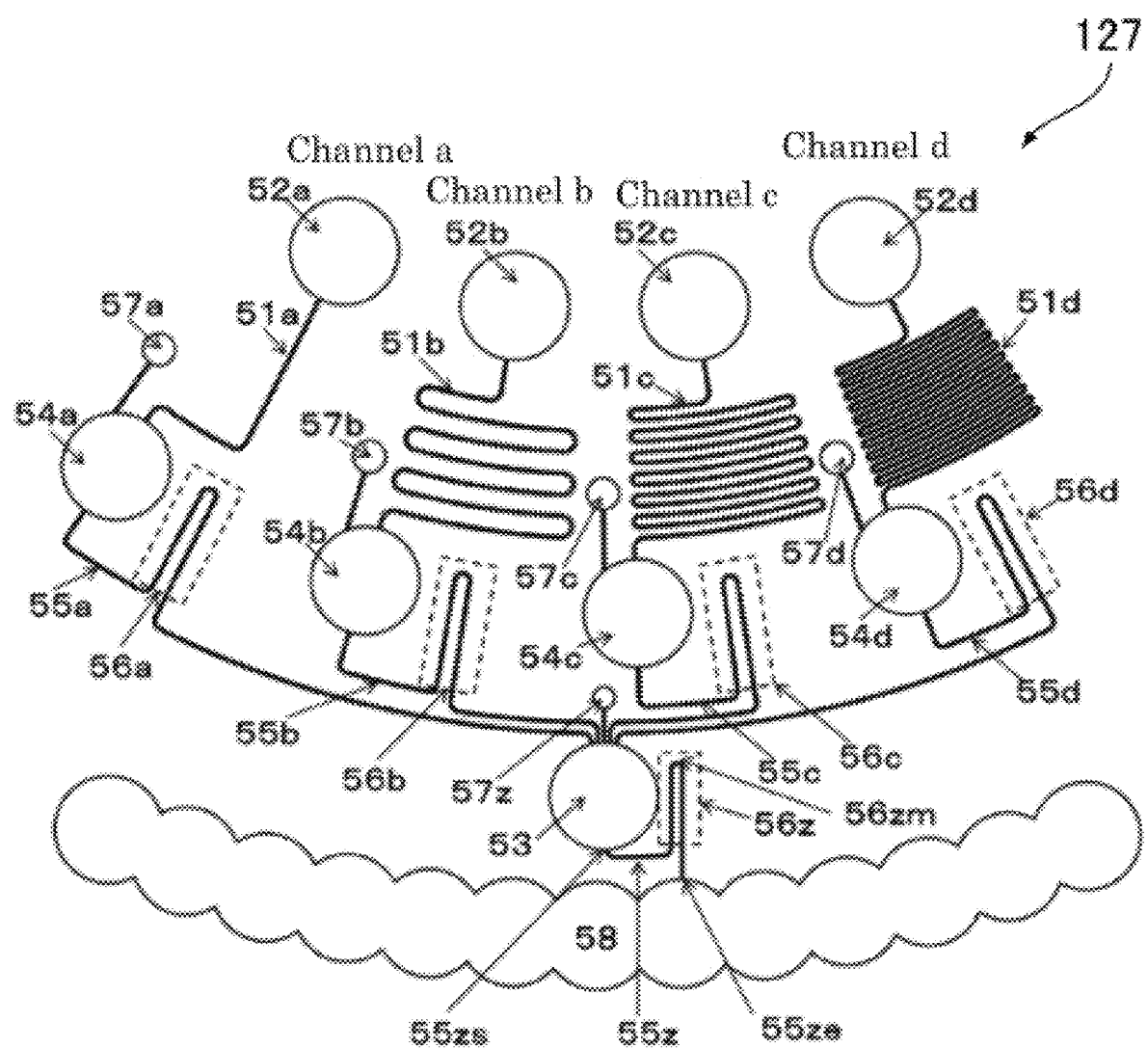
FIG. 22 is a view illustrating an example of a testing apparatus of a second embodiment.

FIG. 22 is a plan view of a testing apparatus 127 of the second embodiment. The testing apparatus 127 of the second embodiment illustrated in FIG. 22 is an embodiment for performing testing by enzyme immunoassay, and is the same as the testing apparatus 18 of the first embodiment except that the two channels in the testing apparatus 18 of the first embodiment is changed to four channels. The components of the testing apparatus 127 of the second embodiment that are the same as those of the testing apparatus 18 of the first embodiment already described will be denoted by the same reference numerals, description of such components will be skipped.

The testing apparatus 127 of the second embodiment includes four channels a, b, c, and d, and a chamber 53 to which all of the four channels are joined.

The four channels a to d independently include first reservoirs 52a to 52d, second reservoirs 54a to 54d, flow paths 51a to 51d joining the first reservoirs 52a to 52d to the second reservoirs 54a to 54d, and flow paths 55a to 55d joining the second reservoirs 54a to 54b to the chamber 53, respectively.

Although not illustrated, the testing apparatus 127 of the second embodiment communicates through a flow path with the storing chamber 23 of the separating apparatus 40 of the first embodiment illustrated in FIG. 11 or with the storing chamber 66 of the separating apparatus 80 of the second embodiment illustrated in FIG. 15, is configured to use a separation target separated by the separating apparatus as a sample of the testing apparatus. The storing chamber 23 or 66 may be the same as the camber 13 of FIG. 18.

As in the testing apparatus 18 of the first embodiment, in the testing apparatus 127 of the second embodiment, the first reservoirs 52a to 52d, the second reservoirs 54a to 54d, and the chamber 53 are disposed closer to the rotation axis position (reference point) 7 in order of mentioning.

The flow paths 51a to 51d of the respective channels are configured to have a flow path length relationship of 51a<51b<51c<51d and to be different from one another. Instead of the flow path length, the flow path girth and the flow path shape are varied, in order to constitute resistance flow paths to have a relationship of 51a<51b<51c<51d in terms of a predetermined period of time taken for liquids to pass through the flow paths 51a to 51d formed of thin tubes, respectively. That is, the fluids (liquids) stored in the first reservoirs 52a to 52d are configured to reach the chamber 53 in order of the channel a, the channel b, the channel c, and the channel d.

Siphon structures 56a to 56d are formed on the flow paths 55a to 55d, respectively. The structure of the siphon structures is the same as in the testing apparatus 18 of the first embodiment.

The first reservoirs 52a to 52d, the second reservoirs 54a to 54b, and the chamber 53 have vents, respectively.

FIG. 22 illustrates vents 57a to 57d, and a vent 57z corresponding to the second reservoirs 54a to 54b, and the chamber 53, respectively. Each vent is opened as needed during use of the testing apparatus.

A waste liquid from the chamber 53 is transferred to a waste liquid tank 58 through a flow path having a siphon structure 56z.

Like the siphon structures 56a to 56d, and the siphon structures 16a and 16b of the testing apparatus 18 of the first embodiment, the siphon structure 56z includes a third flow path section, which is a flow path formed in a third direction heading for the rotation axis position 7, and a fourth flow path section, which is a flow path formed in a fourth direction in which an external force acts oppositely to the third direction. That is, the third direction is a direction against an external force, and the fourth direction is a direction following an external force.

Like the testing apparatus 18 of the second embodiment, the testing apparatus 127 of the second embodiment is formed on the disk 82 as illustrated in FIG. 19, and has the same structure.

Figure 23:
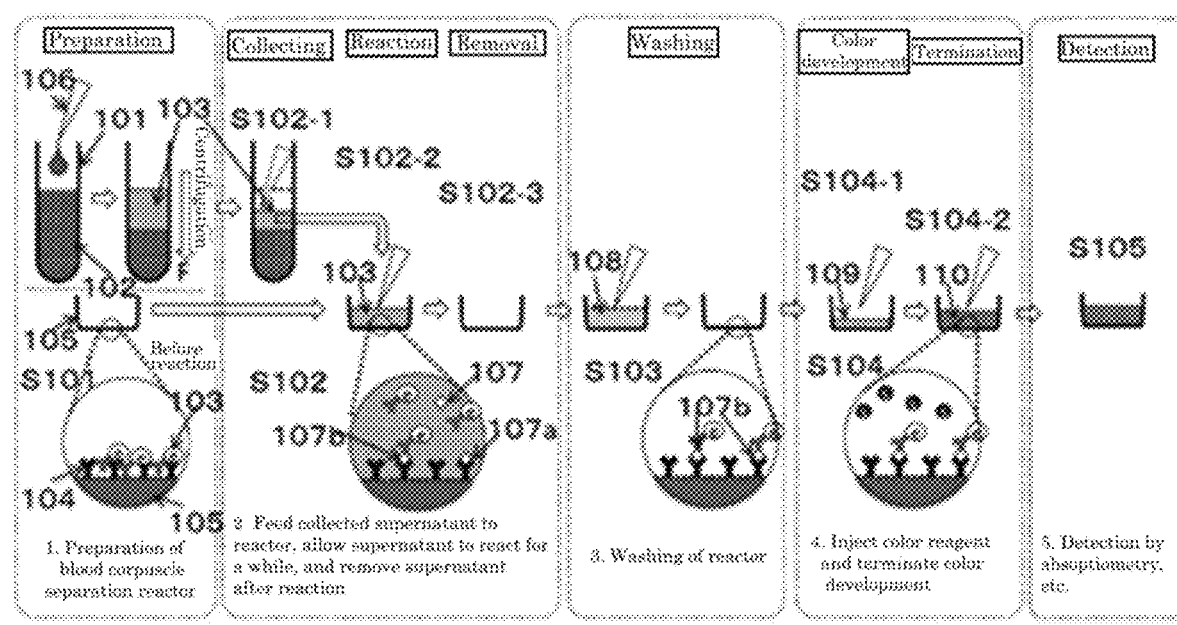
FIG. 23 is a diagram illustrating an example of an enzyme immunoassay method.

FIG. 23 is a diagram illustrating an example of enzyme immunoassay
(Enzyme-Linked Immuno-Sorbent Assay: ELISA).

In the step S101, as previous preparation, blood 102 is weighed out in an appropriate amount in, for example, a test tube 101 with, for example, a pipette 106, and centrifuged to extract a supernatant (blood plasma) 103 of the blood. A test substance 107 is contained in the blood plasma. In the present invention, blood plasma separation is performed using the separating apparatus 40 of the first embodiment illustrated in FIG. 11 or the separating apparatus 80 of the second embodiment illustrated in FIG. 15.

Meanwhile, a chamber 105 in which a capture antibody 104 is immobilized and a labeled antibody 103 for detection is coated is previously prepared. The labeled antibody 103 for detection is an antibody labeled with an enzyme or a fluorescent dye. FIG. 23 illustrates a case where a horse radish peroxidase (HRP) is used.

In the step S102, the blood plasma is fed into the prepared chamber 105 (S102-1), to allow the test substance 107 in the blood plasma to undergo reaction (S102-2). Then, the blood plasma is removed (S102-3). In this stage, a reaction product of the test substance 107 with the capture antibody 104 and the labeled antibody 103 for detection adheres to the internal wall of the chamber 105 (107b). The reference numeral 107a denotes a product to which only either one adheres.

In the step S103, the internal wall of the chamber 105 is cleaned with a phosphate buffered saline (PBS) 108 in order to rinse away extra blood plasma. A PBS to which a surfactant is added is preferable. It is preferable to perform cleaning a plurality of times.

In the step S104, a cleaned color reagent (matrix) 109 is injected, to prompt the reaction product of the test substance 107 with the capture antibody 104 and the labeled antibody 103 for detection adhering to the internal wall of the chamber 105 to develop a color (S104-1).

As the color reagent, for example, tetramethylbenzidine (TMBZ) is used. After a predetermined period of time passes, 1 M (mol/L) sulfuric acid $H_2SO_4$ is further fed, in order to terminate the color developing reaction (S104-2). A solution 110 of TMBZ (109) to which sulfuric acid is added is obtained in the chamber 105.

In the step S105, in the state of the step S104 in which color development is terminated, the degree of color development of the test substance 107 is measured using, for example, absorptiometry, to measure the amount of the test substance 107.

Such an enzyme immunoassay (ELISA) can be performed in the manner described below using the testing apparatus 127 of the second embodiment.

Although not illustrated, the first reservoir 52a communicates through a flow path with the storing chamber 23 of the separating apparatus 40 of the first embodiment illustrated in FIG. 11 or the storing chamber 66 of the separating apparatus 80 of the second embodiment illustrated in FIG. 15, and blood plasma separated by the separating apparatus is transferred to the first reservoir 52a. The storing chamber 23 or 66 may be the same as the chamber 13 of FIG. 18.

First, the capture antibody 104 and the labeled antibody 103 for detection illustrated in the step S101 are previously immobilized to or coated on the internal wall of the chamber 53 of the testing apparatus 127 of the second embodiment.

Next, a supernatant (blood plasma) of blood, a cleaning liquid (PBS), a matrix (TMBZ), and a terminating agent (1 M $H_2SO_4$) are prepared in the first reservoir 52a of the channel a, the first reservoir 52b of the channel b, the first reservoir 52c of the channel c, and the first reservoir 52d of the channel d, respectively.

Next, the disk 82 on which the testing apparatus 127 of the second embodiment is mounted is rotated at a constant rotation number, to apply a centrifugal force as an external force. The testing apparatus 127 of the second embodiment is configured as described above and sequentially performs an analysis using the centrifugal force applied at a predetermined rotation number.

The fluids (liquids) stored in the first reservoirs 52a to 52d are supposed to reach the chamber 53 in order of the channel a, the channel b, the channel c, and the channel d.

The flow paths 51a to 51d have such lengths (or flow path girths, or flow path shapes, or combination of these) as to enable the next fluid to enter the chamber 53 in a sufficient period of time with a desired time interval after the fluid of a previous channel is injected completely into the chamber 53.

Next, the supernatant (blood plasma) of the blood is injected into the chamber 53 in which the capture antibody 104 is immobilized and the labeled antibody 103 for detection is coated, to allow the test substance 107 in the blood plasma to undergo reaction sufficiently.

Next, cleaning of the chamber 53 with the cleaning liquid, color development by injection of the matrix, and termination of the color developing reaction by the terminating agent are performed successively.

With the siphon structures 56a to 56d provided on the channel a to the channel d, the fluids (liquids) are stored in the second reservoirs 54a to 54d until desired amounts are reached. After a predetermined amount is stored, each fluid can be injected at a breath into the chamber 53 by the siphon principle. Hence, the same state as in the actual analytical method can be realized.

Next, by seeing to it that the terminating agent for terminating a reaction reaches the chamber 53 after the matrix is allowed to undergo reaction for a predetermined period of time, and that no mixed liquid of the matrix solution and the terminating agent reaches the siphon structure 56z and flows out into the waste liquid tank 58, it is possible to analyze the mixed liquid in the chamber 53 by such a method as a colorimetric method and obtain a result.

The reaction example described above is one example, and the apparatus is applicable to various biopsies and chemical analyses.

Figure 24:
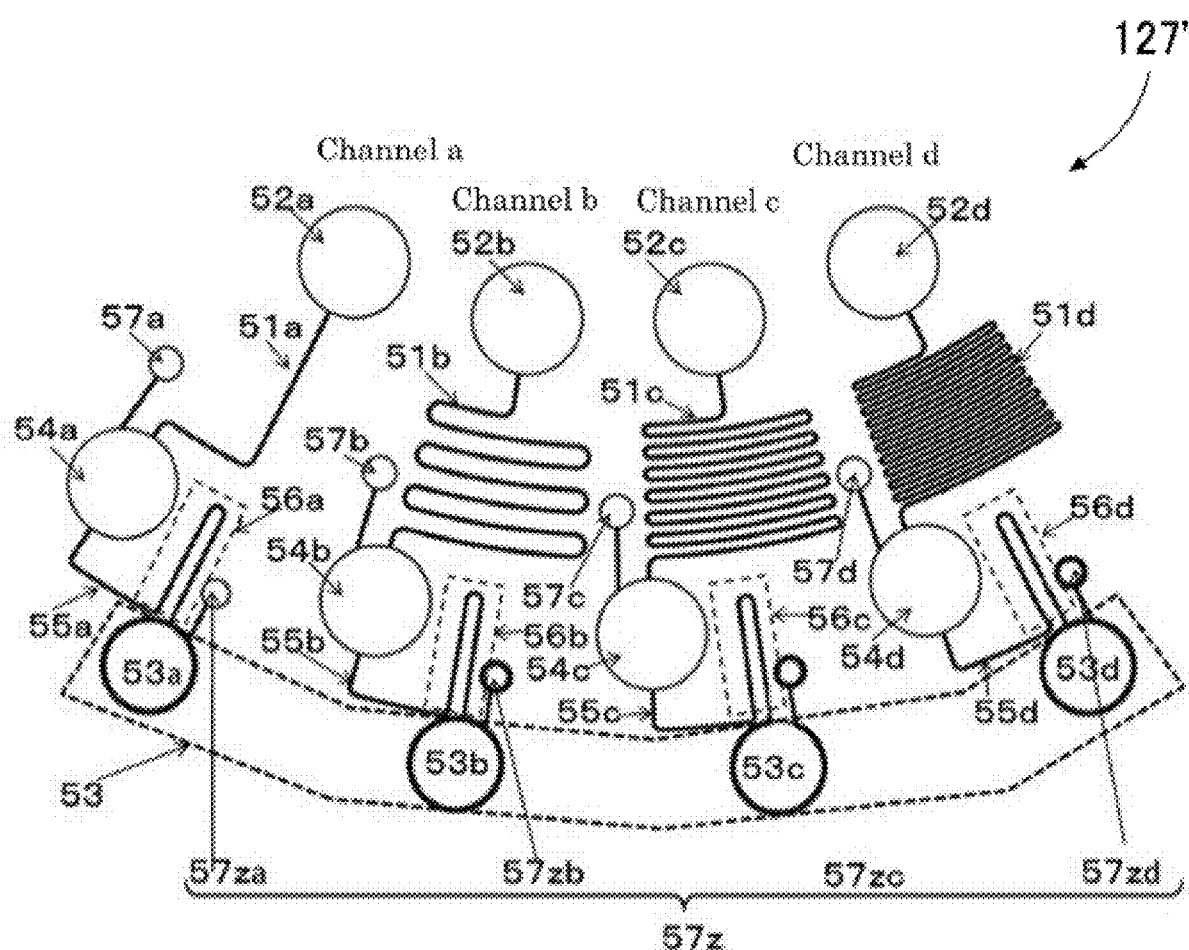
FIG. 24 is a view illustrating an example of a testing apparatus used for operation verification of a testing apparatus of a second embodiment.

FIG. 24 is a plan view of a testing apparatus 127' configured for operation verification of the testing apparatus 127 of the second embodiment. The testing apparatus 127' of FIG. 24 is produced for operation verification of whether or not the analytical method of FIG. 23 can be realized with the testing apparatus 127 of the second embodiment illustrated in FIG. 22.

The testing apparatus 127' of FIG. 24 has the same configuration as the testing apparatus 127 of the second embodiment illustrated in FIG. 22 except that the chamber 53 is divided into four chambers 53a to 53d, and the waste liquid tank 58 and the siphon structure 56z between the chamber and the waste liquid tank 58 are removed. The components of the testing apparatus 127' of FIG. 24 that are the same as those of the testing apparatus 127 of the second embodiment already described will be denoted by the same reference numerals, description of such components will be skipped.

Vents 57za to 57zd are produced correspondingly to the chambers 53a to 53d corresponding to the chamber 53 and depicted dividedly for the respective channels. The vents 57za to 57zd are formed as one vent 57z when the chambers are combined into one.

In an experiment using the testing apparatus 127' of FIG. 24, the rotation is at a constant rotation number (1,700 rpm). As the testing apparatus 127', one in which the PDMS layer 192 illustrated in FIG. 20 has a thickness of 3 mm is used.

In the experiment, water colored in blue is used as the liquid to be flowed through the testing apparatus 127' for visibility, and the time taken from start of rotation of the disk until start of injection of the liquid into the chamber is measured.

As an observation method, an image capturing system formed of a servo motor and a stroboscope is used, to employ a method of capturing images with synchronization of strobe flashing with disk rotation.

As a result, (1) it was successfully confirmed that a liquid did not flow into the flow path merely by injection into the first reservoir because PDMS, which was the material of the testing apparatus 127', was hydrophobic, and that the liquid started to flow in response to application of a centrifugal force by rotation of the testing apparatus 127'. (2) It was successfully confirmed that fluid storage in the second reservoir was the fastest through the channel a having the shortest resistance flow path and start of fluid injection through climbing up and down the siphon structure was first into the chamber 53a, and that storage subsequently started in order of the channels b, c, and d and the liquids of all of the channels moved to the respective chambers 53a to 53d.

Figure 25:
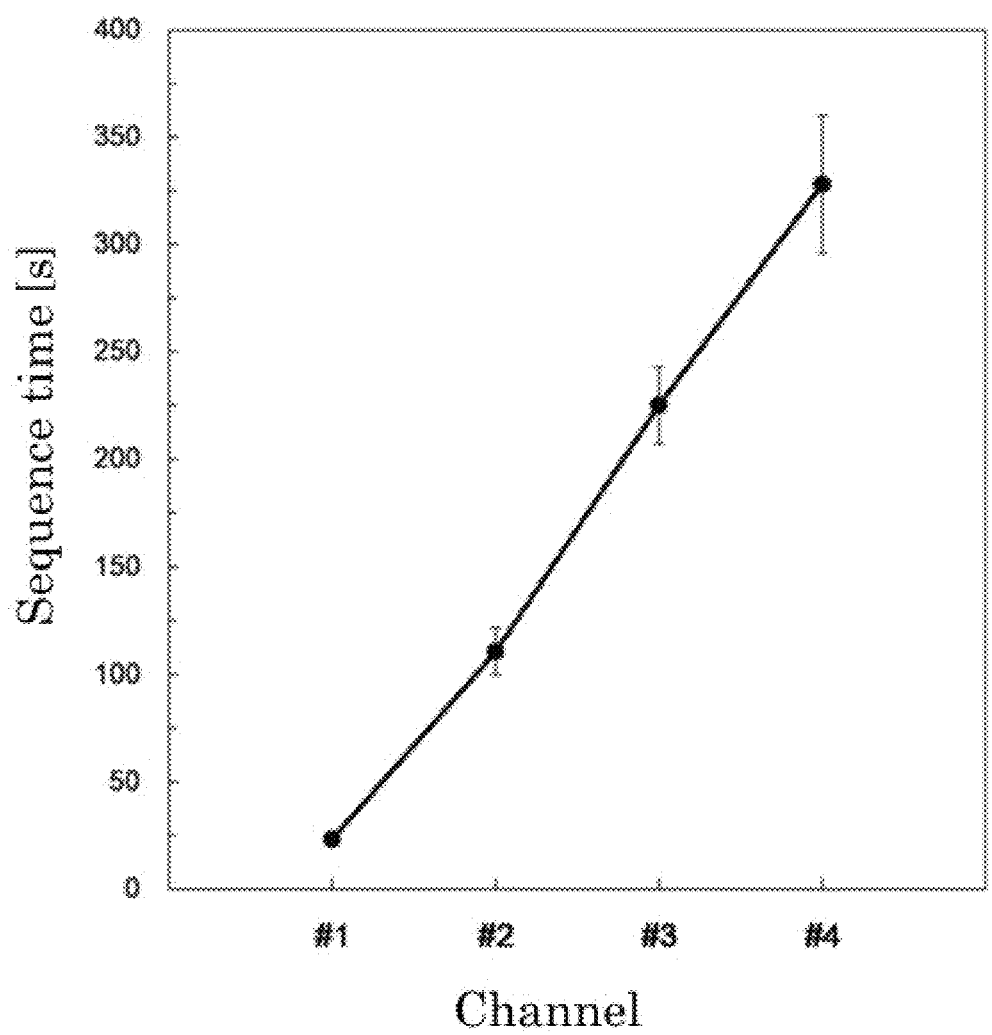
FIG. 25 is a graph plotting an example of measured results of time taken until a liquid in each channel flows into a chamber in a testing apparatus of a first embodiment of FIG. 18.

FIG. 25 is a graph plotting measured results of time taken until the liquid in each channel flows into a chamber in the testing apparatus 127' of FIG. 24. FIG. 25 plots the average and standard deviation of the results of the same experiment performed three times for measuring the time taken from when rotation of the testing apparatus 127' was started, i.e., the liquids stored in the first reservoirs of the respective channels received an external force at the same time until when the liquids started to be injected into the chambers 53a to 53d.

In any run of the experiment, the sequence orders were not switched and a high reproducibility was confirmed. In the present experiment, fluid control for 5 minutes or longer in steady rotation was realized without the need for stopping the rotation of the disk.

Moreover, highly flexible designing can be realized with adjustment of the rotation speed of the device, the length of the flow path, and the diameter of the flow path. Hence, it is possible to produce a testing apparatus that can cater to automation of chemical analysis processes such as enzyme immunoassay (ELISA) described above.

Third Embodiment of Testing Apparatus

Figure 26:
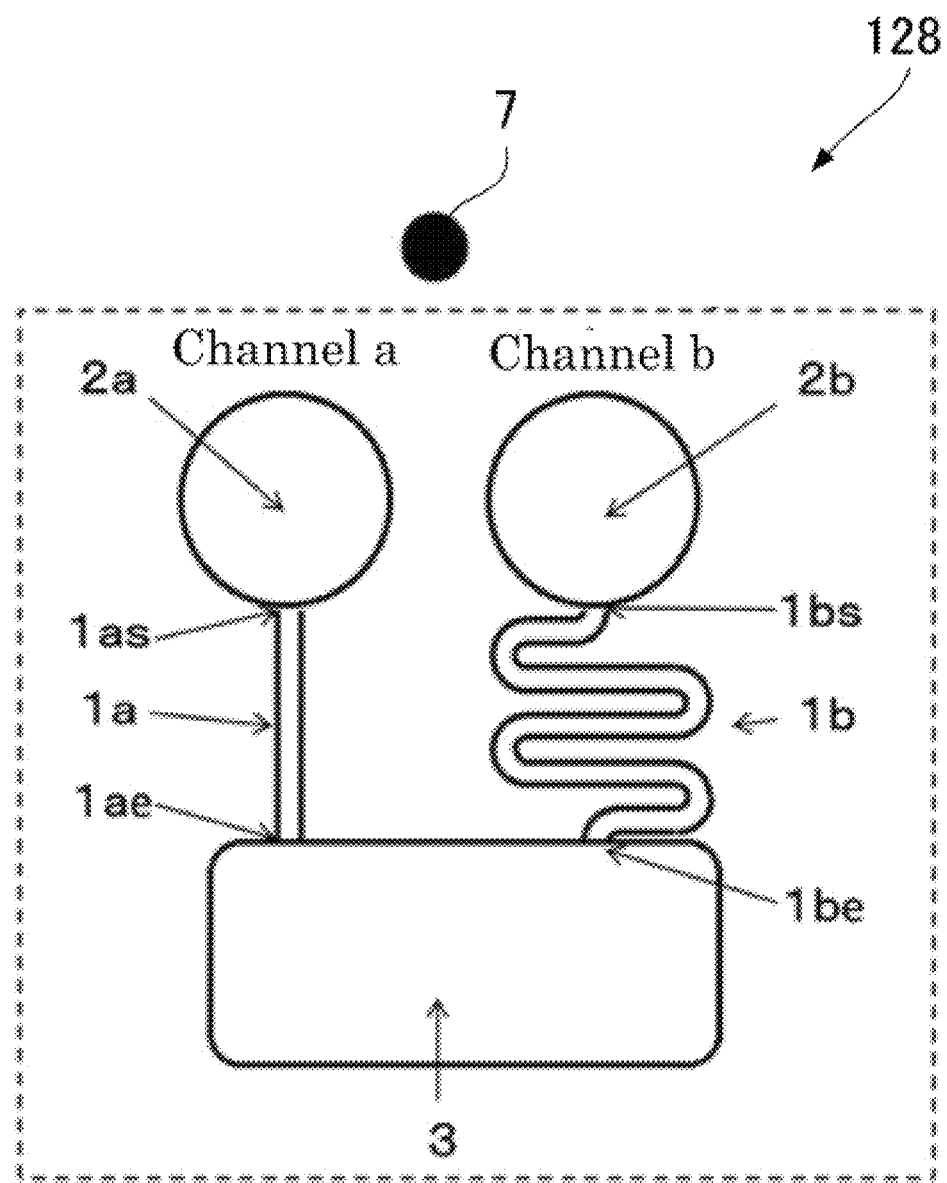
FIG. 26 is a view illustrating an example of a testing apparatus of a third embodiment.

FIG. 26 is a plan view of the testing apparatus 128 of the third embodiment. The testing apparatus 128 of the third embodiment has the same configuration as the testing apparatus 18 of the first embodiment except that the second reservoirs and the flow paths joining the second reservoirs to the chamber are removed from the testing apparatus 18 of the first embodiment illustrated in FIG. 18 for simplification. The components of the testing apparatus 128 of the third embodiment that are the same as those of the testing apparatus 18 of the first embodiment already described will be denoted by the same reference numerals, and description of such components will be skipped.

The channels a and b include first reservoirs 2a and 2b and flow paths 1a and 1b, respectively.

The flow path 1a of the channel a is joined to the first reservoir 2a and the chamber 3.

The flow path 1b of the channel b is joined to the first reservoir 2b and the chamber 3.

As in the testing apparatus 18 of the first embodiment, the flow path 1a and the flow path 1b are configured to be varied in at least one of flow path length, flow path girth, and flow path shape, and are configured to have liquid injection start successively differently through the channels a and b.

The testing apparatus 128 of the third embodiment is useful in terms of simplification of the testing apparatus configuration, when analysis sequencing can be dealt with without a siphon structure in the testing apparatus 18 of the first embodiment.

Fourth Embodiment of Testing Apparatus

Figure 27:
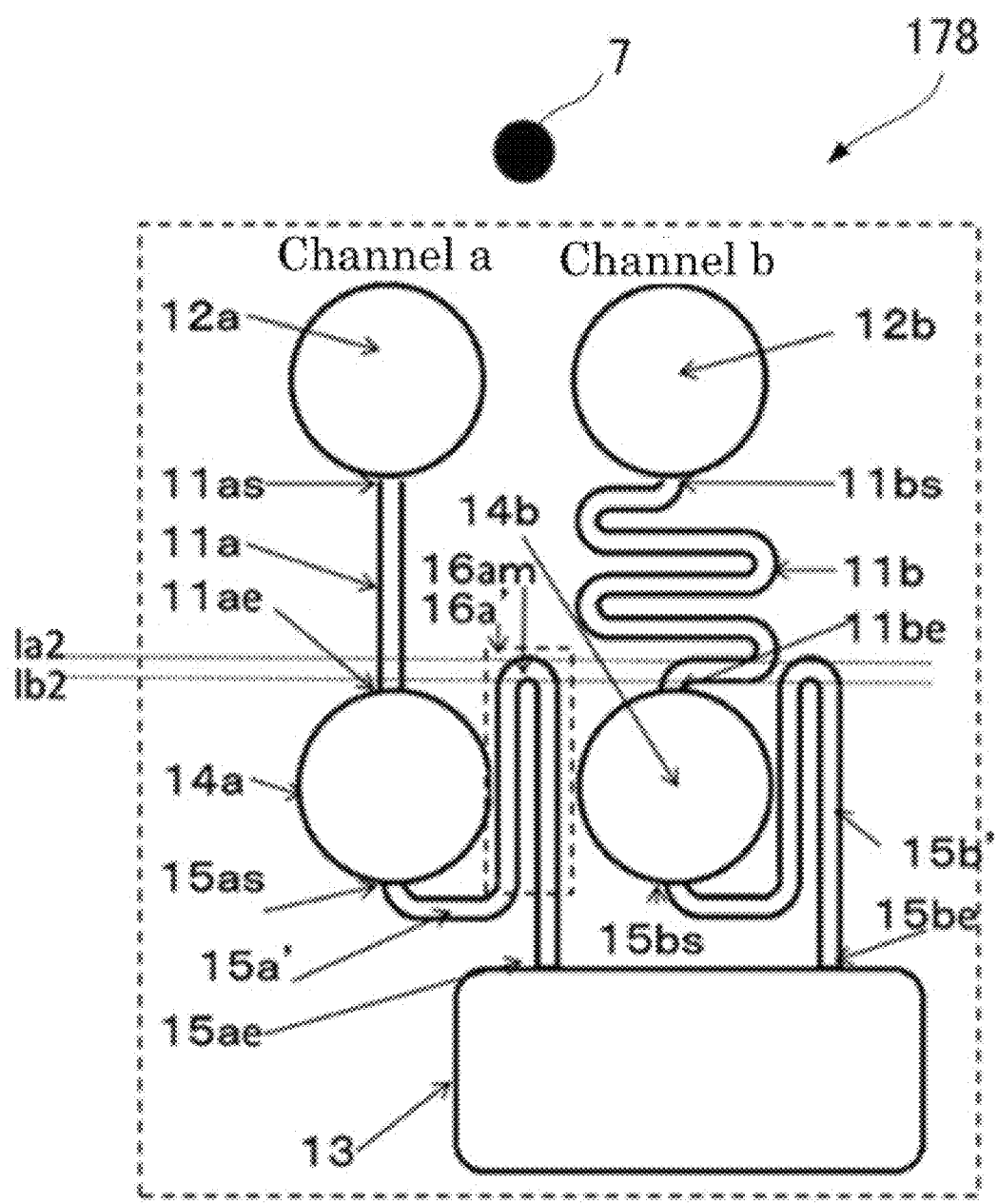
FIG. 27 is a view illustrating an example of a testing apparatus of a fourth embodiment.

FIG. 27 is a plan view of a testing apparatus 178 of the fourth embodiment. The testing apparatus 178 of the fourth embodiment has the same configuration as the testing apparatus 18 of the first embodiment except that the siphon structure 16a of the testing apparatus 18 of the first embodiment illustrated in FIG. 18 is changed. The components of the testing apparatus 178 of the fourth embodiment that are the same as those of the testing apparatus 18 of the first embodiment already described will be denoted by the same reference numerals, and description of such components will be skipped.

A siphon structure 16a' of the testing apparatus 178 of the fourth embodiment is configured to have a bent point 16am at a position higher than an inlet port 11ae at the top of the second reservoir 14a. The channel a will be described here, but the same applies to the channel b.

As described above, when the upper liquid surface of the liquid stored in the second reservoir 14a reaches a level above the bent point of the siphon structure 16a', the liquid starts to flow through the siphon structure 16a'.

As illustrated for the channel a in FIG. 27, in order for the liquid to be filled to the position of the bent point 16am, the upper liquid surface of the side into which the liquid comes flowing needs to reach a level lb2 to a level la2 illustrated in FIG. 27. That is, in the testing apparatus 178 of the fourth embodiment, after the second reservoir 14a is filled with the liquid, the liquid starts to flow into the chamber 13.

In an actual operation, the liquid surface level at which the liquid starts to flow out through the siphon structure varies depending on, for example, the structure of the testing apparatus, the properties of the solution, and the environmental conditions during use. In the testing apparatus 18 of the first embodiment, variation of the liquid surface level is strongly influential because the liquid surface level at which the liquid starts to flow out through the siphon structure is about la1 and lb1.

Meanwhile, in the testing apparatus 178 of the fourth embodiment, a change occurs in a manner that the second reservoir 14a and the flow path 11a are to be filled with the liquid when the second reservoir 14a is filled to the full, making it possible to control the liquid to flow out through the siphon structure at a breath at the time of the change. Hence, the testing apparatus 178 of the fourth embodiment can suppress variation of the timing at which the liquid starts to flow out through the siphon structure.

Fifth Embodiment of Testing Apparatus

Figure 28:
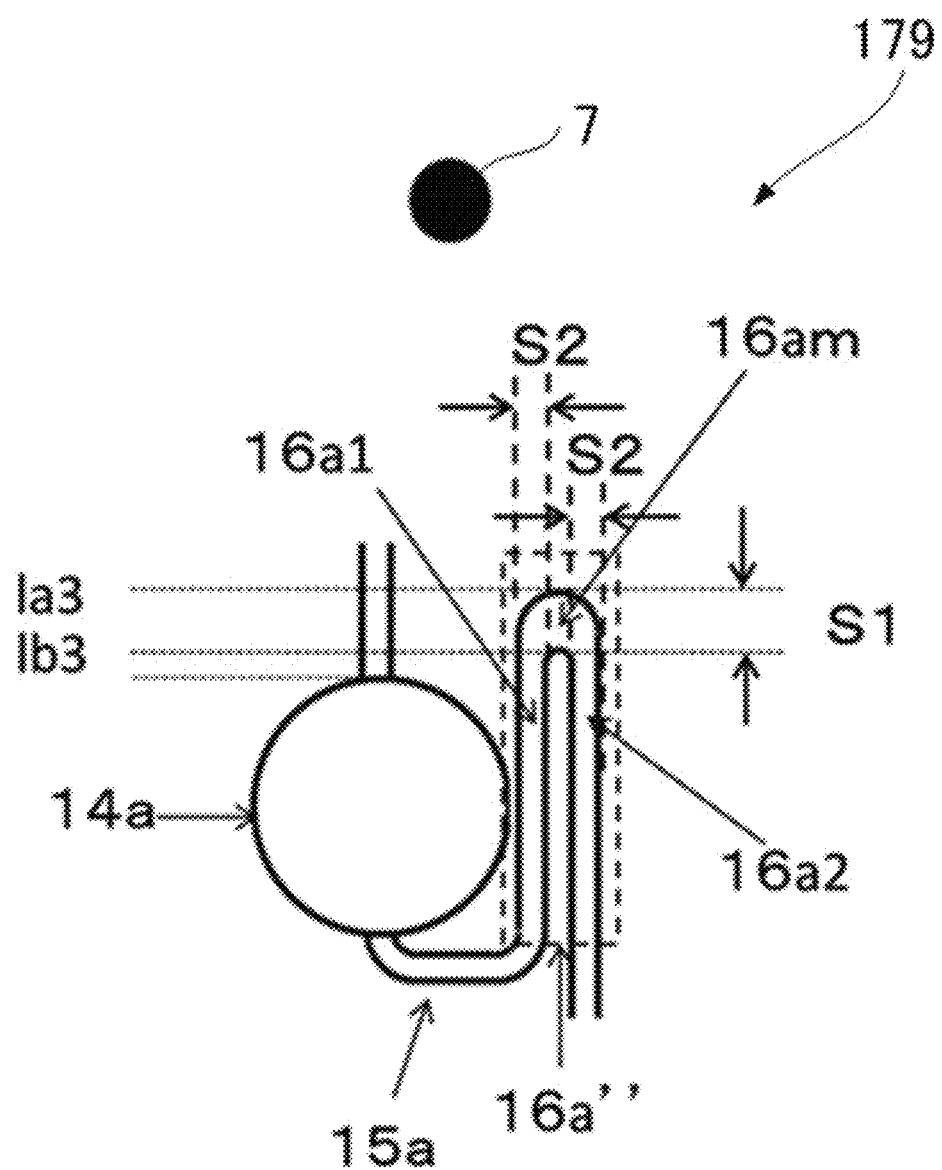
FIG. 28 is a view illustrating an example of a testing apparatus of a fifth embodiment.

FIG. 28 is a view illustrating a part of a testing apparatus 179 of the fifth embodiment. The testing apparatus 179 of the fifth embodiment has the same configuration as the testing apparatus 18 of the first embodiment except that the siphon structure 16a of the testing apparatus 18 of the first embodiment illustrated in FIG. 18 is changed, and only a siphon structure 16a" is illustrated in FIG. 28 for simplification. The components of the testing apparatus 179 of the fifth embodiment that are the same as those of the testing apparatus 18 of the first embodiment already described will be denoted by the same reference numerals, and description of such components will be skipped.

The siphon structure 16a" of the testing apparatus 179 of the fifth embodiment is configured in a manner that the girth of the thin tube of a flow path 15a is greater at a bent point 16am than at a first flow path section 16a1 and a second flow path section 16a2. The cross-sectional area S2 of the thin tube of the first flow path section 16a1 and the second flow path section 16a2 is smaller than the cross-sectional area S1 of the thin tube at the bent point. That is, the cross-sectional area S2 is larger at the bent point 16am than at other sections.

As a result, the testing apparatus 179 of the fifth embodiment can ease the surface tension between the liquid flowing through the flow path and the thin tube when the liquid is passing by the bent point of the siphon structure. This enables the liquid to pass by the bent point easily even when an external force applied to the liquid is weak, making it possible to reduce the rotation number during an analysis. As a result, the liquid passing through each channel can be provided with a long time to pass. This makes it possible to provide an analysis using the testing apparatus 179 of the fifth embodiment with a long time to be performed. This is highly effective when a reaction for the analysis takes a long time.

Sixth Embodiment of Testing Apparatus

Figure 29:
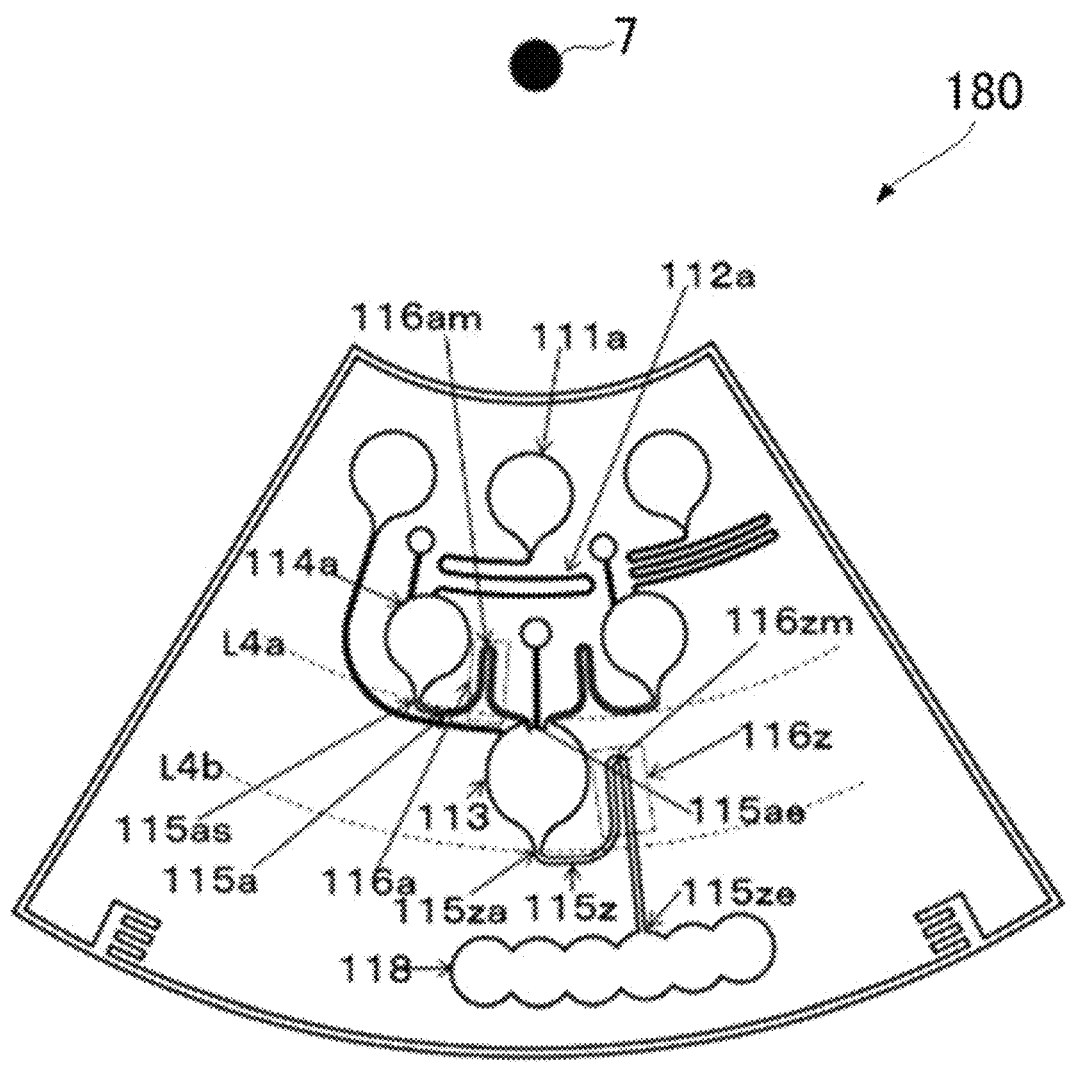
FIG. 29 is a view illustrating an example of a testing apparatus of a sixth embodiment.

FIG. 29 is a plan view of a testing apparatus 180 of the sixth embodiment. The channel a of the testing apparatus 180 of the sixth embodiment illustrated in FIG. 29 includes a first reservoir 111a, a flow path 112a, a second reservoir 114a, and a flow path 115a.

The channel a and two channels are independently joined to a chamber 113 of the testing apparatus 180 of the sixth embodiment. There is a flow path 115z joining the chamber 113 to a waste liquid tank 118. The flow path 115a has a first siphon structure 116a, and the flow path 115z has a second siphon structure 116z.

The first siphon structure 116a of the testing apparatus 180 of the sixth embodiment includes a first flow path section, which is a flow path formed in a first direction heading for the rotation axis position 7 and a second flow path section, which is a flow path formed in a second direction in which an external force acts oppositely to the first direction, like the siphon structures 56a to 56d of the testing apparatus 127 of the second embodiment and the siphon structures 16a and 16b of the testing apparatus 18 of the first embodiment.

The second siphon structure 116z includes a third flow path section, which is a flow path formed in a third direction heading for the rotation axis position 7 and a fourth flow path section, which is a flow path formed in a fourth direction in which an external force acts oppositely to the third direction, like the siphon structure 56z of the testing apparatus 127 of the second embodiment.

Figure 30:
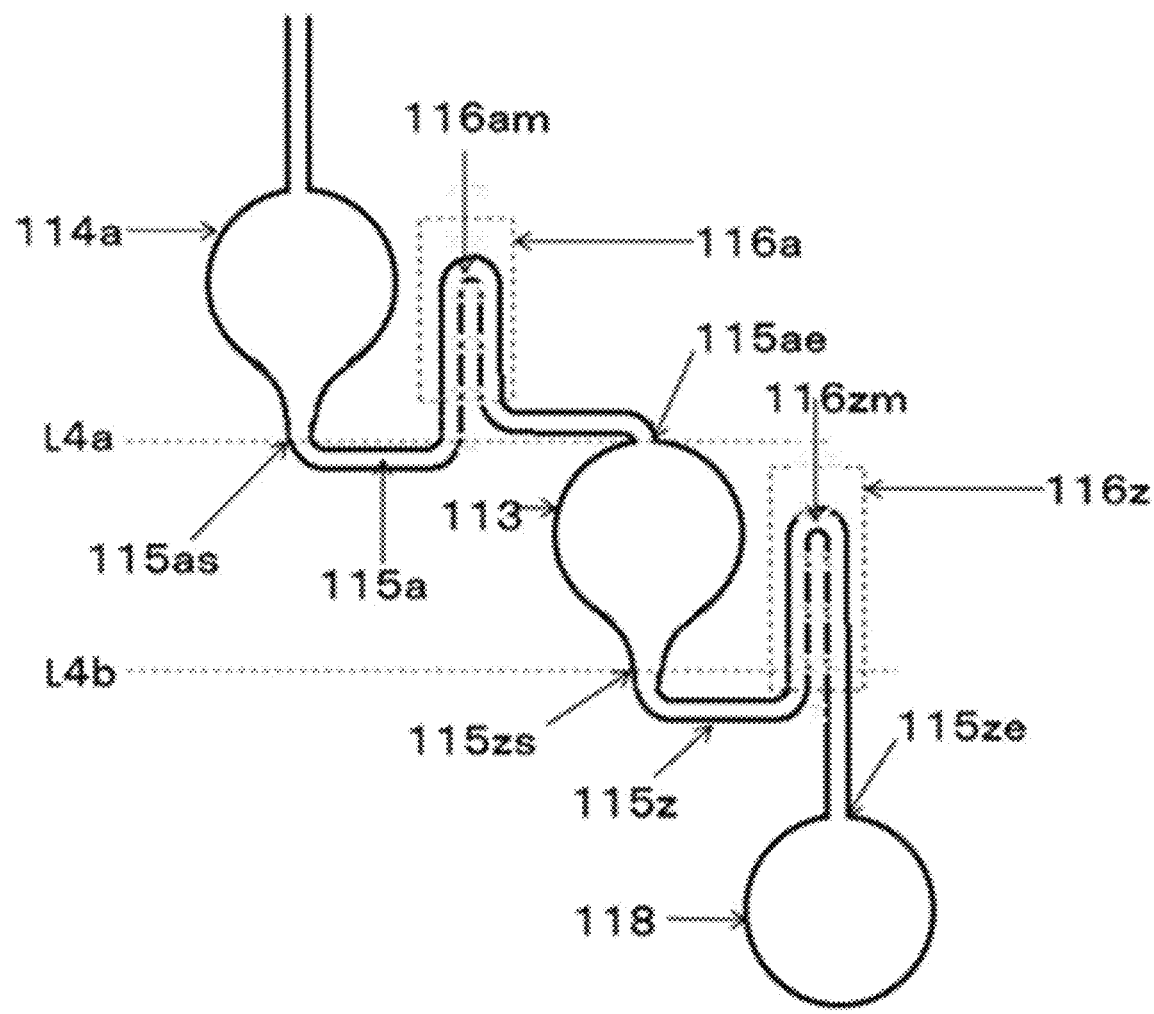
FIG. 30 is a partially enlarged view of a second reservoir, a flow path, a chamber, and a waste liquid tank of a channel a of a testing apparatus of a sixth embodiment of FIG. 29.
Figure 31A:
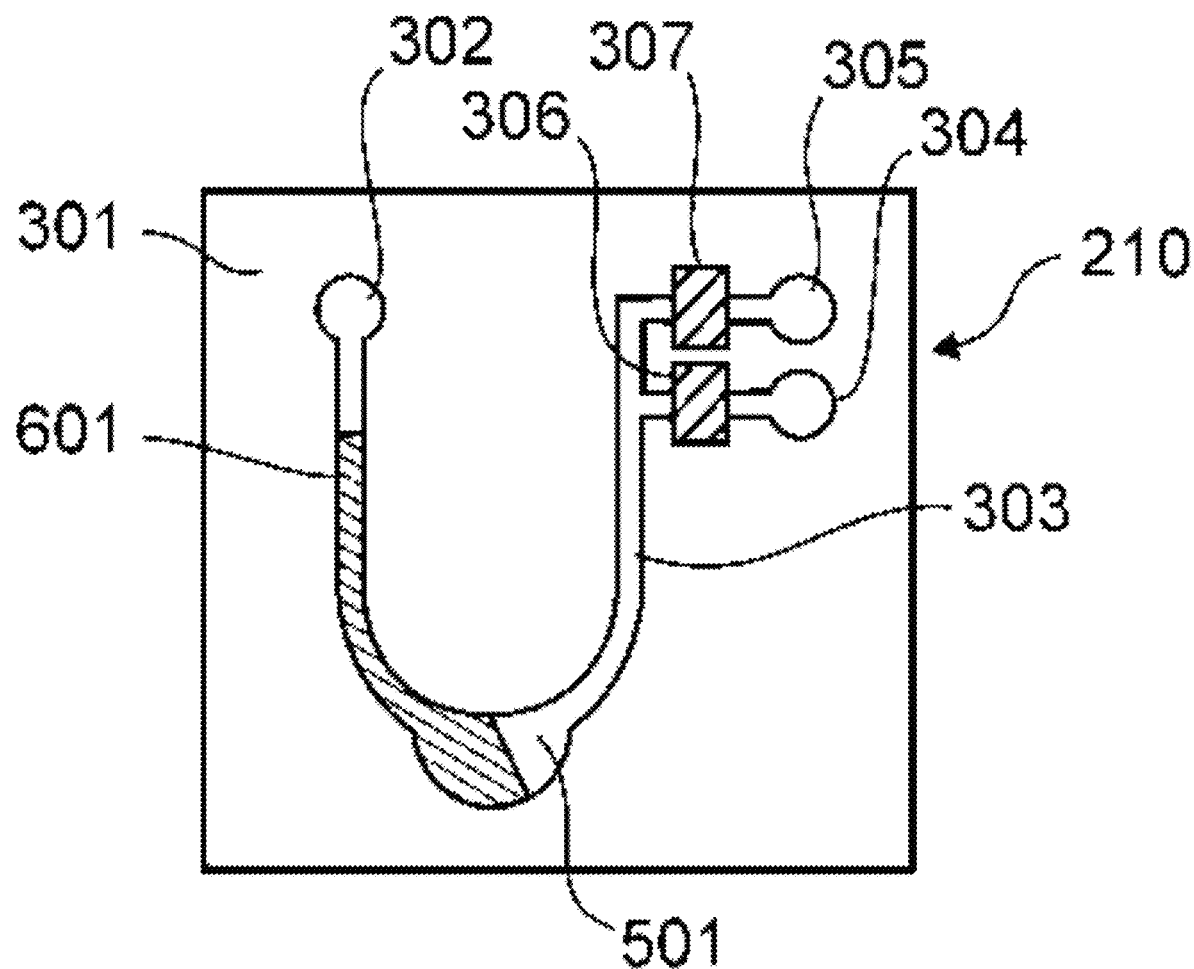
FIG. 31A is a schematic view illustrating an example of an existing blood analyzing device.
Figure 31B:
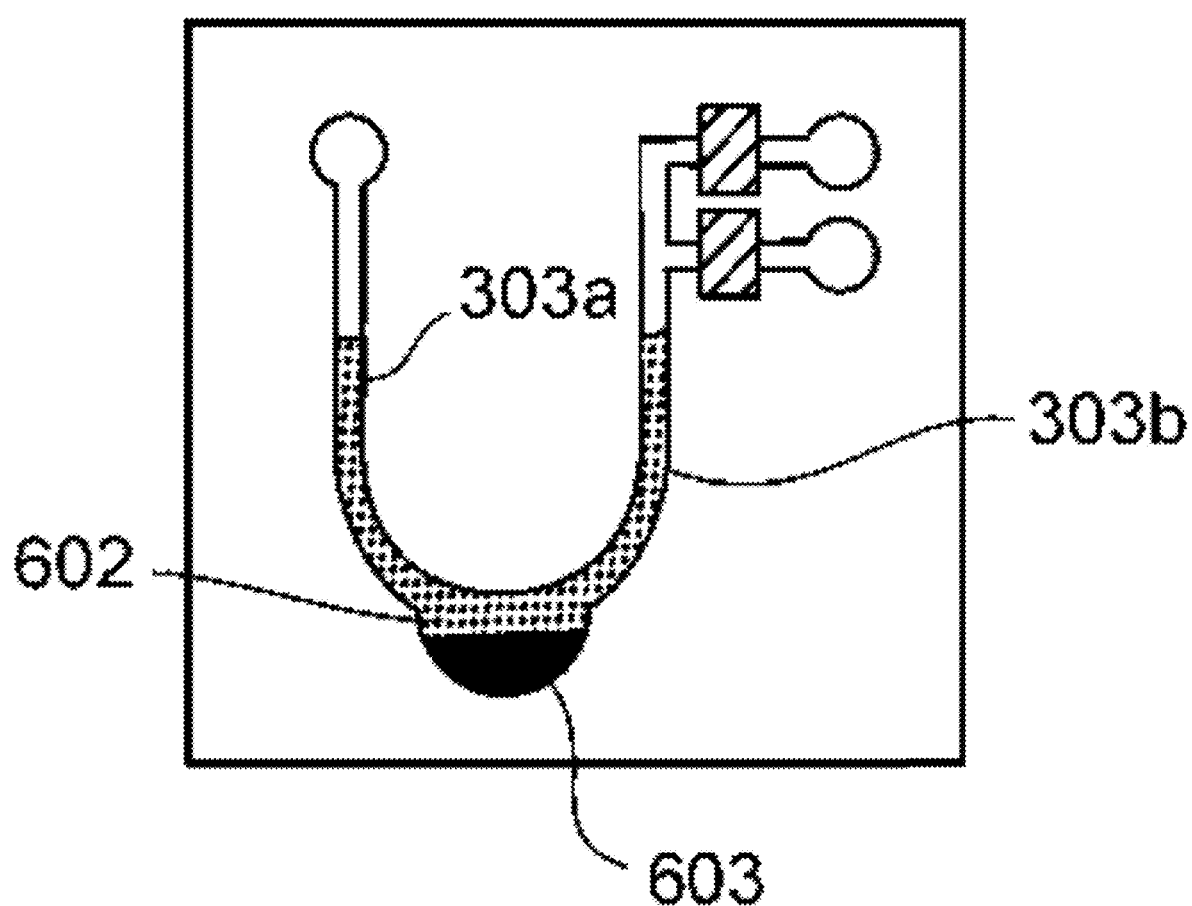
FIG. 31B is a schematic view illustrating an example of an existing blood analyzing device.
Figure 31C:
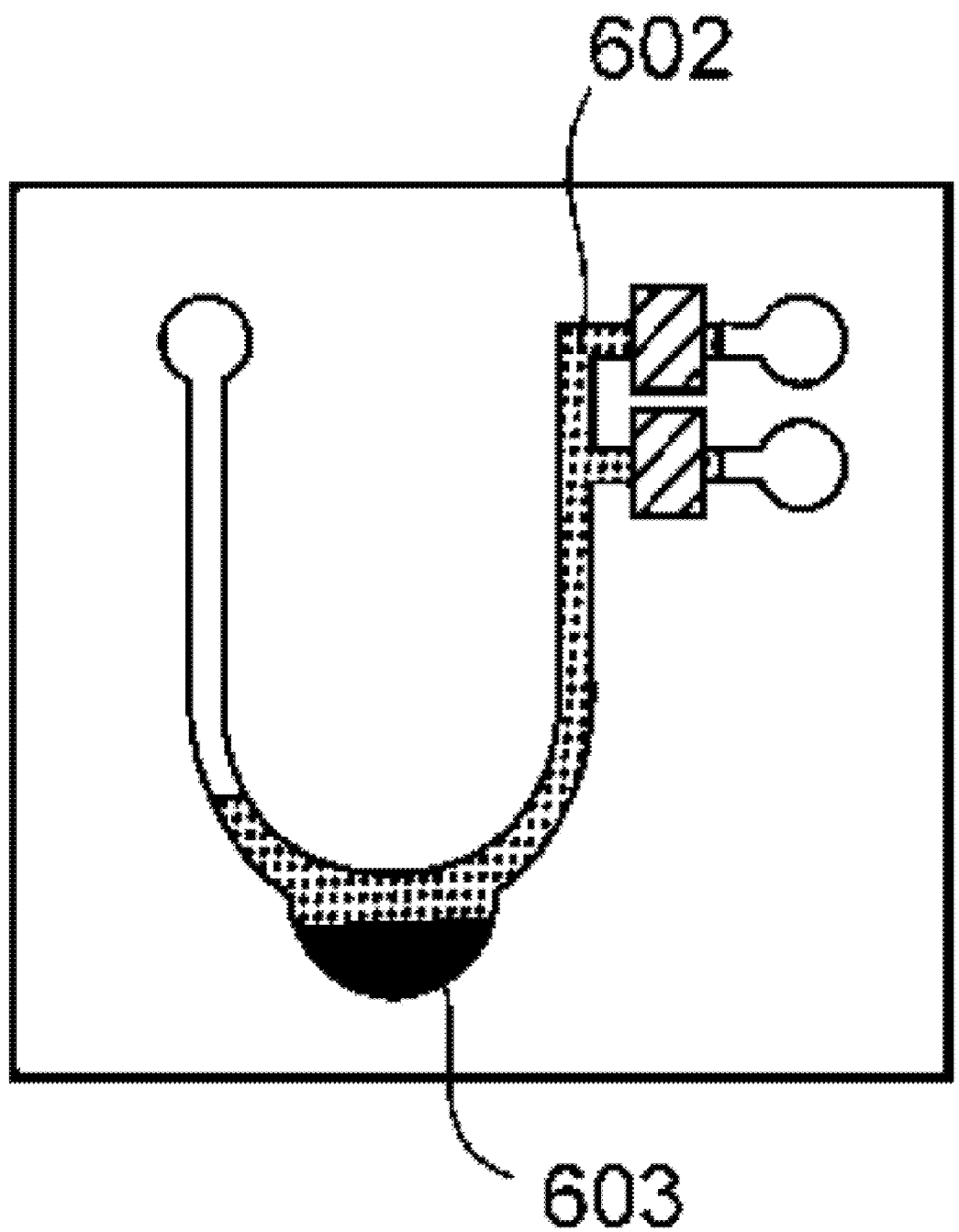
FIG. 31C is a schematic view illustrating an example of an existing blood analyzing device.

FIG. 30 is an expanded view of a part of the testing apparatus 180 of the sixth embodiment, extracting the second reservoir 114a and the flow path 115a of the channel a, the chamber 113, the flow path 115z, and the waste liquid tank 118.

FIG. 30 only illustrates a joined channel a with respect to the chamber 113, and does not illustrate other joined channels for simplification.

In biopsies and chemical analyses, it is required to inject a sample, a reagent, and a cleaning liquid in a predetermined order in predetermined amounts into the chamber in accordance with the procedure of tests and analyses. For example, when performing a test using the enzyme immunoassay method illustrated in FIG. 23, it is necessary to inject, for example, a sample (blood plasma) and a color reagent (matrix) into the chamber 113 in predetermined amounts infallibly. Moreover, the sample (blood plasma) needs to be kept stored in the chamber 113 for a predetermined period of time in order to undergo reaction with the capture antibody 104 and the labeled antibody 103 for detection previously coated in the chamber 113. Hence, it is necessary to inject the sample in a predetermined amount into the chamber 113 without interruption.

The channel a for injecting the sample (blood plasma) into the chamber 113 is designed in a manner that the liquid may climb up and down the bent point 116am of the first structure 116a and the sample may flow into the chamber 113 at a breath when the sample stored in the first reservoir 111a has mostly moved into the second reservoir 114a. However, actually, the testing apparatus may have variation attributable to production, or environmental conditions (e.g., temperature, humidity, and atmospheric pressure) during testing may vary. Therefore, in an assumable case, despite that the sample is still remaining in the first reservoir 111a and the flow path 112a, the sample stored in the second reservoir 114a already may climb up and down the bent point 116am to be injected into the chamber 113.

The sample continues flowing so long as the sample is filling the flow path 115a. However, if the sample from the preceding flow path 112a flows into the second reservoir 114a in a low amount, air bubbles may mix. In such a case, the sample coming afterwards will be kept stored again in the chamber 113. As a result, the sample does not flow into the chamber 113 in an initially designed amount, leading to an inaccurate testing.

In order to prevent this, the output port 115as of the second reservoir 114a and a second point, which is the position of the inlet port 115ae of the chamber 113 are configured to be located on the circumference (L4a) of a circle centered on the rotation axis position (reference point) 7. That is, the outlet port 115as of the second reservoir 114a and the inlet port 115ae of the chamber 113 are configured to have the same distance from the rotation axis position 7. In this case, even if any already stored sample flows out to the flow path 115a before the sample is entirely transferred to the second reservoir 114a, the liquid surface of the second reservoir 114a does not fall below the output port 115as, making it possible for the liquid to be kept stored. Hence, the liquid to come flowing afterwards can be flowed into the chamber 113 successively.

It is not until the water load of the liquid at the outlet port becomes higher than the capillary force of the flow path 115a that the liquid starts to flow into the flow path 115a from the outlet port of the second reservoir 114a. For the testing apparatus 180 of the sixth embodiment to have a more effective configuration, the outlet port of the second reservoir 114a may be a first point at which the capillary force and the water load are equal, and the first point and the point at the inlet port of the chamber may have the same distance from the rotation axis position (reference point) 7.

Meanwhile, when sending out a sample liquid from the chamber 113 and cleaning the chamber to terminate a reaction, it is preferable to completely flow away the liquid stored in the chamber 113. Hence, it is preferable that the outlet port 115zs of the chamber 113 be closer than the inlet port of the waste liquid tank 118 to the rotation axis position 7. The inlet port 115ze of the waste liquid tank may be set outside, i.e., at the downstream side of the circumference L4b of the circle centered on the rotation axis position 7.

More specifically, the distance between the rotation axis position 7 and a fourth point, which is a position at which the inlet port of the waste liquid tank 118 is joined to the flow path 115z may be greater than the distance between the rotation axis position 7 and a third point, which is a position at which the outlet port of the chamber 113 is joined to the flow path 115z, so that the water load at a fifth point, which is a position of the liquid that flows out from the outlet port of the chamber 113 into the flow path 115z, may be higher than the capillary force of the flow path 115z at the outlet port of the chamber 113.

The testing apparatus of the present invention overcomes the risks of leak and mixed presence of liquids used in, for example, biopsies and chemical tests, and can perform the testing steps sequentially. For this purpose, the testing apparatus includes (1) a first reservoir configured to store a liquid initially, (2) a first sub-device configured to transfer the stored liquid with time difference, and (3) a second sub-device including a chamber configured to allow the liquid transferred thereto to undergo reaction sequentially (and as the case may be, discharge the reaction product).

In the testing apparatus 18 of the first embodiment, 12a and 12b of FIG. 18 correspond to the first reservoir.

The second sub-device is formed of the flow paths 11a and 11b, the second reservoirs 14a and 14b, and the flow paths 15a and 15b.

The siphon structure 16a and 16b are also the elements of the second sub-device

The chamber 13 corresponds to the first sub-device.

In the testing apparatus 127 of the second embodiment, 52a to 52d of FIG. 22 correspond to the first reservoir.

The second sub-device is formed of the flow paths 51a to 51d, the second reservoirs 54a to 54d, and the flow paths 55a to 55d.

The siphon structures 56a to 56b are also the elements of the second sub-device.

The chamber 53, the flow path 55z, and the waste liquid tank 58 correspond to the first sub-device.

The siphon structure 56z is also the element of the second sub-device.

In the testing apparatus 127', of which operation is illustrated in FIG. 23 and of which configuration corresponds to the testing apparatus 127 of the second embodiment illustrated in FIG. 22 from which the flow path 55z and the waste liquid tank 58 are removed, the number of channels is varied from the testing apparatus 18 of the first embodiment, the other components are the same as the testing apparatus 18 of the first embodiment, and the chamber 53 corresponds to the first sub-device.

In the testing apparatus 128 of the third embodiment, 2a and 2b of FIG. 26 correspond to the first reservoir. The flow paths 1a and 1b correspond to the second sub-device. The chamber 13 corresponds to the first sub-device.

In the testing apparatus 178 of the fourth embodiment, which is changed to have the siphon structure 16a' as illustrated in FIG. 27, the first sub-device and the second sub-device are defined the same as in the testing apparatus 18 of the first embodiment and the testing apparatus 127 of the second embodiment. The siphon structure 16a' is also the element of the second-sub-device.

In the testing apparatus 179 of the fifth embodiment, which is only changed in terms of the siphon structure to the siphon structure 16a" as illustrated in FIG. 28, the second sub-device is defined the same as in the testing apparatus 18 of the first embodiment, the testing apparatus 127 of the second embodiment, and the testing apparatus 178f the fourth embodiment.

In the testing apparatus 180 of the sixth embodiment, 111a of FIG. 29 corresponds to the first reservoir.

The second sub-device includes the flow path 112a, the second reservoir 114a, and the flow path 115a. The first siphon structure 116a is also the element of the second sub-device.

The first sub-device includes the chamber 113, the flow path 115z, and the waste liquid tank 118. The second siphon structure 116z is also the element of the first sub-device.

The testing apparatus 180 of the sixth embodiment also includes a channel that leads from a reservoir at the left-hand side of the first reservoir 111a in FIG. 29 to the chamber 113 through a flow path. However, these components are not particularly categorized here. Accordingly, the testing apparatus 180 of the sixth embodiment illustrated in FIG. 29 is also one modified example of the testing apparatus 127 of the second embodiment.

As described above, the testing apparatus of the present invention including no valve structure requires no valve opening or closing operation from outside, and can efficiently perform testing with a simple structure that only needs an external force to be applied.

Aspects of the present invention are, for example, as follows.

<1> A separating apparatus, including:
 a separating unit configured to apply an external force to a fluid sample containing two or more components immiscible with each other and having different specific gravities to separate the fluid sample into a separation target and a non-separation target; and
 a transfer mechanism configured to apply a pressure to the separation target separated by the separating unit to transfer the separation target.

<2> The separating apparatus according to claim 1,
 wherein the pressure is applied in a manner to pressurize the separation target separated.

<3> The separating apparatus according to <1> or <2>, including
 a storing unit configured to store the separation target transferred by the transfer mechanism.

<4> The separating apparatus according to any one of <1> to <3>,
 wherein the separating unit includes a separating chamber, and applies a centrifugal force as the external force to the fluid sample in the separating chamber to separate the fluid sample into the separation target and the non-separation target.

<5> The separating apparatus according to <4>,
 wherein the transfer mechanism transfers a pressurizing medium into the separating chamber to transfer the separation target in the separating chamber to outside the separating chamber by a pressure of the pressurizing medium.

<6> The separating apparatus according to <5>,
 wherein the pressurizing medium is at least one selected from the group consisting of liquids and gases, and is immiscible with the separation target.

<7> The separating apparatus according to any one of <4> to <6>,
 wherein the separating chamber is disposed on a rotatable rotating body.

<8> A testing apparatus, including:
 a separating unit formed of the separating apparatus according to any one of <1> to <7>; and
 a testing unit configured to test the separation target separated and transferred by the separating unit.

<9> The testing apparatus according to <8>,
 wherein the testing unit tests the separation target in a state that an external force that is the same as the external force applied to the separating unit is applied to the testing unit.

<10> A separating device used in any of the separating apparatus according to any one of <1> to <7> and the testing apparatus according to <8> or <9>, the separating device including:
 an introducing unit into which a fluid sample is introduced;
 a separating chamber communicably joined to the introducing unit and capable of separating the fluid sample into two or more fractions in response to application of an external force;

a pressurizing medium chamber communicating with the separating chamber and capable of transferring a pressurizing medium into the separating chamber in response to application of an external force; and a transfer path communicating with the separating chamber and capable of transferring the fractions in the separating chamber to outside the separating chamber in response to application of an external force.

<11> The separating device according to <10>, including
a storing unit communicating with the transfer path and capable of storing the fractions transferred thereto through the transfer path in response to application of an external force.

<12> The separating device according to <10> or <11>,
wherein the introducing unit, the separating chamber, the pressurizing medium chamber, and the transfer path are on a rotatable rotating body, and
wherein when a centrifugal force is applied as the external force, the fluid sample introduced into the introducing unit can be transferred to the separating chamber and then to the transfer path.

<13> A separating method, including:
applying an external force to a fluid sample containing two or more components immiscible with each other and having different specific gravities, to separate the fluid sample into a separation target and a non-separation target; and
applying a pressure to the separation target separated in the applying, to transfer the separation target.

<14> The separating method according to <13>, including storing the separation target transferred in the applying.

<15> The separating method according to <13> or <14>,
wherein the applying an external force is performed using a separating chamber, and a centrifugal force is applied as the external force to the fluid sample in the separating chamber to separate the fluid sample into the separation target and the non-separation target.

<16> The separating method according to <15>,
wherein in the applying a pressure, a pressurizing medium is transferred into the separating chamber to transfer the separation target in the separating chamber to outside the separating chamber by a pressure of the pressurizing medium.

<17> The separating method according to <16>,
wherein the pressurizing medium is at least one selected from the group consisting of liquids and gases, and is immiscible with the separation target.

<18> The separating method according to any one of <15> to <17>,
wherein the separating chamber is disposed on a rotatable rotating body.

<19> A testing method, including:
applying an external force to a fluid sample containing two or more components immiscible with each other and having different specific gravities, to separate the fluid sample into a separation target and a non-separation target;
applying a pressure to the separation target separated in the applying, to transfer the separation target; and
testing the separation target transferred in the applying.

<20> The testing method according to <19>,
wherein in the testing, the separation target is tested in a state that an external force that is the same as the external force applied in the applying an external force is applied.

The separating apparatus according to any one of <1> to <7>, the testing apparatus according to <8> or <9>, the separating device according to any one of <10> to <12>, the separating method according to any one of <13> to <18>, and the testing method according to <19> or <20> can solve the various problems in the related art described above and can achieve the object of the present invention described above.

REFERENCE SIGNS LIST 21 pressurizing medium introducing chamber
22 sample introducing chamber
23 storing chamber
24 pressurizing medium chamber
26 bent flow path
27 siphon structure
31 separating chamber
40 separating apparatus
61 pressurizing medium introducing chamber
62 pressurizing medium chamber
63 internal pressure adjusting chamber
64 sample introducing chamber
65 separating chamber
66 storing chamber
68 bent flow path
69 siphon structure
80 separating apparatus

The invention claimed is:

1. A separating apparatus, comprising:
a separating unit including a separating chamber and configured to apply an external force to a fluid sample containing two or more components immiscible with each other and having different specific gravities to separate the fluid sample into a separation target and a non-separation target in the separating chamber; and
a transfer mechanism configured to transfer a pressurizing medium targeted at the separation target separated by the separating unit into the separating chamber by the external force to transfer the separation target in the separating chamber to outside the separating chamber by a pressure of the pressurizing medium,
wherein the transfer mechanism comprises: a pressurizing medium chamber configured to store the pressurizing medium; and a siphon structure provided on a flow path joining the pressurizing medium chamber to the separating chamber.

2. The separating apparatus according to claim 1,
wherein the pressure is applied in a manner to pressurize the separation target separated.

3. The separating apparatus according to claim 1, comprising
a storing unit configured to store the separation target transferred by the transfer mechanism.

4. The separating apparatus according to claim 1,
wherein the pressurizing medium comprises at least one selected from the group consisting of liquids and gases, and is immiscible with the separation target.

5. The separating apparatus according to claim 1,
wherein the separating chamber is disposed on a rotatable rotating body.

6. A testing apparatus, comprising:
a separating unit formed of the separating apparatus according to claim 1; and
a testing unit configured to test the separation target separated and transferred by the separating unit.

7. The testing apparatus according to claim 6,
wherein the testing unit tests the separation target in a state that an external force that is the same as the external force applied to the separating unit is applied to the testing unit.

8. A separating device used in the separating apparatus according to claim 1, the separating device comprising:
an introducing unit into which a fluid sample is introduced;
a separating chamber communicably joined to the introducing unit and capable of separating the fluid sample into two or more fractions in response to application of an external force;
a pressurizing medium chamber communicating with the separating chamber and capable of transferring a pressurizing medium into the separating chamber in response to application of an external force; and
a transfer path communicating with the separating chamber and capable of transferring the fractions in the separating chamber to outside the separating chamber in response to application of an external force.

9. The separating device according to claim 8, comprising a storing unit communicating with the transfer path and capable of storing the fractions transferred thereto through the transfer path in response to application of an external force.

10. The separating device according to claim 8,
wherein the introducing unit, the separating chamber, the pressurizing medium chamber, and the transfer path are on a rotatable rotating body, and
wherein when a centrifugal force is applied as the external force, the fluid sample introduced into the introducing unit can be transferred to the separating chamber and then to the transfer path.

11. A separating method, comprising:
applying an external force to a fluid sample containing two or more components immiscible with each other and having different specific gravities, to separate the fluid sample into a separation target and a non-separation target in a separating chamber; and
transferring a pressurizing medium, which is targeted at the separation target separated in the applying, into the separating chamber by the external force, to transfer the separation target in the separating chamber to outside the separating chamber by a pressure of the pressurizing medium,
wherein in the transferring, a transfer mechanism is used, the transfer mechanism including: a pressurizing medium chamber configured to store the pressurizing medium; and a siphon structure provided on a flow path joining the pressurizing medium chamber to the separating chamber.

12. A testing method, comprising:
applying an external force to a fluid sample containing two or more components immiscible with each other and having different specific gravities, to separate the fluid sample into a separation target and a non-separation target in a separating chamber;
transferring a pressurizing medium, which is targeted at the separation target separated in the applying, into the separating chamber by the external force, to transfer the separation target in the separating chamber to outside the separating chamber by a pressure of the pressurizing medium; and
testing the separation target transferred in the transferring,
wherein in the transferring, a transfer mechanism is used, the transfer mechanism including: a pressurizing medium chamber configured to store the pressurizing medium, and a siphon structure provided on a flow path joining the pressurizing medium chamber to the separating chamber.

13. The separating apparatus according to claim 1,
wherein the external force is a centrifugal force.

14. The separating method according to claim 11,
wherein the external force is a centrifugal force.

15. The testing method according to claim 12,
wherein the external force is a centrifugal force.

16. The separating apparatus according to claim 1,
wherein the transfer mechanism comprises an internal pressure adjusting chamber provided between the pressurizing medium chamber and the separating chamber and configured to transfer the separation target in the separating chamber to outside the separating chamber by a pressure generated when the pressurizing medium, which is a gas, is injected into the internal pressure adjusting chamber.

17. A separating device used in the testing apparatus according to claim 6, the separating device comprising:
an introducing unit into which a fluid sample is introduced;
a separating chamber communicably joined to the introducing unit and capable of separating the fluid sample into two or more fractions in response to application of an external force;
a pressurizing medium chamber communicating with the separating chamber and capable of transferring a pressurizing medium into the separating chamber in response to application of an external force; and
a transfer path communicating with the separating chamber and capable of transferring the fractions in the separating chamber to outside the separating chamber in response to application of an external force.

18. The separating device according to claim 17, comprising:
a storing unit communicating with the transfer path and capable of storing the fractions transferred thereto through the transfer path in response to application of an external force.

19. The separating device according to claim 17,
wherein the introducing unit, the separating chamber, the pressurizing medium chamber, and the transfer path are on a rotatable rotating body, and
wherein when a centrifugal force is applied as the external force, the fluid sample introduced into the introducing unit can be transferred to the separating chamber and then to the transfer path.

* * * * *